United States Patent
Ryba et al.

(10) Patent No.: US 10,004,550 B2
(45) Date of Patent: Jun. 26, 2018

(54) CRYOABLATION APPARATUSES, SYSTEMS, AND METHODS FOR RENAL NEUROMODULATION

(71) Applicant: Medtronic Ardian Luxembourg S.a.r.l., Luxembourg (LU)

(72) Inventors: Eric Ryba, Durango, CO (US); Naomi Buckley, Galway (IE); Benjamin J. Clark, Redwood City, CA (US); Danny Donovan, Galway (IE); Luke Hughes, Galway (IE); Brian Kelly, Galway (IE); Gwenda McMullin, Galway (IE); Karun D. Naga, Los Altos, CA (US); Stephen Nash, Galway (IE); Roman Turovskiy, San Francisco, CA (US); Lana Wooley, Galway (IE); Denise Zarins, Saratoga, CA (US); Mark Gelfand, New York, NY (US); Mark S. Leung, Duncan (CA)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 290 days.

(21) Appl. No.: 14/799,743

(22) Filed: Jul. 15, 2015

(65) Prior Publication Data
US 2016/0038212 A1 Feb. 11, 2016

Related U.S. Application Data

(63) Continuation of application No. 13/204,504, filed on Aug. 5, 2011, now abandoned.
(Continued)

(51) Int. Cl.
*A61B 18/02* (2006.01)
*A61B 18/00* (2006.01)

(52) U.S. Cl.
CPC ...... *A61B 18/02* (2013.01); *A61B 2018/0022* (2013.01); *A61B 2018/0212* (2013.01);
(Continued)

(58) Field of Classification Search
CPC ............ A61B 18/02; A61B 2018/0022; A61B 2018/0212; A61B 2018/0262; A61B 2018/0268
See application file for complete search history.

(56) References Cited

U.S. PATENT DOCUMENTS 3,125,096 A 3/1964 Antiles
3,298,371 A 1/1967 Lee
(Continued)

FOREIGN PATENT DOCUMENTS

DE 4406451 9/1995
DE 102005041601 4/2007
(Continued)

OTHER PUBLICATIONS

Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), pp. 232-246.
(Continued)

*Primary Examiner* — Daniel Fowler

(57) ABSTRACT

Catheter apparatuses, systems, and methods for cryogenically modulating neural structures of the renal plexus by intravascular access are disclosed herein. One aspect of the present application, for example, is directed to apparatuses, systems, and methods that incorporate a catheter treatment device comprising an elongated shaft. The elongated shaft is sized and configured to deliver a cryo-applicator to a renal artery via an intravascular path. Cryogenic renal neuromodulation may be achieved via application of cryogenic
(Continued)

temperatures to modulate neural fibers that contribute to renal function, or of vascular structures that feed or perfuse the neural fibers.

16 Claims, 46 Drawing Sheets

Related U.S. Application Data

(60) Provisional application No. 61/371,110, filed on Aug. 5, 2010, provisional application No. 61/406,968, filed on Oct. 26, 2010.

(52) U.S. Cl.
CPC ................ *A61B 2018/0262* (2013.01); *A61B 2018/0268* (2013.01)

(56) References Cited

U.S. PATENT DOCUMENTS

| | | | |
|---|---|---|---|
| 3,901,241 A | 8/1975 | Allen, Jr. | |
| 3,924,628 A | 12/1975 | Droegemueller et al. | |
| 4,018,227 A | 4/1977 | Wallach | |
| 4,275,734 A | 6/1981 | Mitchiner | |
| 4,483,341 A | 11/1984 | Witteles | |
| 4,602,624 A | 7/1986 | Naples et al. | |
| 4,649,936 A | 3/1987 | Ungar et al. | |
| 4,709,698 A | 12/1987 | Johnston et al. | |
| 4,764,504 A | 8/1988 | Johnson et al. | |
| 4,890,623 A | 1/1990 | Cook et al. | |
| 4,976,711 A | 12/1990 | Parins et al. | |
| 5,108,390 A | 4/1992 | Potocky et al. | |
| 5,151,100 A * | 9/1992 | Abele .................. | A61B 18/08 606/28 |
| 5,190,539 A | 3/1993 | Fletcher et al. | |
| 5,300,068 A | 4/1994 | Rosar et al. | |
| 5,308,323 A | 5/1994 | Sogawa et al. | |
| 5,334,181 A | 8/1994 | Rubinsky et al. | |
| 5,342,301 A | 8/1994 | Saab | |
| 5,358,514 A | 10/1994 | Schulman et al. | |
| 5,368,591 A | 11/1994 | Lennox et al. | |
| 5,383,856 A | 1/1995 | Bersin | |
| 5,417,355 A | 5/1995 | Broussalian et al. | |
| 5,423,744 A | 6/1995 | Gencheff et al. | |
| 5,425,364 A | 6/1995 | Imran | |
| 5,484,400 A | 1/1996 | Edwards et al. | |
| 5,571,147 A | 11/1996 | Sluijter et al. | |
| 5,588,964 A | 12/1996 | Imran et al. | |
| 5,599,345 A | 2/1997 | Edwards et al. | |
| 5,624,392 A | 4/1997 | Saab | |
| 5,626,576 A | 5/1997 | Janssen | |
| 5,672,174 A | 9/1997 | Gough et al. | |
| 5,688,266 A | 11/1997 | Edwards et al. | |
| 5,700,282 A | 12/1997 | Zabara | |
| 5,707,400 A | 1/1998 | Terry, Jr. et al. | |
| 5,741,248 A | 4/1998 | Stern et al. | |
| 5,758,505 A | 6/1998 | Dobak, III et al. | |
| 5,772,590 A | 6/1998 | Webster, Jr. | |
| 5,807,391 A | 9/1998 | Wijkamp | |
| 5,837,003 A | 11/1998 | Ginsburg | |
| 5,860,970 A | 1/1999 | Goddard et al. | |
| 5,860,974 A | 1/1999 | Abele | |
| 5,865,787 A | 2/1999 | Shapland et al. | |
| 5,868,735 A | 2/1999 | Lafontaine | |
| 5,893,885 A | 4/1999 | Webster et al. | |
| 5,902,299 A | 5/1999 | Jayaraman | |
| 5,944,710 A | 8/1999 | Dev et al. | |
| 5,954,719 A | 9/1999 | Chen et al. | |
| 5,971,979 A | 10/1999 | Joye et al. | |
| 5,983,141 A | 11/1999 | Sluijter et al. | |
| 6,004,269 A | 12/1999 | Crowley et al. | |
| 6,009,877 A | 1/2000 | Edwards | |
| 6,012,457 A | 1/2000 | Lesh | |
| 6,024,740 A | 2/2000 | Lesh | |
| 6,024,752 A | 2/2000 | Horn et al. | |
| 6,032,675 A | 3/2000 | Rubinsky | |
| 6,036,687 A | 3/2000 | Laufer et al. | |
| 6,056,744 A | 5/2000 | Edwards | |
| 6,066,134 A | 5/2000 | Eggers et al. | |
| 6,091,995 A | 7/2000 | Ingle et al. | |
| 6,099,524 A | 8/2000 | Lipson et al. | |
| 6,117,101 A | 9/2000 | Diederich et al. | |
| 6,135,999 A | 10/2000 | Fanton et al. | |
| 6,142,991 A | 11/2000 | Schatzberger | |
| 6,142,993 A | 11/2000 | Whayne et al. | |
| 6,149,620 A | 11/2000 | Baker et al. | |
| 6,151,245 A | 11/2000 | Pio et al. | |
| 6,161,048 A | 12/2000 | Sluijter et al. | |
| 6,161,049 A | 12/2000 | Rudie et al. | |
| 6,161,543 A | 12/2000 | Cox et al. | |
| 6,164,283 A | 12/2000 | Lesh | |
| 6,190,356 B1 | 2/2001 | Bersin | |
| 6,219,577 B1 | 4/2001 | Brown, III et al. | |
| 6,224,592 B1 | 5/2001 | Eggers et al. | |
| 6,237,355 B1 | 5/2001 | Li | |
| 6,241,722 B1 | 6/2001 | Dobak et al. | |
| 6,246,912 B1 | 6/2001 | Sluijter et al. | |
| 6,273,886 B1 | 8/2001 | Edwards et al. | |
| 6,283,951 B1 | 9/2001 | Flaherty et al. | |
| 6,283,959 B1 | 9/2001 | Lalonde et al. | |
| 6,290,696 B1 | 9/2001 | Lafontaine | |
| 6,292,695 B1 | 9/2001 | Webster, Jr. et al. | |
| 6,314,325 B1 | 11/2001 | Fitz | |
| 6,322,558 B1 | 11/2001 | Taylor et al. | |
| 6,322,559 B1 | 11/2001 | Daulton et al. | |
| 6,355,029 B1 | 3/2002 | Joye et al. | |
| 6,405,732 B1 | 6/2002 | Edwards et al. | |
| 6,413,255 B1 | 7/2002 | Stern | |
| 6,428,534 B1 | 8/2002 | Joye et al. | |
| 6,432,102 B2 | 8/2002 | Joye et al. | |
| 6,451,045 B1 | 9/2002 | Walker et al. | |
| 6,468,297 B1 | 10/2002 | Williams et al. | |
| 6,488,679 B1 | 12/2002 | Swanson et al. | |
| 6,496,737 B2 | 12/2002 | Rudie et al. | |
| 6,497,703 B1 | 12/2002 | Korteling et al. | |
| 6,506,189 B1 | 1/2003 | Rittman, III et al. | |
| 6,514,226 B1 | 2/2003 | Levin et al. | |
| 6,514,245 B1 | 2/2003 | Williams et al. | |
| 6,517,533 B1 | 2/2003 | Swaminathan | |
| 6,522,926 B1 | 2/2003 | Kieval et al. | |
| 6,527,739 B1 | 3/2003 | Bigus et al. | |
| 6,527,765 B2 | 3/2003 | Kelman et al. | |
| 6,537,271 B1 | 3/2003 | Murray et al. | |
| 6,540,734 B1 | 4/2003 | Chiu et al. | |
| 6,542,781 B1 | 4/2003 | Koblish et al. | |
| 6,551,309 B1 | 4/2003 | LePivert | |
| 6,562,034 B2 | 5/2003 | Edwards et al. | |
| 6,575,933 B1 | 6/2003 | Wittenberger et al. | |
| 6,575,966 B2 | 6/2003 | Lane et al. | |
| 6,602,246 B1 | 8/2003 | Joye et al. | |
| 6,602,247 B2 | 8/2003 | Lalonde | |
| 6,610,083 B2 | 8/2003 | Keller et al. | |
| 6,616,624 B1 | 9/2003 | Kieval | |
| 6,622,731 B2 | 9/2003 | Daniel et al. | |
| 6,635,054 B2 | 10/2003 | Fjield et al. | |
| 6,640,120 B1 | 10/2003 | Swanson et al. | |
| 6,648,878 B2 | 11/2003 | Lafontaine | |
| 6,648,879 B2 | 11/2003 | Joye et al. | |
| 6,666,858 B2 | 12/2003 | Lafontaine | |
| 6,673,066 B2 | 1/2004 | Werneth | |
| 6,685,648 B2 | 2/2004 | Flaherty et al. | |
| 6,685,732 B2 | 2/2004 | Kramer | |
| 6,706,037 B2 | 3/2004 | Zvuloni et al. | |
| 6,709,431 B2 | 3/2004 | Lafontaine | |
| 6,711,444 B2 | 3/2004 | Koblish | |
| 6,736,835 B2 | 5/2004 | Pellegrino et al. | |
| 6,752,805 B2 | 6/2004 | Maguire et al. | |
| 6,755,823 B2 | 6/2004 | Lalonde | |
| 6,786,900 B2 | 9/2004 | Joye et al. | |
| 6,786,901 B2 | 9/2004 | Joye et al. | |
| 6,807,444 B2 | 10/2004 | Tu et al. | |
| 6,811,550 B2 | 11/2004 | Holland et al. | |
| 6,824,543 B2 | 11/2004 | Lentz | |

(56) References Cited

U.S. PATENT DOCUMENTS

| | | |
|---|---|---|
| 6,845,267 B2 | 1/2005 | Harrison et al. |
| 6,850,801 B2 | 2/2005 | Kieval et al. |
| 6,869,431 B2 | 3/2005 | Maguire et al. |
| 6,875,209 B2 | 4/2005 | Zvuloni et al. |
| 6,885,888 B2 | 4/2005 | Rezai |
| 6,893,436 B2 | 5/2005 | Woodard et al. |
| 6,905,510 B2 | 6/2005 | Saab |
| 6,908,462 B2 | 6/2005 | Joye et al. |
| 6,923,808 B2 | 8/2005 | Taimisto |
| 6,929,639 B2 | 8/2005 | Lafontaine |
| 6,939,346 B2 | 9/2005 | Kannenberg et al. |
| 6,949,097 B2 | 9/2005 | Stewart et al. |
| 6,955,174 B2 | 10/2005 | Joye et al. |
| 6,972,015 B2 | 12/2005 | Joye et al. |
| 6,981,382 B2 | 1/2006 | Lentz et al. |
| 6,989,009 B2 | 1/2006 | Lafontaine |
| 7,001,378 B2 | 2/2006 | Yon et al. |
| 7,022,120 B2 | 4/2006 | Lafontaine |
| 7,060,062 B2 | 6/2006 | Joye et al. |
| 7,081,112 B2 | 7/2006 | Joye et al. |
| 7,081,115 B2 | 7/2006 | Taimisto |
| 7,101,368 B2 | 9/2006 | Lafontaine |
| 7,149,574 B2 | 12/2006 | Yun et al. |
| 7,156,840 B2 | 1/2007 | Lentz et al. |
| 7,162,303 B2 | 1/2007 | Levin et al. |
| 7,172,589 B2 | 2/2007 | Lafontaine |
| 7,189,227 B2 | 3/2007 | Lafontaine |
| 7,220,257 B1 | 5/2007 | Lafontaine |
| 7,221,979 B2 | 5/2007 | Zhou et al. |
| 7,288,089 B2 | 10/2007 | Yon et al. |
| 7,300,433 B2 | 11/2007 | Lane et al. |
| 7,306,590 B2 | 12/2007 | Swanson |
| 7,357,797 B2 | 4/2008 | Ryba |
| 7,381,200 B2 | 6/2008 | Katoh et al. |
| 7,387,126 B2 | 6/2008 | Cox et al. |
| 7,390,894 B2 | 6/2008 | Weinshilboum et al. |
| 7,449,018 B2 | 11/2008 | Kramer |
| 7,487,780 B2 | 2/2009 | Hooven |
| 7,507,233 B2 | 3/2009 | Littrup et al. |
| 7,556,624 B2 | 7/2009 | Laufer et al. |
| 7,604,631 B2 | 10/2009 | Reynolds |
| 7,617,005 B2 | 11/2009 | Demarais et al. |
| 7,620,451 B2 | 11/2009 | Demarais et al. |
| 7,641,679 B2 | 1/2010 | Joye et al. |
| 7,647,115 B2 | 1/2010 | Levin et al. |
| 7,653,438 B2 | 1/2010 | Deem et al. |
| 7,717,948 B2 | 5/2010 | Demarais et al. |
| 7,758,571 B2 | 7/2010 | Saadat |
| 7,778,703 B2 | 8/2010 | Gross et al. |
| 7,785,289 B2 | 8/2010 | Rios et al. |
| 7,861,725 B2 | 1/2011 | Swanson |
| 7,972,327 B2 | 7/2011 | Eberl et al. |
| 8,012,147 B2 | 9/2011 | Lafontaine |
| 8,062,289 B2 | 11/2011 | Babaev |
| 8,080,006 B2 | 12/2011 | Lafontaine et al. |
| 8,088,125 B2 | 1/2012 | Lafontaine |
| 8,123,741 B2 | 2/2012 | Marrouche et al. |
| 8,128,617 B2 | 3/2012 | Bencini et al. |
| 8,131,371 B2 | 3/2012 | Demarais et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,175,711 B2 | 5/2012 | Demarais et al. |
| 8,187,261 B2 | 5/2012 | Watson |
| 8,298,217 B2 | 10/2012 | Lane et al. |
| 8,439,909 B2 | 5/2013 | Wang et al. |
| 8,469,919 B2 | 6/2013 | Ingle et al. |
| 8,473,067 B2 | 6/2013 | Hastings et al. |
| 8,475,441 B2 | 7/2013 | Babkin et al. |
| 8,480,663 B2 | 7/2013 | Ingle et al. |
| 8,480,664 B2 | 7/2013 | Watson et al. |
| 8,663,211 B2 | 3/2014 | Fourkas et al. |
| 8,740,895 B2 | 6/2014 | Mayse et al. |
| 8,777,943 B2 | 7/2014 | Mayse et al. |
| 9,101,343 B2 | 8/2015 | Duong et al. |
| 9,402,676 B2 | 8/2016 | Babkin et al. |
| 2002/0007180 A1 | 1/2002 | Wittenberger et al. |
| 2002/0026182 A1 | 2/2002 | Joye et al. |
| 2002/0045893 A1 | 4/2002 | Lane et al. |
| 2002/0087208 A1 | 7/2002 | Koblish et al. |
| 2002/0107515 A1 | 8/2002 | Edwards et al. |
| 2002/0120258 A1 | 8/2002 | Lalonde |
| 2002/0139379 A1 | 10/2002 | Edwards et al. |
| 2002/0165532 A1 | 11/2002 | Hill et al. |
| 2002/0183682 A1 | 12/2002 | Darvish et al. |
| 2003/0036752 A1 | 2/2003 | Joye et al. |
| 2003/0050635 A1 | 3/2003 | Truckai et al. |
| 2003/0050681 A1 | 3/2003 | Pianca et al. |
| 2003/0060762 A1 | 3/2003 | Zvuloni et al. |
| 2003/0060858 A1 | 3/2003 | Kieval et al. |
| 2003/0074039 A1 | 4/2003 | Puskas |
| 2003/0088189 A1 | 5/2003 | Tu et al. |
| 2003/0088240 A1 | 5/2003 | Saadat |
| 2003/0125790 A1 | 7/2003 | Fastovsky et al. |
| 2003/0181897 A1 | 9/2003 | Thomas et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0024392 A1 | 2/2004 | Lewis et al. |
| 2004/0034344 A1 | 2/2004 | Ryba |
| 2004/0215186 A1 | 10/2004 | Cornelius et al. |
| 2004/0243119 A1 | 12/2004 | Lane et al. |
| 2004/0254528 A1 | 12/2004 | Adams et al. |
| 2004/0267250 A1 | 12/2004 | Yon et al. |
| 2005/0080409 A1 | 4/2005 | Young et al. |
| 2005/0096647 A1 | 5/2005 | Steinke et al. |
| 2005/0187579 A1 | 8/2005 | Danek et al. |
| 2005/0209587 A1 | 9/2005 | Joye et al. |
| 2005/0228460 A1 | 10/2005 | Levin et al. |
| 2005/0240117 A1 | 10/2005 | Zvuloni et al. |
| 2006/0030843 A1 | 2/2006 | Lane et al. |
| 2006/0084962 A1 | 4/2006 | Joye et al. |
| 2006/0085054 A1 | 4/2006 | Zikorus et al. |
| 2006/0095029 A1 | 5/2006 | Young et al. |
| 2006/0100618 A1 | 5/2006 | Chan et al. |
| 2006/0206150 A1 | 9/2006 | Demarais et al. |
| 2006/0212027 A1 | 9/2006 | Marrouche et al. |
| 2006/0212076 A1 | 9/2006 | Demarais et al. |
| 2006/0247611 A1 | 11/2006 | Abboud et al. |
| 2006/0271111 A1 | 11/2006 | Demarais et al. |
| 2007/0049924 A1 | 3/2007 | Rahn |
| 2007/0093710 A1 | 4/2007 | Maschke |
| 2007/0129720 A1 | 6/2007 | Demarais et al. |
| 2007/0185445 A1 | 8/2007 | Nahon et al. |
| 2007/0265687 A1 | 11/2007 | Deem et al. |
| 2007/0299433 A1 | 12/2007 | Williams et al. |
| 2008/0009851 A1 | 1/2008 | Wittenberger et al. |
| 2008/0097251 A1 | 4/2008 | Babaev |
| 2008/0171974 A1 | 7/2008 | Lafontaine et al. |
| 2008/0208182 A1 | 8/2008 | Lafontaine et al. |
| 2008/0300584 A1 | 12/2008 | Lentz et al. |
| 2008/0306475 A1 | 12/2008 | Lentz et al. |
| 2008/0312644 A1 | 12/2008 | Fourkas et al. |
| 2008/0319513 A1 | 12/2008 | Pu et al. |
| 2009/0036948 A1 | 2/2009 | Levin et al. |
| 2009/0171333 A1 | 7/2009 | Hon |
| 2009/0182316 A1 | 7/2009 | Bencini |
| 2009/0182317 A1 | 7/2009 | Bencini |
| 2009/0182319 A1 | 7/2009 | Lane et al. |
| 2009/0209949 A1 | 8/2009 | Ingle et al. |
| 2009/0221955 A1 | 9/2009 | Babaev |
| 2009/0281533 A1 | 11/2009 | Ingle et al. |
| 2009/0287202 A1 | 11/2009 | Ingle et al. |
| 2009/0299355 A1 | 12/2009 | Bencini et al. |
| 2010/0049184 A1 | 2/2010 | George et al. |
| 2010/0069900 A1 | 3/2010 | Shirley et al. |
| 2010/0100087 A1 | 4/2010 | Mazzone et al. |
| 2010/0106148 A1 | 4/2010 | Joye et al. |
| 2010/0114269 A1 | 5/2010 | Wittenberger et al. |

(56) References Cited

U.S. PATENT DOCUMENTS

| | | |
|---|---|---|
| 2010/0125266 A1 | 5/2010 | Deem et al. |
| 2010/0130970 A1 | 5/2010 | Williams et al. |
| 2010/0137860 A1 | 6/2010 | Demarais et al. |
| 2010/0137952 A1 | 6/2010 | Demarais et al. |
| 2010/0179526 A1 | 7/2010 | Lawrence |
| 2010/0179527 A1 | 7/2010 | Watson et al. |
| 2010/0191112 A1 | 7/2010 | Demarais et al. |
| 2010/0191231 A1 | 7/2010 | Heberer |
| 2010/0198203 A1 | 8/2010 | Kuck et al. |
| 2010/0222786 A1 | 9/2010 | Kassab |
| 2010/0222851 A1 | 9/2010 | Deem et al. |
| 2010/0222854 A1 | 9/2010 | Demarais et al. |
| 2010/0234838 A1 | 9/2010 | Watson |
| 2010/0249766 A1 | 9/2010 | Saadat |
| 2010/0256621 A1 | 10/2010 | Babkin et al. |
| 2010/0280507 A1 | 11/2010 | Babkin et al. |
| 2011/0125143 A1 | 5/2011 | Gross et al. |
| 2011/0152855 A1 | 6/2011 | Mayse et al. |
| 2011/0257642 A1 | 10/2011 | Griggs |
| 2011/0263921 A1 | 10/2011 | Vrba et al. |
| 2011/0270238 A1 | 11/2011 | Rizq et al. |
| 2011/0282272 A1 | 11/2011 | Lafontaine |
| 2012/0029509 A1 | 2/2012 | Smith |
| 2012/0029511 A1 | 2/2012 | Smith et al. |
| 2012/0089047 A1 | 4/2012 | Ryba et al. |
| 2012/0109021 A1 | 5/2012 | Hastings et al. |
| 2012/0123261 A1 | 5/2012 | Jenson et al. |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136417 A1 | 5/2012 | Buckley et al. |
| 2012/0136418 A1 | 5/2012 | Buckley et al. |
| 2012/0143097 A1 | 6/2012 | Pike, Jr. |
| 2012/0143177 A1 | 6/2012 | Avitall |
| 2012/0143294 A1 | 6/2012 | Clark et al. |
| 2012/0150267 A1 | 6/2012 | Buckley et al. |
| 2012/0158104 A1 | 6/2012 | Huynh et al. |
| 2012/0172837 A1 | 7/2012 | Demarais et al. |
| 2012/0253336 A1 | 10/2012 | Littrup et al. |
| 2013/0090650 A1 | 4/2013 | Jenson et al. |
| 2013/0123770 A1 | 5/2013 | Smith |
| 2013/0184696 A1 | 7/2013 | Fourkas et al. |
| 2013/0345688 A1 | 12/2013 | Babkin et al. |
| 2014/0046313 A1 | 2/2014 | Pederson et al. |
| 2014/0066914 A1 | 3/2014 | Lafontaine |
| 2014/0276724 A1 | 9/2014 | Goshayeshgar |
| 2014/0276728 A1 | 9/2014 | Goshayeshgar |
| 2014/0276811 A1 | 9/2014 | Koblish et al. |
| 2015/0105764 A1 | 4/2015 | Rizq et al. |

FOREIGN PATENT DOCUMENTS

| | | |
|---|---|---|
| EP | 0655225 | 5/1995 |
| EP | 0955012 | 11/1999 |
| EP | 1129670 | 9/2001 |
| EP | 1164963 | 1/2002 |
| EP | 1389477 | 2/2004 |
| EP | 1502553 | 2/2005 |
| EP | 1559362 | 8/2005 |
| EP | 2558016 | 2/2013 |
| EP | 2598070 | 6/2013 |
| EP | 2598071 | 6/2013 |
| EP | 2608837 | 7/2013 |
| GB | 1422535 | 1/1976 |
| GB | 2283678 | 5/1995 |
| GB | 2289414 | 11/1995 |
| SU | 718099 | 2/1980 |
| SU | 1153901 | 5/1985 |
| SU | 1329781 | 8/1987 |
| SU | 1378835 | 3/1988 |
| SU | 1771725 | 10/1992 |
| TW | 372452 | 10/1999 |
| TW | I229246 | 3/2005 |
| WO | WO-9407446 | 4/1994 |
| WO | WO-1995025472 | 9/1995 |
| WO | WO-9531142 | 11/1995 |
| WO | WO-9725011 | 7/1997 |
| WO | WO-1997036548 | 10/1997 |
| WO | WO1998042403 | 10/1998 |
| WO | WO-9900060 | 1/1999 |
| WO | WO-9905979 | 2/1999 |
| WO | WO-9927862 | 6/1999 |
| WO | WO2000047118 | 8/2000 |
| WO | WO-2000047118 | 8/2000 |
| WO | WO-0054684 | 9/2000 |
| WO | WO-2001022897 | 4/2001 |
| WO | WO-0164145 | 9/2001 |
| WO | WO-2001070114 | 9/2001 |
| WO | WO-2002000128 | 1/2002 |
| WO | WO-2002004042 | 1/2002 |
| WO | WO-2002007625 | 1/2002 |
| WO | WO-2002007628 | 1/2002 |
| WO | WO-2002013710 | 2/2002 |
| WO | WO2002015807 | 2/2002 |
| WO | WO-2002015807 | 2/2002 |
| WO | WO-02058576 | 8/2002 |
| WO | WO-2003020334 | 3/2003 |
| WO | WO-2003022167 | 3/2003 |
| WO | WO-2003061496 | 7/2003 |
| WO | WO-2003082080 | 10/2003 |
| WO | WO-2005030072 | 4/2005 |
| WO | WO-2005038357 | 4/2005 |
| WO | WO-2005041748 | 5/2005 |
| WO | WO-2005110528 | 11/2005 |
| WO | WO-2006041881 | 4/2006 |
| WO | WO-2006096272 | 9/2006 |
| WO | WO-2006105121 | 10/2006 |
| WO | WO-2006124177 | 11/2006 |
| WO | WO-2007008954 | 1/2007 |
| WO | WO-2007078997 | 7/2007 |
| WO | WO-2008049084 | 4/2008 |
| WO | WO-2008131037 | 10/2008 |
| WO | WO-2011056684 | 5/2011 |
| WO | WO-2011082278 | 7/2011 |
| WO | WO-2011082279 | 7/2011 |
| WO | WO-2012016135 | 2/2012 |
| WO | WO-2012016137 | 2/2012 |
| WO | WO-2012019156 | 2/2012 |
| WO | WO-2012058153 | 5/2012 |
| WO | WO-2012058156 | 5/2012 |
| WO | WO-2012058158 | 5/2012 |
| WO | WO-2012058159 | 5/2012 |
| WO | WO-2012058160 | 5/2012 |
| WO | WO-2012058161 | 5/2012 |
| WO | WO-2012058163 | 5/2012 |
| WO | WO-2012058165 | 5/2012 |
| WO | WO-2012058167 | 5/2012 |
| WO | WO-2012058430 | 5/2012 |
| WO | WO-2013074683 | 5/2013 |
| WO | WO-2013106859 | 7/2013 |
| WO | WO-2014/150204 | 9/2014 |
| WO | WO-2014/158727 | 10/2014 |
| WO | WO-2014/164445 | 10/2014 |

OTHER PUBLICATIONS

Opposition to European Patent No. 2465470, Granted Oct. 28, 2015, Date of Opposition Jul. 27, 2016, 34 pp.
U.S. Appl. No. 11/363,867, filed Feb. 27, 2006, 70 pp.
U.S. Appl. No. 60/813,589, filed Dec. 29, 2005, 62 pgs.
Ureter, https://en.wikipedia.org/wiki/Ureter, Jun. 2016, 6 pgs.
Remo, Benjamin F. et al., "Safety and Efficacy of Renal Denervation as a Novel Treatment of Ventricular Tachycardia Storm in Patients with Cardiomyopathy." Heart Rhythm, 2014, 11(4), 541-6.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.

(56) References Cited

OTHER PUBLICATIONS

Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Bhandari, A. and Ellias, M., "Loin Pain Hematuria Syndrome: Pain Control with RFA to the Splanchanic Plexus," The Pain Clinc, 2000, vol. 12, No. 4, pp. 323-327.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.
Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011 ;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.

U.S. Appl. No. 95/002,110, filed Aug. 29, 2012, Demarais et al.
U.S. Appl. No. 95/002,209, filed Sep. 13, 2012, Levin et al.
U.S. Appl. No. 95/002,233, filed Sep. 13, 2012, Levin et al.
U.S. Appl. No. 95/002,243, filed Sep. 13, 2012, Levin et al.
U.S. Appl. No. 95/002,253, filed Sep. 13, 2012, Demarais et al.
U.S. Appl. No. 95/002,255, filed Sep. 13, 2012, Demarais et al.
U.S. Appl. No. 95/002,292, filed Sep. 14, 2012, Demarais et al.
U.S. Appl. No. 95/002,327, filed Sep. 14, 2012, Demarais et al.
U.S. Appl. No. 95/002,335, filed Sep. 14, 2012, Demarais et al.
U.S. Appl. No. 95/002,336, filed Sep. 14, 2012, Levin et al.
U.S. Appl. No. 95/002,356, filed Sep. 14, 2012, Demarais et al.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life—Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison Awards$^{TM}$," Edison Awards: Honoring Innovations & Innovators, 2013, 2 pages., <http://www.edisonawards.com/Awards.php>.
"The Future of Renal denervation for the Treatment of Resistant Hypertension." St. Jude Medical, Inc., 2012, 12 pages.
"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.

(56) References Cited

OTHER PUBLICATIONS

Bengel, Frank, "Serial Assessment of Sympathetic Reinnervation After Orthotopic Heart Transplantation: A longitudinal Study Using PET and C-11 Hydroxyephedrine." Circulation, vol. 99, 1999,7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, Jan. 29, 2003, 23 pages.
Gertner, Jon, "Meet the Tech Duo That's Revitalizing the Medical Device Industry." FAST Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery ebolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honor for renal denervation system." The official blog of Medtronic Australasia, Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShot$^{TM}$ renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al. "Catheter ablation of cardiac autonomic nerves for prevention of vagal atrial fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Solis-Herruzo et al., "Effects of lumbar sympathetic block on kidney function in cirrhotic patients with hepatorenal syndrome," J. Hepatol. 5 (1987), pp. 167-173.

(56) References Cited

OTHER PUBLICATIONS

Stella, A., et al., "Effects of reversible renal denervation on haemodynamic and excretory functions on the ipsilateral and contralateral kidney in the cat." Hypertension, 4:181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Schneider, Peter A., "Endovascular Skills—Guidewire and Catheter Skills for Endovascular Surgery," Second Edition Revised and Expanded, 10 pages, (2003).
Kandarpa, Krishna et al., "Handbook of Interventional Radiologic Procedures", Third Edition, pp. 194-210 (2002).
ThermoCool Irrigated Catheter and Integrated Ablation System, Biosense Webster (2006), 6 pages.
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Opposition to European Patent No. EP2092957, Granted Jan. 5, 2011, Date of Opposition Oct. 5, 2011, 26 pages.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Oz, Mehmet, Pressure Relief, TIME, Jan. 9, 2012, 2 pages. <www.time.come/time/printout/0,8816,2103278,00.html>.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Pulmonary Vein Stenosis Following Catheter Ablation of Atrial Fibrillation, Curr. Opin. Cardio. 20: 484-490, 2005.
Papademetriou, Vasilios, Renal Sympathetic Denervation for the Treatment of Difficult-to-Control or Resistant Hypertension, Int. Journal of Hypertension, 2011, 8 pages.
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
U.S. Appl. No. 60/852,787, filed Oct. 18, 2006, 112 pages.
Pieper et al., "Design and Implementation of a New Computerized System for Intraoperative Cardiac Mapping." Journal of Applied Physiology, 1991, vol. 71, No. 4, pp. 1529-1539.
510K Summary of CryoGen Cryosurgery System, filed with FDA Jul. 3, 1997—approved Oct. 1, 1997, 1997, 5 pages.
CO2/Gas Composite Regulator, Sep. 6, 2011, 2 pages. <http://www.genuineinnovations.com/composite-regulator.html>.
CryoGen SS&E: HerOption Uterine Cryoblatin Therapy System, filed with FDA Aug. 15, 2000—approved Apr. 20, 2001,1999, 84 pages.
International Search Report and Written Opinion for International Application No. PCT/US2012/063411 dated Jun. 13, 2013, 13 pages.
Lura Harrison, Ph.D. et al., "Cryosurgical Ablation of the A-V Node-His Bundle—A New Method for Producing A-V Block," Circulation, vol. 55, 1977 pp. 463-470.
Medical Grade Gas Dispenser, Sep. 6, 2011, 1 page, <http://www.abd-inc.com/Frame-904990-page1namepage904990.html?refresh=1205442262133>.
Sesia G. et al., "The use of nitrous oxide as a freezing agent in cryosurgery of the prostate," International Surgery [Int Surg], vol. 53, 1970, pp. 82-90.
Special Order Only Thermal Dilution Injector, Obsolete Product, Sep. 6, 2011, 1 page, <http://www.abd-inc.com/Frame-904990-page1namepage904990.html?refresh=1205442262133>.
Torre, Douglas, MD, "Alternate Cryogens for Cryosurgery," J. Derm. Surgery, Jun. 1975, pp. 56-58.

(56) References Cited

OTHER PUBLICATIONS

Voĭtyna SV, "Cryocatheter-tourniquet," Meditsinskaia Tekhnika [Med Tekh], vol. 6, 1976, pp. 47-48.
International Search Report and Written Opinion for International App. No. PCT/US2011/057511, dated Mar. 16, 2012, 16 pages.
International Search Report and Written Opinion for International Application No. PCT/US2011/046845, dated Dec. 16, 2011, 16 pages.
International Search Report and Written Opinion for International Application No. PCT/US2011/057483, dated Feb. 20, 2012, 11 pages.
International Search Report and Written Opinion for International Application No. PCT/US2011/057490, dated Feb. 23, 2012, 14 pages.
International Search Report and Written Opinion for International Application No. PCT/US2011/057497, dated Feb. 6, 2012, 12 pages.
International Search Report and Written Opinion for International Application No. PCT/US2011/057502, dated Apr. 13, 2012, 14 pages.
International Search report and Written Opinion for International Application No. PCT/US2011/057504, dated Feb. 14, 2012, 12 pages.
International Search Report and Written Opinion for International Application No. PCT/US2011/057514, dated Apr. 12, 2012, 15 pages.
International Search Report and Written Opinion for International Application No. PCT/US2011/057523, dated Mar. 9, 2012, 15 pages.
European Search Report for European Application No. 13159256, dated Oct. 17, 2013, 6 pages.

\* cited by examiner

*Arterial Vasculature*

*Venous Vasculature*

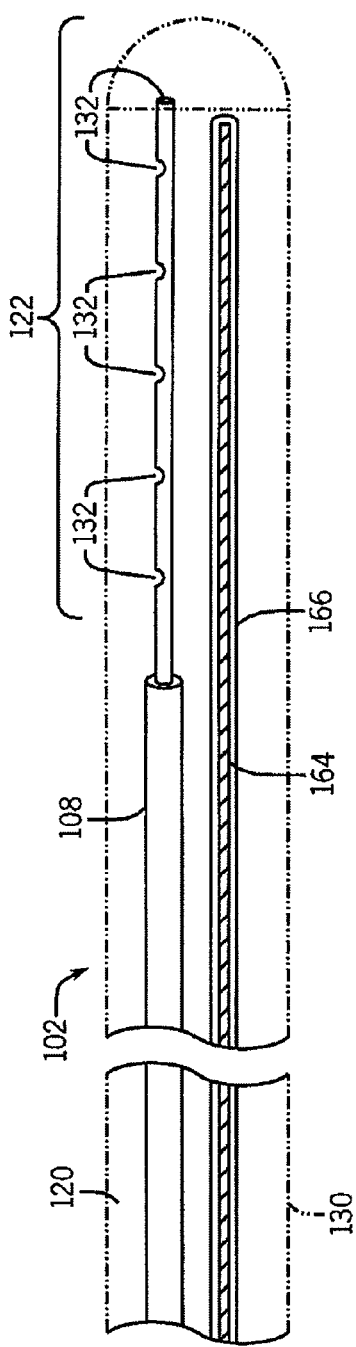
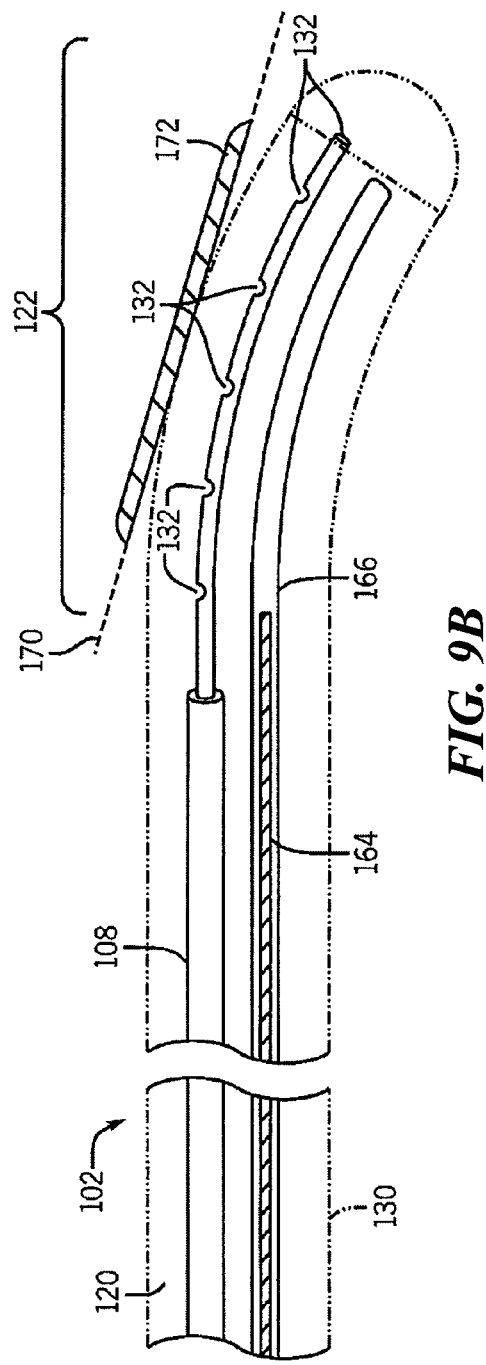
FIG. 9A
FIG. 9B

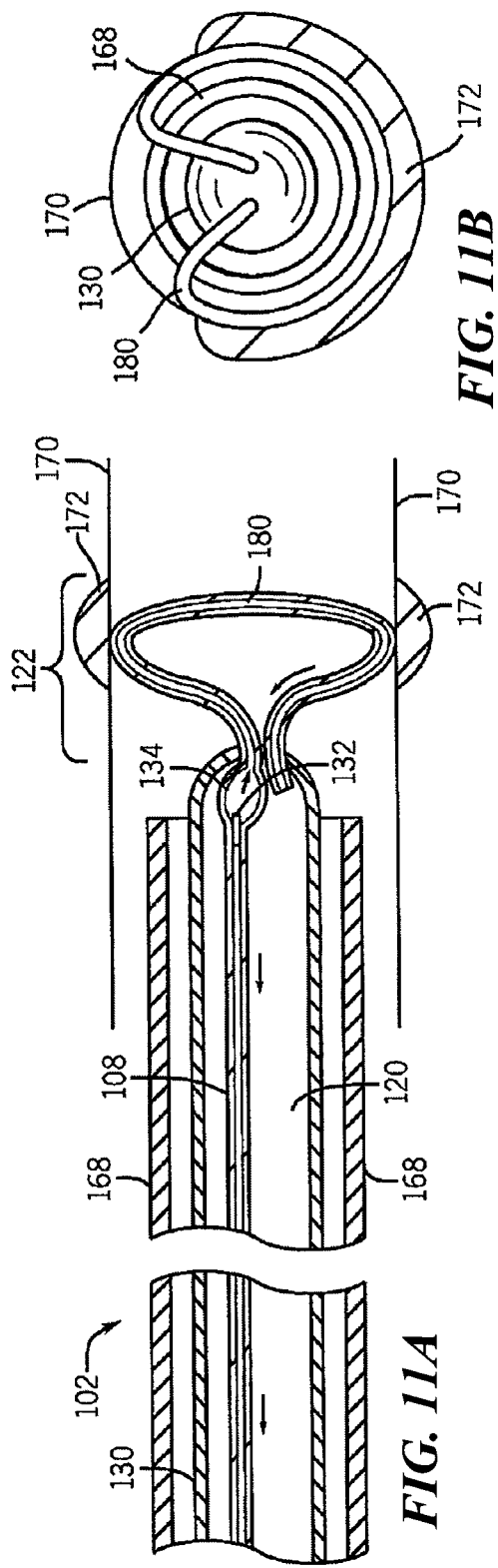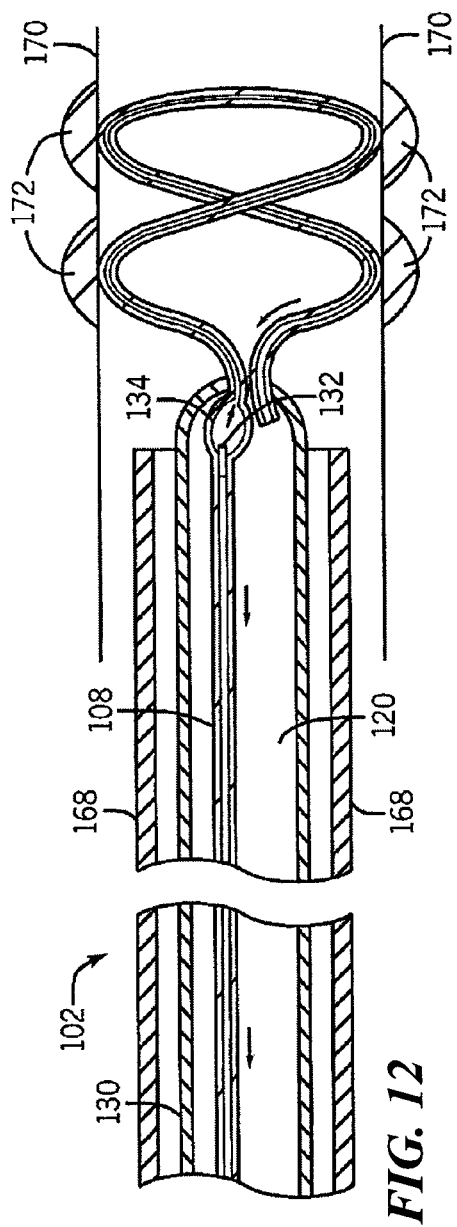
FIG. 11B
FIG. 11A
FIG. 12

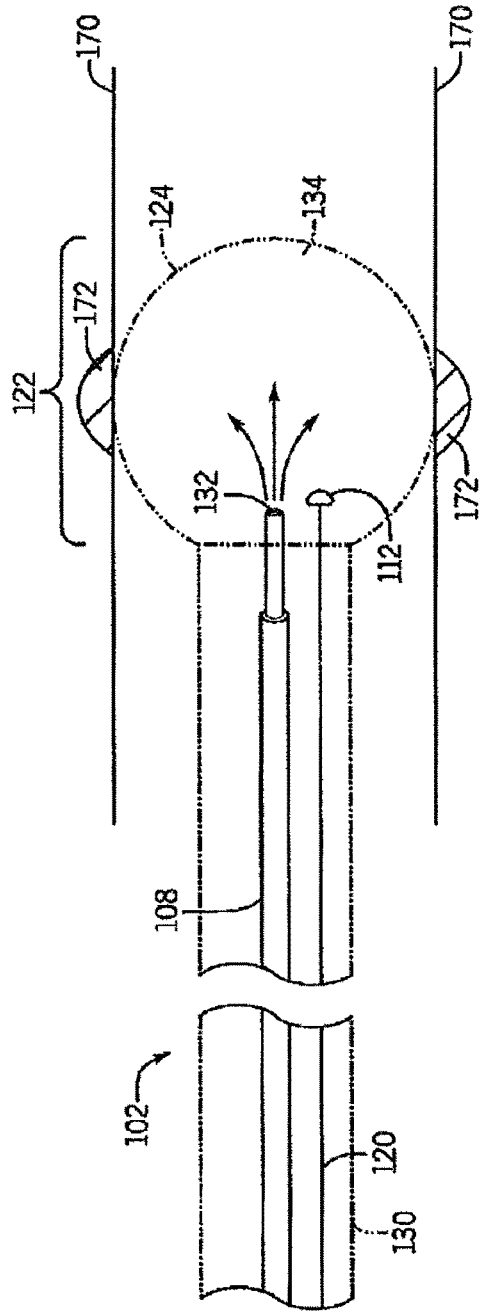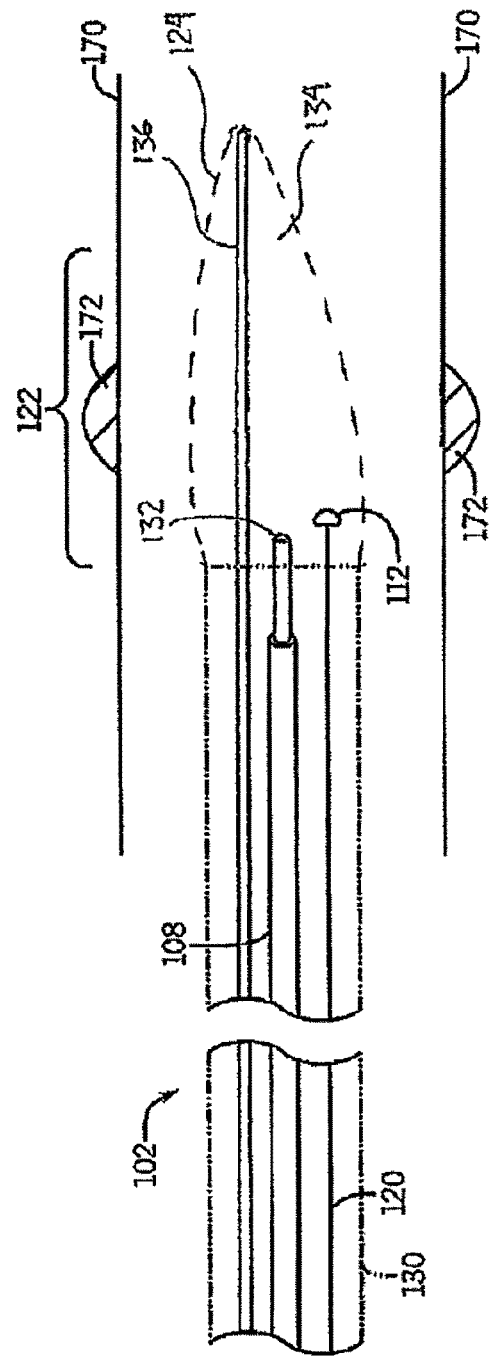
FIG. 13A
FIG. 13B

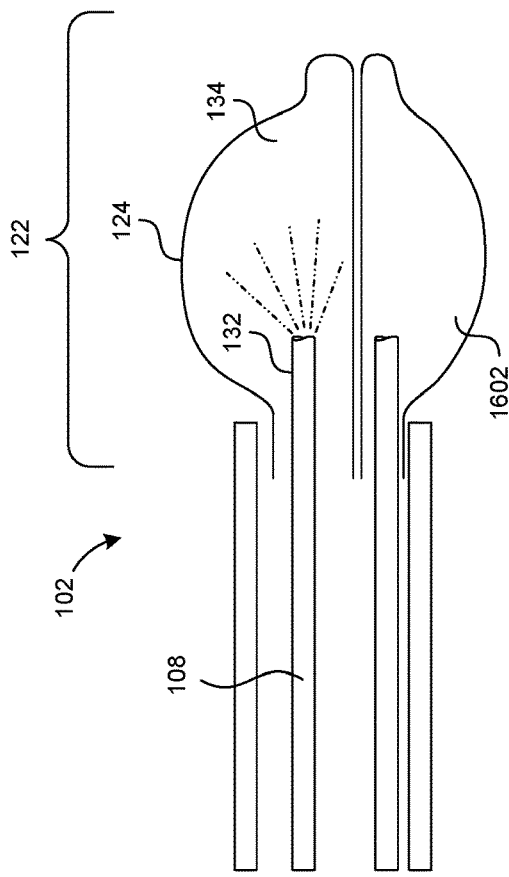
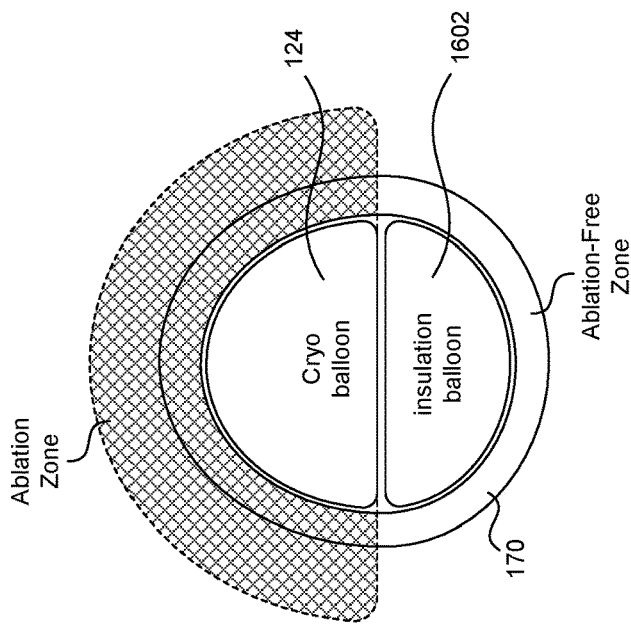
FIG. 16A
FIG. 16B

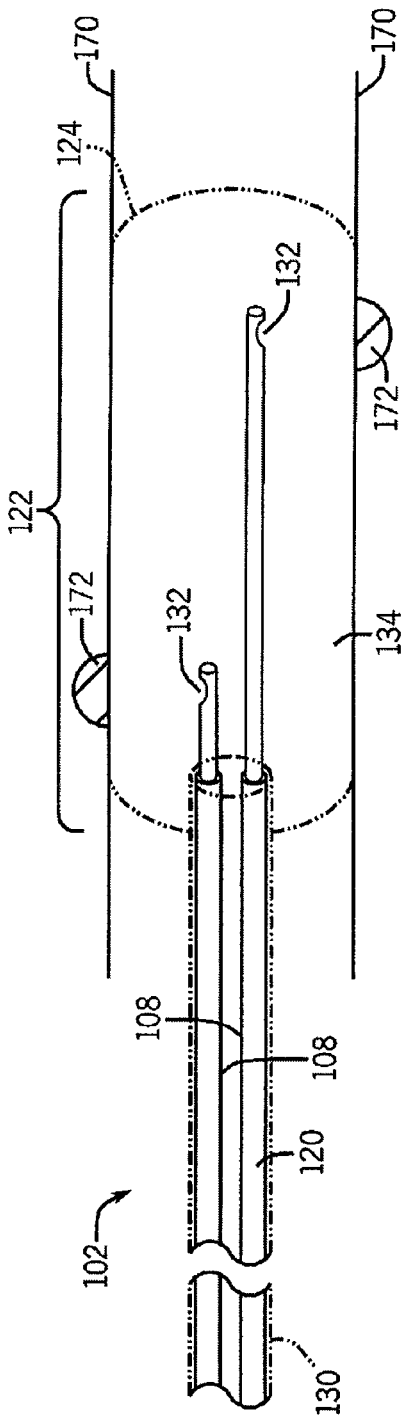
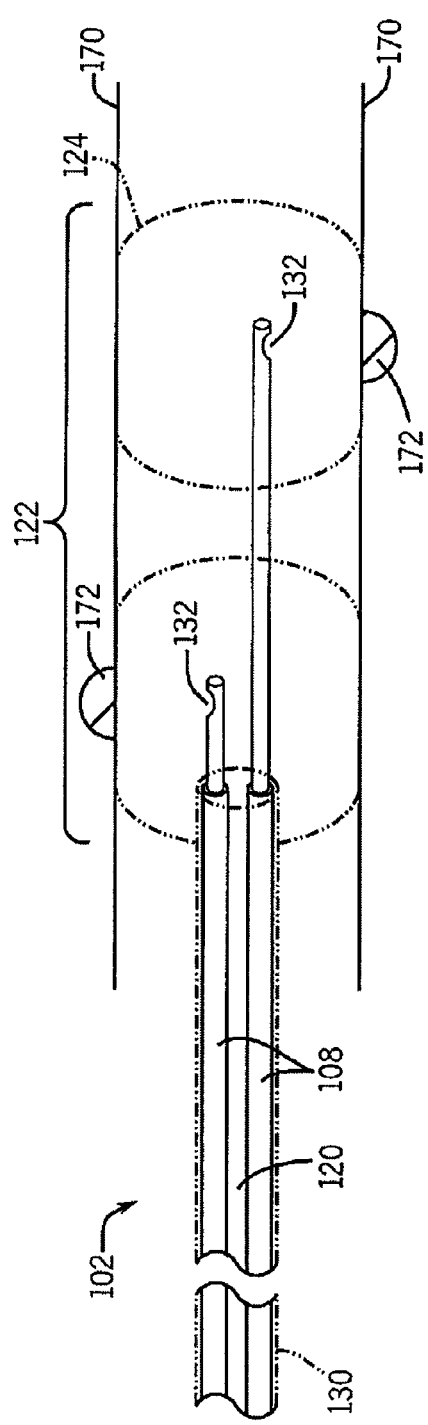
FIG. 22
FIG. 23

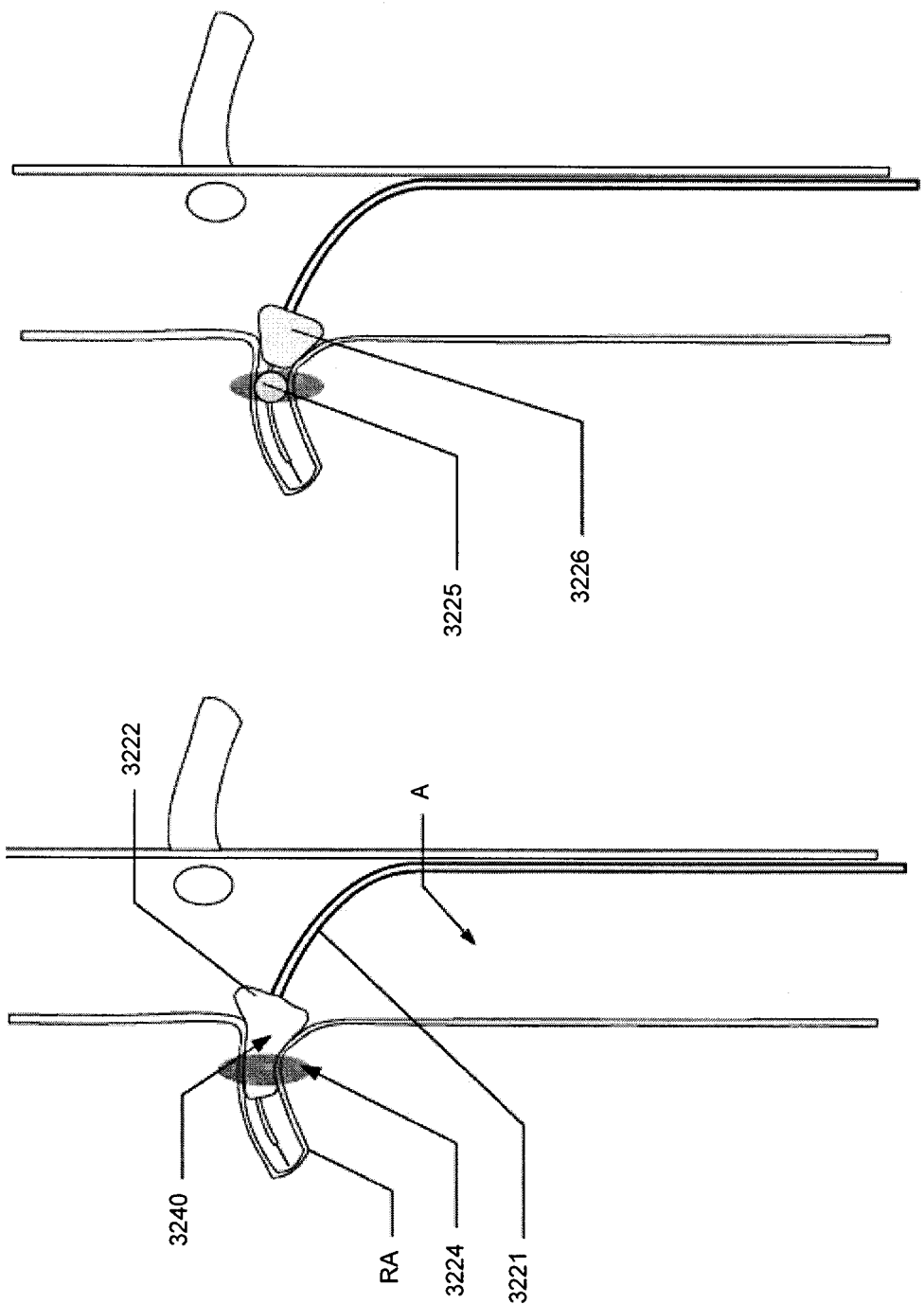

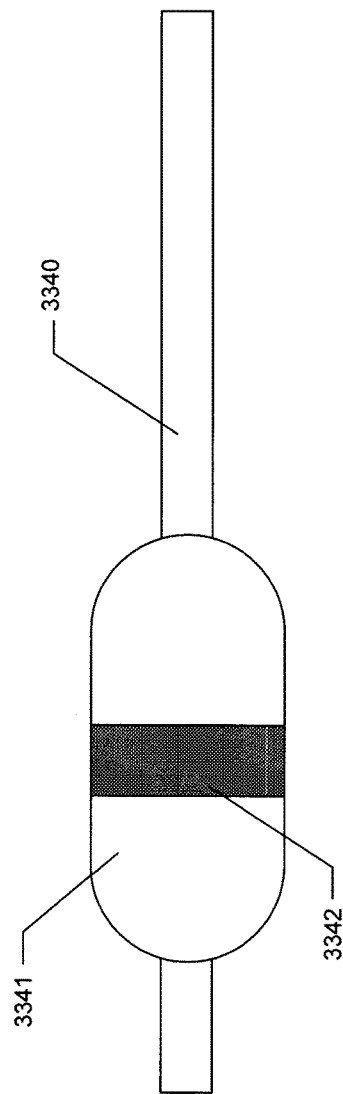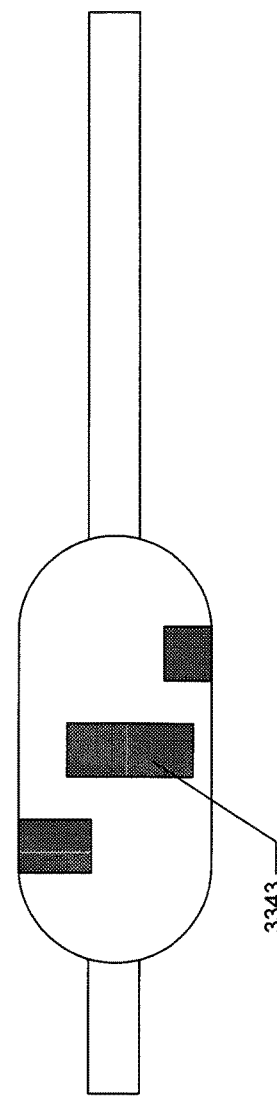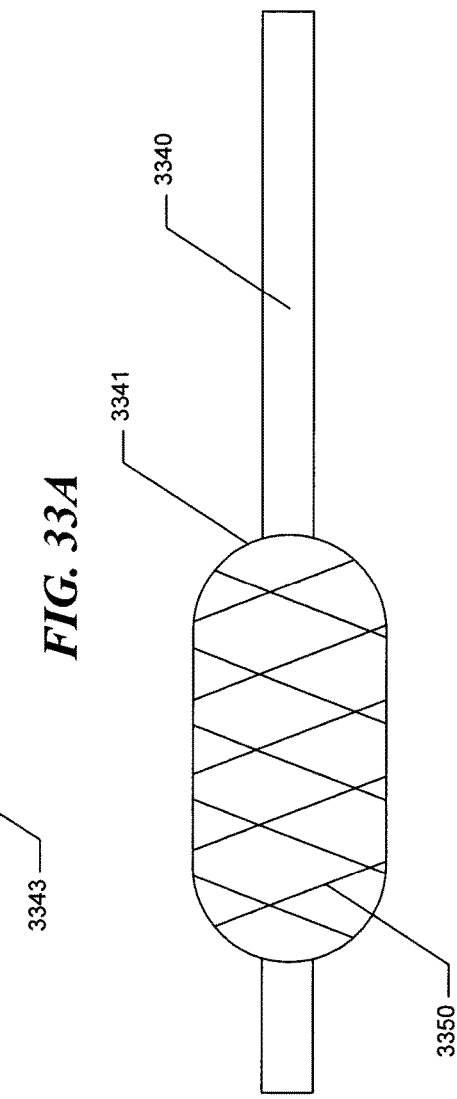
FIG. 33A
FIG. 33B

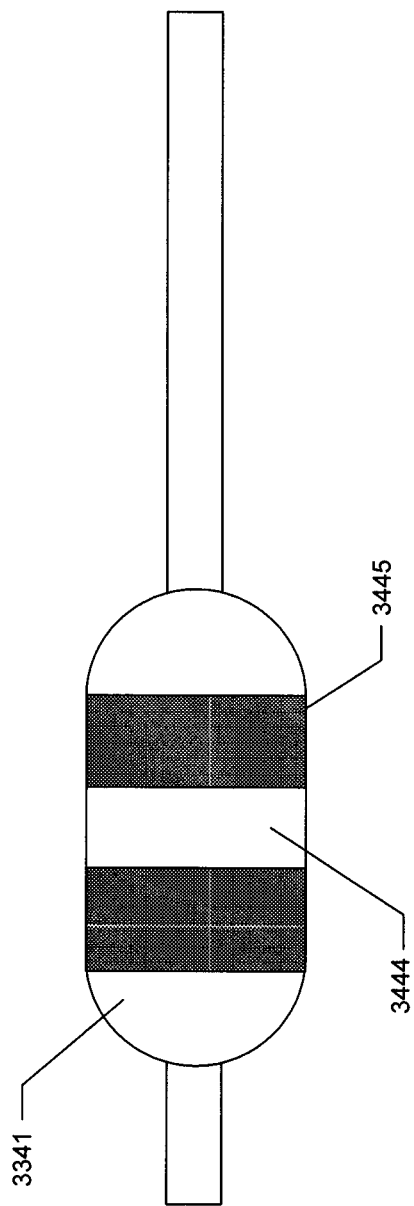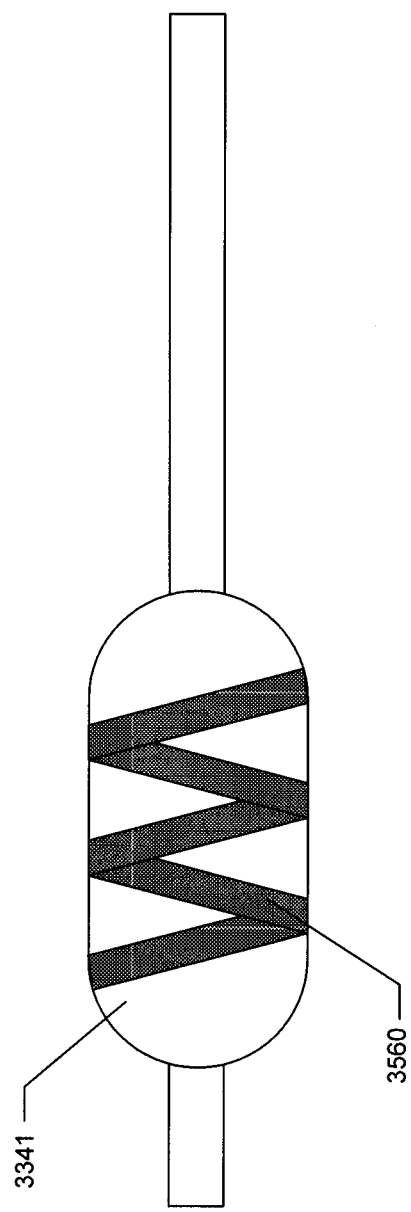

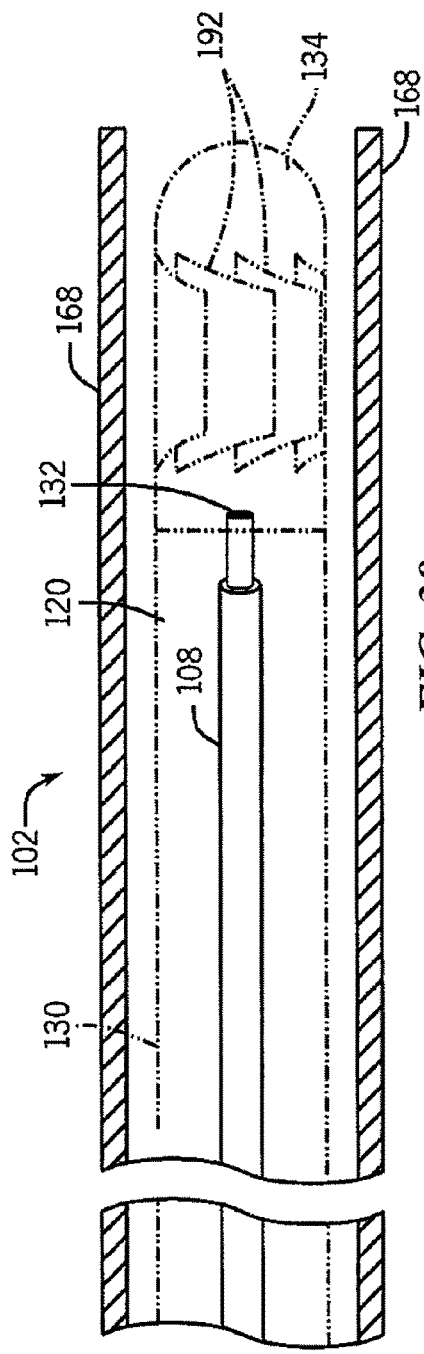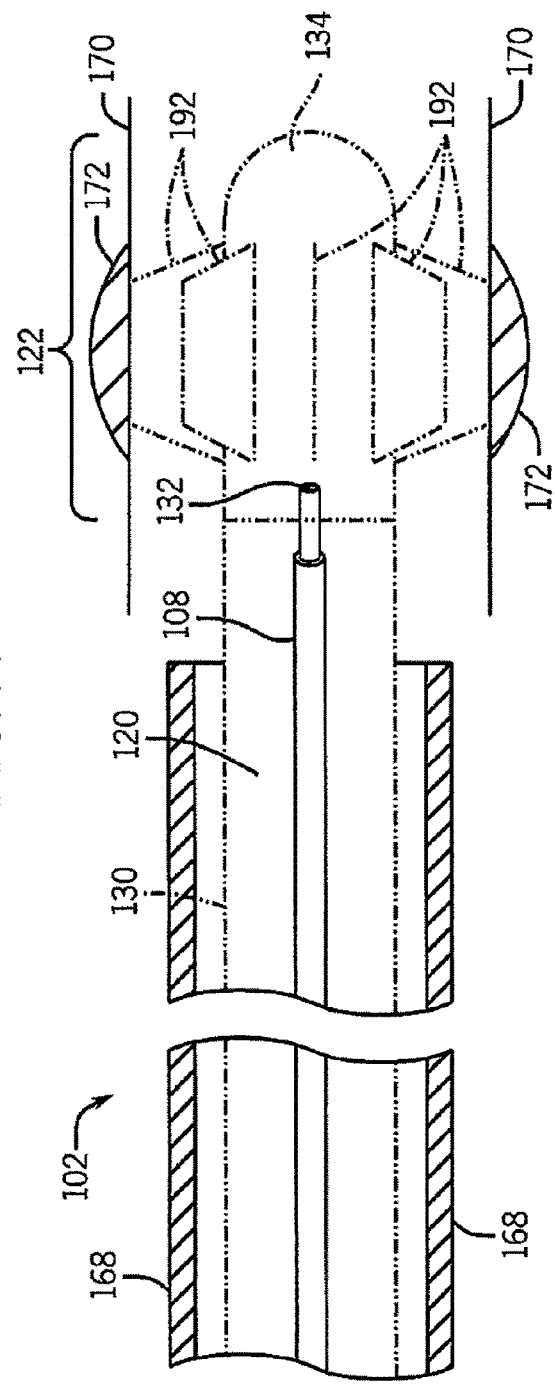

2cm Cold Source Temperature Contours at 120 seconds

CRYOABLATION APPARATUSES, SYSTEMS, AND METHODS FOR RENAL NEUROMODULATION

CROSS-REFERENCE TO RELATED APPLICATION(S)

This application claims the benefit of U.S. Provisional Application No. 61/371,110, filed Aug. 5, 2010, and U.S. Provisional Application No. 61/406,968, filed Oct. 26, 2010. The foregoing applications are incorporated herein by reference in their entireties.

TECHNICAL FIELD

The technologies disclosed in the present application generally relate to apparatuses, systems, and methods for neuromodulation. More particularly, the technologies disclosed herein relate to catheter apparatuses, systems and methods for achieving intravascular renal neuromodulation using cryogenic temperatures.

BACKGROUND

Hypertension, heart failure, chronic kidney disease, insulin resistance, diabetes and metabolic syndrome represent a significant and growing global health issue and, to some extent, may have common underlying physiological causes. Current therapies for these various conditions typically include non-pharmacological, pharmacological and device-based approaches. Despite this variety of treatment options, the rates of control of blood pressure and the therapeutic efforts to prevent progression of these disease states and their sequelae remain unsatisfactory. Although the reasons for this situation are manifold and include issues of non-compliance with prescribed therapy, heterogeneity in responses both in terms of efficacy and adverse event profile, and others, it is evident that alternative options are required to supplement the current therapeutic treatment regimes for these conditions Reduction of sympathetic renal nerve activity (e.g., via neuromodulation, including ablation, of at least a portion of sympathetic renal nerves supplying at least one kidney), can reverse these processes. It may, therefore, be desirable to develop a technology that can achieve renal neuromodulation in a clinically safe and therapeutically effective manner.

SUMMARY

The following summary is provided for the benefit of the reader only, and is not intended to limit the disclosure in any way. The present disclosure relates to apparatuses, systems and methods for endovascular modulation or ablation of renal nerves using cryogenic approaches (i.e., cryomodulation). More specifically, this disclosure describes catheter embodiments using various cryodelivery elements to achieve therapeutic renal neuromodulation from within or adjacent to the renal vasculature of a patient. For example, cryomodulation can be performed using a cryoablation catheter placed in the renal artery or by positioning a cryoprobe in the extravascular space surrounding the renal artery. Additionally, aspects of cryotechnology are disclosed to serve various diagnostic objectives. As used herein, cryomodulation generally means the modulation (i.e., rendering inert or inactive or otherwise completely or partially reducing in function) of renal nerves generally found in and outside the adventitial layer of the renal artery by local freezing of tissue adjacent, in proximity to, and including the renal nerves.

BRIEF DESCRIPTION OF THE DRAWINGS

FIG. 9A is a partially schematic view of one embodiment of a cryo-applicator region suitable for continuous ablations configured in accordance with an aspect of the present disclosure.

FIG. 9B depicts the cryo-applicator region of FIG. 9A in a deployed state.

FIG. 11A is a partially schematic view of one embodiment of a cryo-applicator region in the form of a loop applicator configured in accordance with an aspect of the present disclosure.

FIG. 11B depicts a front view of the loop applicator of FIG. 11A deployed in a vessel.

FIG. 12 is a partially schematic view of another embodiment of a cryo-applicator region in the form of a loop applicator configured in accordance with an aspect of the present disclosure.

FIGS. 13A to 13D are partially schematic views of embodiments of a cryo-applicator region in the form of an occlusive balloon in accordance with an aspect of the present disclosure.

FIG. 14-18B are partially schematic views of further embodiments of cryo-applicator regions including occlusive balloons configured in accordance with aspects of the present disclosure.

FIGS. 20-23 are partially schematic views of embodiments of cryo-applicator regions comprising balloons configured in accordance with aspects of the present disclosure.

FIGS. 24-35B are partially schematic views illustrating additional embodiments of the technology in which the cryo-applicator region includes an inflatable or otherwise expandable cryo-balloon assembly.

FIGS. 36-39 are partially schematic views of embodiments of cryo-applicator regions in the form of expandable metal tips configured in accordance with aspects of the present disclosure.

DETAILED DESCRIPTION

Figure 1:
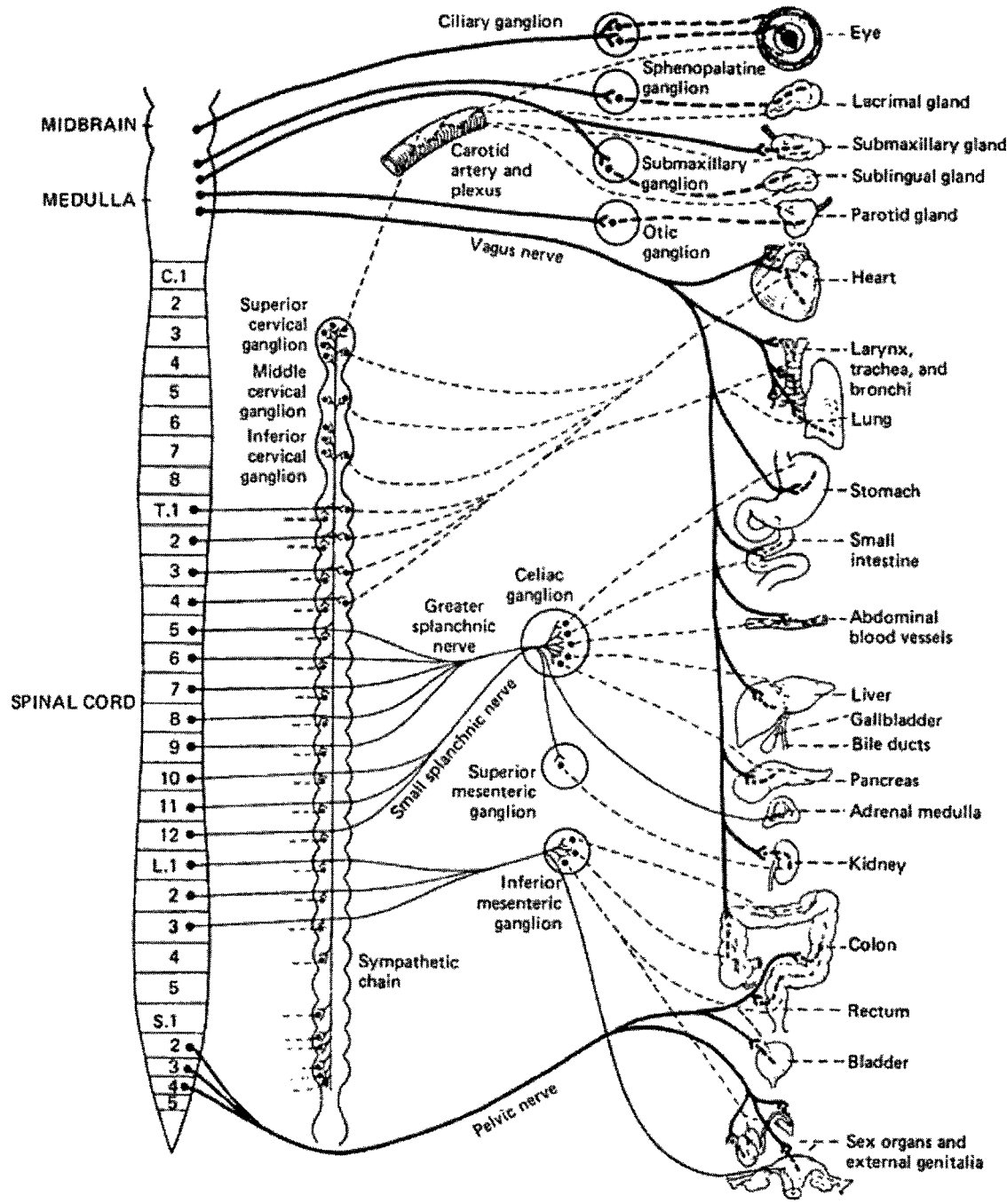
FIG. 1 is a conceptual illustration of the sympathetic nervous system (SNS) and how the brain communicates with the body via the SNS.

Specific details of several embodiments of the technology are described below with reference to FIGS. 1-47. Although many of the embodiments are described below with respect to apparatuses, systems, and methods for endovascular modulation or ablation of renal nerves using cryogenic approaches, other applications and other embodiments in addition to those described herein are within the scope of the technology. Additionally, several other embodiments of the technology can have different configurations, components, or procedures than those described in this section. A person of ordinary skill in the art, therefore, will accordingly understand that the technology may have other embodiments with additional elements, or the technology may have other embodiments without several of the features shown and described below with reference to FIGS. 1-47.

I. Pertinent Anatomy and Physiology

A. The Sympathetic Nervous System

The Sympathetic Nervous System (SNS) is a branch of the autonomic nervous system along with the enteric nervous system and parasympathetic nervous system. It is always active at a basal level (called sympathetic tone) and becomes more active during times of stress. Like other parts of the nervous system, the sympathetic nervous system operates through a series of interconnected neurons. Sympathetic neurons are frequently considered part of the peripheral nervous system (PNS), although many lie within the central nervous system (CNS). Sympathetic neurons of the spinal cord (which is part of the CNS) communicate with peripheral sympathetic neurons via a series of sympathetic ganglia. Within the ganglia, spinal cord sympathetic neurons join peripheral sympathetic neurons through synapses. Spinal cord sympathetic neurons are therefore called presynaptic (or preganglionic) neurons, while peripheral sympathetic neurons are called postsynaptic (or postganglionic) neurons.

At synapses within the sympathetic ganglia, preganglionic sympathetic neurons release acetylcholine, a chemical messenger that binds and activates nicotinic acetylcholine receptors on postganglionic neurons. In response to this stimulus, postganglionic neurons principally release noradrenaline (norepinephrine). Prolonged activation may elicit the release of adrenaline from the adrenal medulla.

Once released, norepinephrine and epinephrine bind adrenergic receptors on peripheral tissues. Binding to adrenergic receptors causes a neuronal and hormonal response. The physiologic manifestations include pupil dilation, increased heart rate, occasional vomiting, and increased blood pressure. Increased sweating is also seen due to binding of cholinergic receptors of the sweat glands.

The sympathetic nervous system is responsible for up- and down-regulating many homeostatic mechanisms in living organisms. Fibers from the SNS innervate tissues in almost every organ system, providing at least some regulatory function to things as diverse as pupil diameter, gut motility, and urinary output. This response is also known as sympatho-adrenal response of the body, as the preganglionic sympathetic fibers that end in the adrenal medulla (but also all other sympathetic fibers) secrete acetylcholine, which activates the secretion of adrenaline (epinephrine) and to a lesser extent noradrenaline (norepinephrine). Therefore, this response that acts primarily on the cardiovascular system is mediated directly via impulses transmitted through the sympathetic nervous system and indirectly via catecholamines secreted from the adrenal medulla.

Science typically looks at the SNS as an automatic regulation system, that is, one that operates without the intervention of conscious thought. Some evolutionary theorists suggest that the sympathetic nervous system operated in early organisms to maintain survival as the sympathetic nervous system is responsible for priming the body for action. One example of this priming is in the moments before waking, in which sympathetic outflow spontaneously increases in preparation for action.

1. The Sympathetic Chain

As shown in FIG. 1, the SNS provides a network of nerves that allows the brain to communicate with the body. Sympathetic nerves originate inside the vertebral column, toward the middle of the spinal cord in the intermediolateral cell column (or lateral horn), beginning at the first thoracic segment of the spinal cord and are thought to extend to the second or third lumbar segments. Because its cells begin in the thoracic and lumbar regions of the spinal cord, the SNS is said to have a thoracolumbar outflow. Axons of these nerves leave the spinal cord through the anterior rootlet/root. They pass near the spinal (sensory) ganglion, where they enter the anterior rami of the spinal nerves. However, unlike somatic innervation, they quickly separate out through white rami connectors which connect to either the paravertebral (which lie near the vertebral column) or prevertebral (which lie near the aortic bifurcation) ganglia extending alongside the spinal column.

In order to reach the target organs and glands, the axons must travel long distances in the body, and, to accomplish this, many axons relay their message to a second cell through synaptic transmission. The ends of the axons link across a space, the synapse, to the dendrites of the second cell. The first cell (the presynaptic cell) sends a neurotransmitter across the synaptic cleft where it activates the second cell (the postsynaptic cell). The message is then carried to the final destination.

In the SNS and other components of the peripheral nervous system, these synapses are made at sites called ganglia. The cell that sends its fiber is called a preganglionic cell, while the cell whose fiber leaves the ganglion is called a postganglionic cell. As mentioned previously, the preganglionic cells of the SNS are located between the first thoracic (T1) segment and third lumbar (L3) segments of the spinal cord. Postganglionic cells have their cell bodies in the ganglia and send their axons to target organs or glands.

The ganglia include not just the sympathetic trunks but also the cervical ganglia (superior, middle and inferior), which sends sympathetic nerve fibers to the head and thorax organs, and the celiac and mesenteric ganglia (which send sympathetic fibers to the gut).

2. Innervation of the Kidneys

Figure 2:
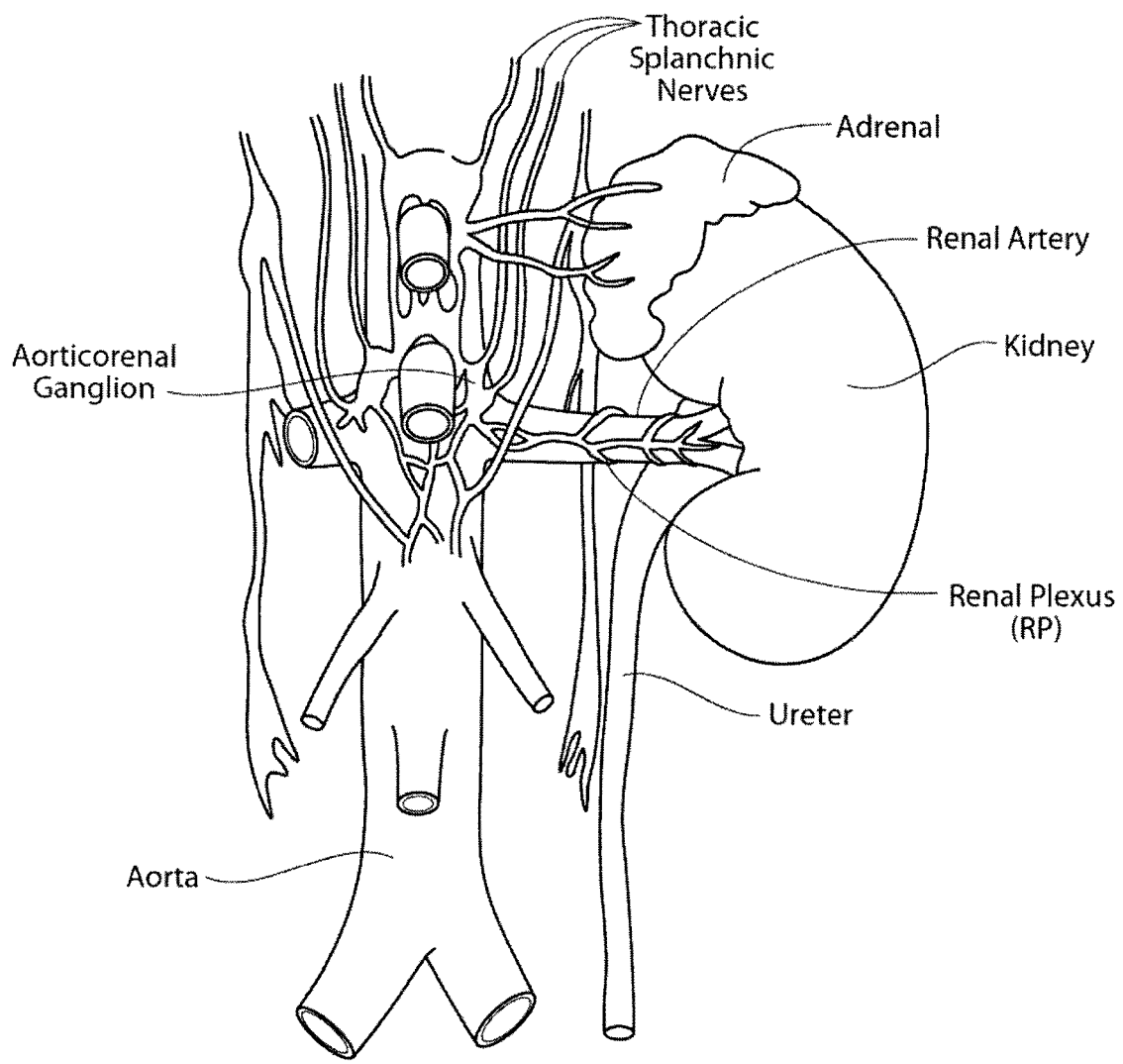
FIG. 2 is an enlarged anatomic view of nerves innervating a left kidney to form the renal plexus surrounding the left renal artery.

As FIG. 2 shows, the kidney is innervated by the renal plexus (RP), which is intimately associated with the renal artery. The renal plexus is an autonomic plexus that surrounds the renal artery and is embedded within the adventitia of the renal artery. The renal plexus extends along the renal artery until it arrives at the substance of the kidney. Fibers contributing to the renal plexus arise from the celiac ganglion, the superior mesenteric ganglion, the aorticorenal ganglion and the aortic plexus. The renal plexus (RP), also referred to as the renal nerve, is predominantly comprised of sympathetic components. There is no (or at least very minimal) parasympathetic innervation of the kidney.

Preganglionic neuronal cell bodies are located in the intermediolateral cell column of the spinal cord. Preganglionic axons pass through the paravertebral ganglia (they do not synapse) to become the lesser splanchnic nerve, the least splanchnic nerve, first lumbar splanchnic nerve, second lumbar splanchnic nerve, and travel to the celiac ganglion, the superior mesenteric ganglion, and the aorticorenal ganglion. Postganglionic neuronal cell bodies exit the celiac ganglion, the superior mesenteric ganglion, and the aorticorenal ganglion to the renal plexus (RP) and are distributed to the renal vasculature.

3. Renal Sympathetic Neural Activity

Messages travel through the SNS in a bidirectional flow. Efferent messages may trigger changes in different parts of the body simultaneously. For example, the sympathetic nervous system may accelerate heart rate; widen bronchial passages; decrease motility (movement) of the large intestine; constrict blood vessels; increase peristalsis in the esophagus; cause pupil dilation, piloerection (goose bumps) and perspiration (sweating); and raise blood pressure. Afferent messages carry signals from various organs and sensory receptors in the body to other organs and, particularly, the brain.

Hypertension, heart failure and chronic kidney disease are a few of many disease states that result from chronic activation of the SNS, especially the renal sympathetic nervous system. Chronic activation of the SNS is a maladaptive response that drives the progression of these disease states. Pharmaceutical management of the renin-angiotensin-aldosterone system (RAAS) has been a longstanding, but somewhat ineffective, approach for reducing over-activity of the SNS.

As mentioned above, the renal sympathetic nervous system has been identified as a major contributor to the complex pathophysiology of hypertension, states of volume overload (such as heart failure), and progressive renal disease, both experimentally and in humans. Studies employing radiotracer dilution methodology to measure overflow of norepinephrine from the kidneys to plasma revealed increased renal norepinephrine (NE) spillover rates in patients with essential hypertension, particularly so in young hypertensive subjects, which in concert with increased NE spillover from the heart, is consistent with the hemodynamic profile typically seen in early hypertension and characterized by an increased heart rate, cardiac output and renovascular resistance. It is now known that essential hypertension is commonly neurogenic, often accompanied by pronounced sympathetic nervous system overactivity.

Activation of cardiorenal sympathetic nerve activity is even more pronounced in heart failure, as demonstrated by an exaggerated increase of NE overflow from the heart and the kidneys to plasma in this patient group. In line with this notion is the recent demonstration of a strong negative predictive value of renal sympathetic activation on all-cause mortality and heart transplantation in patients with congestive heart failure, which is independent of overall sympathetic activity, glomerular filtration rate and left ventricular ejection fraction. These findings support the notion that treatment regimens that are designed to reduce renal sympathetic stimulation have the potential to improve survival in patients with heart failure.

Both chronic and end stage renal disease are characterized by heightened sympathetic nervous activation. In patients with end stage renal disease, plasma levels of norepinephrine above the median have been demonstrated to be predictive for both all cause death and death from cardiovascular disease. This is also true for patients suffering from diabetic or contrast nephropathy. There is compelling evidence that suggests that sensory afferent signals originating from the diseased kidneys are major contributors to the initiation and sustainment of elevated central sympathetic outflow in this patient group, which facilitates the occurrence of the well known adverse consequences of chronic sympathetic overactivity such as hypertension, left ventricular hypertrophy, ventricular arrhythmias, sudden cardiac death, insulin resistance, diabetes and metabolic syndrome.

(i) Renal Sympathetic Efferent Activity

Sympathetic nerves to the kidneys terminate in the blood vessels, the juxtaglomerular apparatus and the renal tubules. Stimulation of the renal sympathetic nerves causes increased renin release, increased sodium (Na+) reabsorption and a reduction of renal blood flow. These components of the neural regulation of renal function are considerably stimulated in disease states characterized by heightened sympathetic tone and clearly contribute to the rise in blood pressure in hypertensive patients. The reduction of renal blood flow and glomerular filtration rate as a result of renal sympathetic efferent stimulation is likely a cornerstone of the loss of renal function in cardio-renal syndrome, which is renal dysfunction as a progressive complication of chronic heart failure, with a clinical course that typically fluctuates with the patient's clinical status and treatment. Pharmacologic strategies to thwart the consequences of renal efferent sympathetic stimulation include centrally acting sympatholytic drugs, beta blockers (intended to reduce renin release), angiotensin converting enzyme inhibitors and receptor blockers (intended to block the action of angiotensin II and aldosterone activation consequent to renin release) and diuretics (intended to counter the renal sympathetic mediated sodium and water retention). However, the current pharmacologic strategies have significant limitations including limited efficacy, compliance issues, side effects and others.

(ii) Renal Sensory Afferent Nerve Activity

Figure 3A:
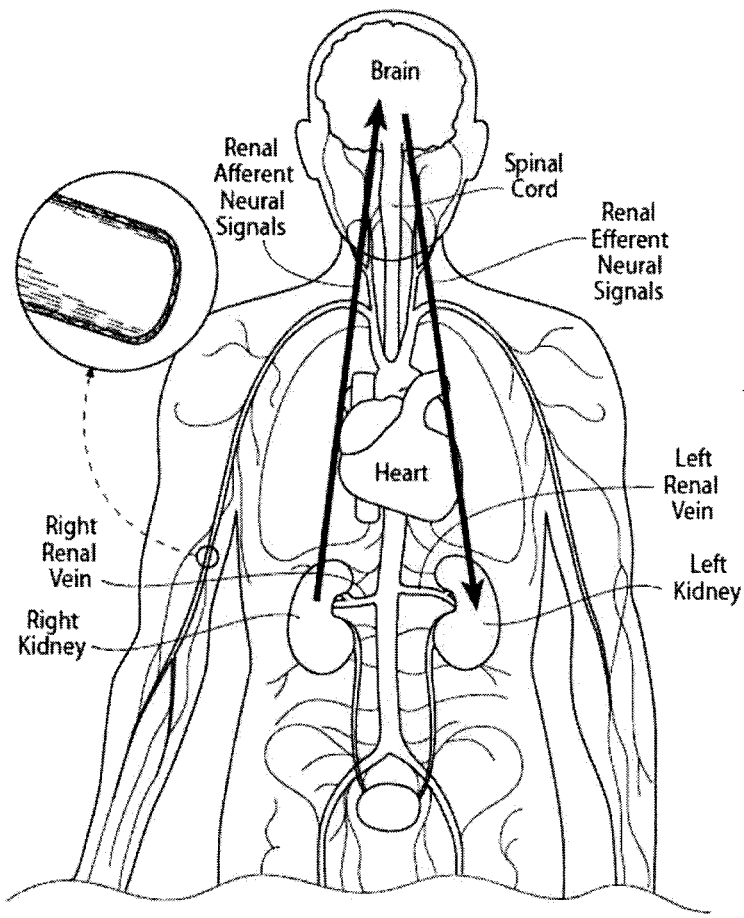
FIGS. 3A and 3B provide anatomic and conceptual views of a human body, respectively, depicting neural efferent and afferent communication between the brain and kidneys.
Figure 3B:
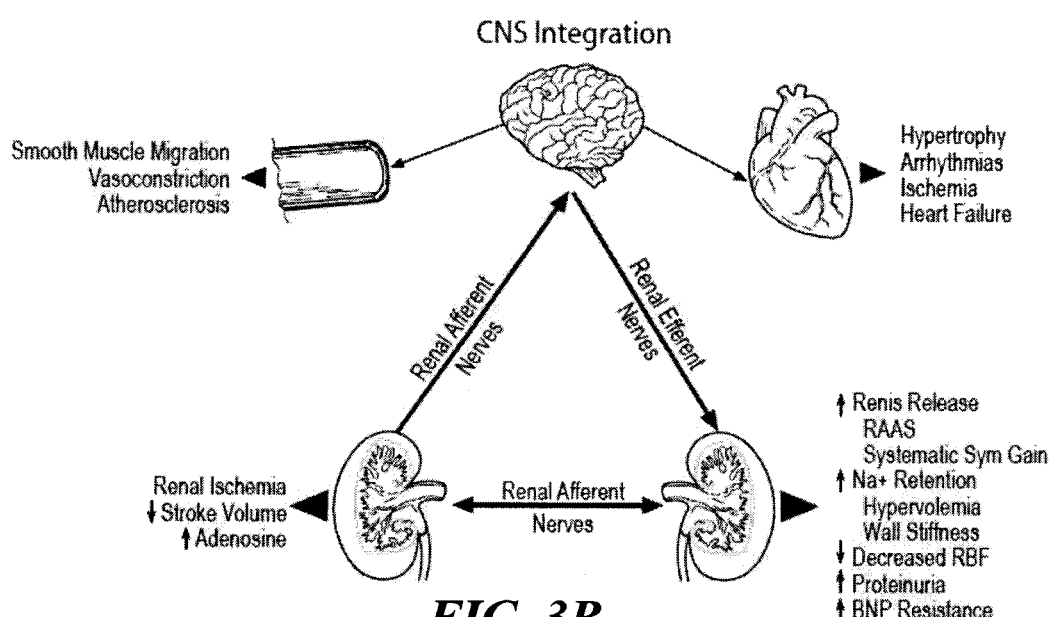

The kidneys communicate with integral structures in the central nervous system via renal sensory afferent nerves. Several forms of "renal injury" may induce activation of sensory afferent signals. For example, renal ischemia, reduction in stroke volume or renal blood flow, or an abundance of adenosine enzyme may trigger activation of afferent neural communication. As shown in FIGS. 3A and 3B, this afferent communication might be from the kidney to the brain or might be from one kidney to the other kidney (via the central nervous system). These afferent signals are centrally integrated and may result in increased sympathetic outflow. This sympathetic drive is directed towards the kidneys, thereby activating the RAAS and inducing increased renin secretion, sodium retention, volume retention and vasoconstriction. Central sympathetic overactivity also impacts other organs and bodily structures innervated by sympathetic nerves such as the heart and the peripheral vasculature, resulting in the described adverse effects of sympathetic activation, several aspects of which also contribute to the rise in blood pressure.

The physiology therefore suggests that (i) denervation of tissue with efferent sympathetic nerves will reduce inappropriate renin release, salt retention, and reduction of renal blood flow, and that (ii) denervation of tissue with afferent sensory nerves will reduce the systemic contribution to hypertension, and other disease states associated with increased central sympathetic tone, through its direct effect on the posterior hypothalamus as well as the contralateral kidney. In addition to the central hypotensive effects of afferent renal denervation, a desirable reduction of central sympathetic outflow to various other sympathetically innervated organs such as the heart and the vasculature is anticipated.

B. Additional Clinical Benefits of Renal Denervation

As provided above, renal denervation is likely to be valuable in the treatment of several clinical conditions characterized by increased overall and particularly renal sympathetic activity such as hypertension, metabolic syndrome, insulin resistance, diabetes, left ventricular hypertrophy, chronic and end stage renal disease, inappropriate fluid retention in heart failure, cardio-renal syndrome and sudden death. Since the reduction of afferent neural signals contributes to the systemic reduction of sympathetic tone/drive, renal denervation might also be useful in treating other conditions associated with systemic sympathetic hyperactivity. Accordingly, renal denervation may also benefit other organs and bodily structures innervated by sympathetic nerves, including those identified in FIG. 1. For example, a reduction in central sympathetic drive may reduce the insulin resistance that afflicts people with metabolic syndrome and Type II diabetics. Additionally, patients with osteoporosis are also sympathetically activated and might also benefit from the downregulation of sympathetic drive that accompanies renal denervation.

C. Achieving Intravascular Access to the Renal Artery

Figure 4A:
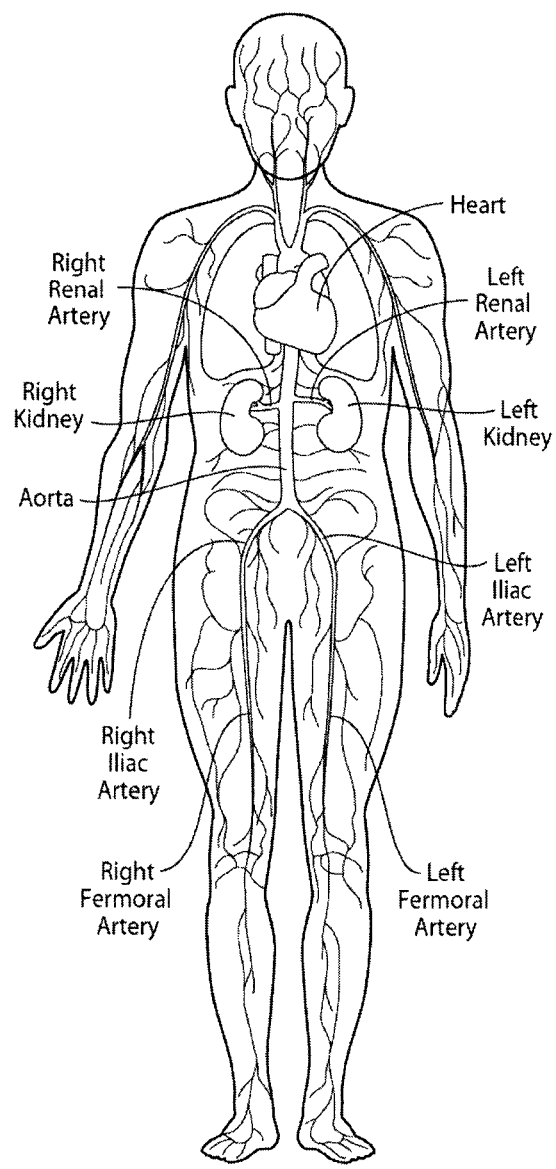
FIGS. 4A and 4B are, respectively, anatomic views of the arterial and venous vasculatures of a human.

In accordance with the present technology, neuromodulation of a left and/or right renal plexus (RP), which is intimately associated with a left and/or right renal artery, may be achieved through intravascular access. As FIG. 4A shows, blood moved by contractions of the heart is conveyed from the left ventricle of the heart by the aorta. The aorta descends through the thorax and branches into the left and right renal arteries. Below the renal arteries, the aorta bifurcates at the left and right iliac arteries. The left and right iliac arteries descend, respectively, through the left and right legs and join the left and right femoral arteries.

Figure 4B:
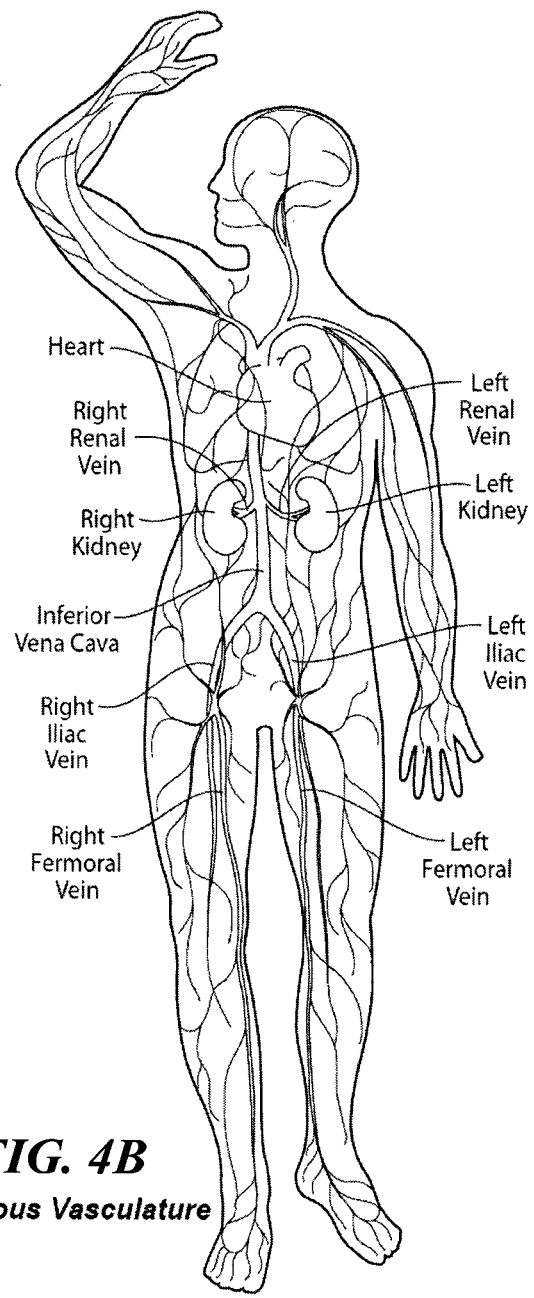

As FIG. 4B shows, the blood collects in veins and returns to the heart, through the femoral veins into the iliac veins and into the inferior vena cava. The inferior vena cava branches into the left and right renal veins. Above the renal veins, the inferior vena cava ascends to convey blood into the right atrium of the heart. From the right atrium, the blood is pumped through the right ventricle into the lungs, where it is oxygenated. From the lungs, the oxygenated blood is conveyed into the left atrium. From the left atrium, the oxygenated blood is conveyed by the left ventricle back to the aorta.

As will be described in greater detail later, the femoral artery may be accessed and cannulated at the base of the femoral triangle, just inferior to the midpoint of the inguinal ligament. A catheter may be inserted through this access site, percutaneously into the femoral artery and passed into the iliac artery and aorta, into either the left or right renal artery. This comprises an intravascular path that offers minimally invasive access to a respective renal artery and/or other renal blood vessels.

The wrist, upper arm, and shoulder region provide other locations for introduction of catheters into the arterial system. Catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using standard angiographic technique.

The diameter of a device that is inserted through an intravascular path should be considered in order to minimize invasiveness and for practicality. For example, a renal denervation procedure involving femoral artery access could have clinical advantages if it employs an introducer that is in size less than or equal to a 6 French compatible introducer (i.e., an introducer with an inner lumen that can accept a 6 French guide catheter or treatment catheter). Clinical advantages may include reduced risk of retroperitoneal bleeding; reduced need for interventions to seal the artery following the procedure, such as sutures, vascular seal, or vascular compression; and reduced hospital stay, for example reduced time spent in a recovery room. Larger catheters may be used for achieving intravascular access to a renal artery; however it may be at the expense of minimally invasiveness and practicality.

D. Properties and Characteristics of the Renal Vasculature

Since neuromodulation of a left and/or right renal plexus (RP) may be achieved in accordance with the present technology through intravascular access, properties and characteristics of the renal vasculature may impose constraints upon and/or inform the design of apparatus, systems and methods for achieving such renal neuromodulation. Some of these properties and characteristics may vary across the patient population and/or within a specific patient across time, as well as in response to disease states, such as hypertension, chronic kidney disease, vascular disease, end-stage renal disease, insulin resistance, diabetes, metabolic syndrome, etc. These properties and characteristics, as explained below, may have bearing on the clinical safety and efficacy of the procedure and the specific design of the intravascular device. Properties of interest may include, for example, material/mechanical, spatial, fluid dynamic/hemodynamic and/or thermodynamic properties.

As discussed previously, a catheter may be advanced percutaneously into either the left or right renal artery via a minimally invasive intravascular path. However, minimally invasive renal arterial access may be challenging, for example, because, as compared to some other arteries that are routinely accessed using catheters, the renal arteries are often extremely tortuous, may be of relatively small diameter and/or may be of relatively short length. Furthermore, renal arterial atherosclerosis is common in many patients, particularly those with cardiovascular disease. Renal arterial anatomy also may vary significantly from patient to patient, further complicating minimally invasive access. Significant inter-patient variation may be seen, for example, in relative tortuosity, diameter, length and/or atherosclerotic plaque burden, as well as in the take-off angle at which a renal artery branches from the aorta. Apparatus, systems and methods for achieving renal neuromodulation via intravascular access should account for these and other aspects of renal arterial anatomy and its variation across the patient population when minimally invasively accessing a renal artery.

In addition to complicating renal arterial access, specifics of the renal anatomy also complicate establishment of stable contact between neuromodulatory apparatus and a luminal surface or wall of a renal artery. Consistent positioning and contact force application between the cryo-applicator and the vessel wall is important for predictability. However, navigation is impeded by the tight space within a renal artery, as well as tortuosity of the artery. Furthermore, patient movement, respiration and/or the cardiac cycle may cause significant movement of the renal artery relative to the aorta, and the cardiac cycle may transiently distend the renal artery (i.e. cause the wall of the artery to pulse), further complicating establishment of stable contact.

Even after accessing a renal artery and facilitating stable contact between neuromodulatory apparatus and a luminal surface of the artery, nerves in and around the adventia of the artery should be safely modulated via the neuromodulatory apparatus. Safely applying thermal treatment from within a renal artery is non-trivial given the potential clinical complications associated with such treatment. For example, the intima and media of the renal artery are highly vulnerable to thermal injury. As discussed in greater detail below, the intima-media thickness separating the vessel lumen from its adventitia means that target renal nerves may be multiple millimeters distant from the luminal surface of the artery. Sufficient treatment should be delivered to the target renal nerves to modulate the target renal nerves without excessively damaging the vessel wall. Accordingly, the complex fluid mechanic and thermodynamic conditions present in the renal artery during treatment, particularly those that may impact heat transfer dynamics at the treatment site, may be important in applying a thermal-based treatment from within the renal artery.

The neuromodulatory apparatus should also be configured to allow for adjustable positioning and repositioning of the cryo-applicator within the renal artery since location of treatment may also impact clinical safety and efficacy. For example, it may be desirable to apply a full circumferential treatment from within the renal artery given that the renal nerves may be spaced circumferentially around a renal artery. However, the full-circle lesion likely resulting from a continuous circumferential treatment may create a heighten risk of renal artery stenosis, thereby negating any potential therapeutic benefit of the renal neuromodulation. Therefore, the formation of more complex lesions along a longitudinal dimension of the renal artery and/or repositioning of the neuromodulatory apparatus to multiple treatment locations may be desirable. It should be noted however that a benefit of creating a circumferential ablation may outweigh the perceived risk of renal artery stenosis or such risks may be mitigated with certain embodiments or in certain patients and creating a circumferential ablation could be a goal. Additionally, variable positioning and repositioning of the neuromodulatory apparatus may prove to be useful in circumstances where the renal artery is particularly tortuous or where there are proximal branch vessels off the renal artery main vessel, making treatment in certain locations challenging. Manipulation of a device in a renal artery should also consider mechanical injury imposed by the device on the renal artery. Motion of a device in an artery, for example by inserting, manipulating, negotiating bends and so forth, can cause injury such as dissection, perforation, denuding intima, or disrupting the interior elastic lamina.

Blood flow through a renal artery can be temporarily occluded for a short time with minimal or no complications. However, occlusion for a significant amount of time can cause injury to the kidney such as ischemia. It could be beneficial to avoid occlusion all together or, if occlusion is beneficial to the embodiment, to limit the duration of occlusion, for example to less than or equal to 2 minutes. In some patients, occlusion of less than or equal to 3 minutes may be tolerated.

Based on the above described challenges of (1) renal artery intervention, (2) consistent and stable placement of the cryo-applicator against the vessel wall, (3) safe application of thermal treatment across the vessel wall, (4) positioning and potentially repositioning the treatment apparatus to allow for multiple treatment locations, and (5) avoiding or limiting occlusion, various independent and dependent properties of the renal vasculature that may be of interest include, for example, vessel diameter, length, intima-media thickness, coefficient of friction and tortuosity; distensibility, stiffness and modulus of elasticity of the vessel wall; peak systolic and end-diastolic blood flow velocity, as well as the mean systolic-diastolic peak blood flow velocity, mean/max volumetric blood flow rate; specific heat capacity of blood and/or of the vessel wall, thermal conductivity of blood and/or of the vessel wall, thermal convectivity of blood flow past a vessel wall treatment site and/or radiative heat transfer; and renal artery motion relative to the aorta, induced by respiration, patient movement, and/or blood flow pulsatility, as well as the take-off angle of a renal artery relative to the aorta. These properties will be discussed in greater detail with respect to the renal arteries. However, dependent on the apparatus, systems and methods utilized to achieve renal neuromodulation, such properties of the renal arteries also may guide and/or constrain design characteristics.

An apparatus positioned within a renal artery should conform to the geometry of the artery. Renal artery vessel diameter, $D_{RA}$, typically is in a range of about 2-10 mm, with an average of about 6 mm. Renal artery vessel length, $L_{RA}$, between its ostium at the aorta/renal artery juncture and its distal branchings, generally is in a range of about 5-70 mm, more generally in a range of about 20-50 mm. Since the target renal plexus is embedded within the adventitia of the renal artery, the composite Intima-Media Thickness, IMT, (i.e., the radial outward distance from the artery's luminal surface to the adventitia containing target neural structures) also is notable and generally is in a range of about 0.5-2.5 mm, with an average of about 1.5 mm. Although a certain depth of treatment is important to reach the target neural fibers, the treatment should not be too deep (e.g., >5 mm from inner wall of the renal artery) to avoid non-target tissue and anatomical structures such as the renal vein.

An apparatus navigated within a renal artery must also contend with friction and tortuosity. The coefficient of friction, μ, (e.g., static or kinetic friction) at the wall of a renal artery generally is quite low, for example, generally is less than about 0.05, or less than about 0.03. Tortuosity, T, a measure of the relative twistiness of a curved segment, has been quantified in various ways. The arc-chord ratio defines tortuosity as the length of a curve, $L_{curve}$, divided by the chord, $C_{curve}$, connecting the ends of the curve (i.e., the linear distance separating the ends of the curve):

$$T=L_{curve}/C_{curve} \quad (1)$$

Renal artery tortuosity, as defined by the arc-chord ratio, is generally in the range of about 1-2.

The pressure change between diastole and systole changes the luminal diameter of the renal artery, providing information on the bulk material properties of the vessel. The Distensibility Coefficient, DC, a property dependent on actual blood pressure, captures the relationship between pulse pressure and diameter change:

$$DC=2*((D_{sys}-D_{dia})/D_{dia})/\Delta P=2*(\Delta D/D_{dia})/\Delta P \quad (2)$$

where $D_{sys}$ is the systolic diameter of the renal artery, $D_{dia}$ is the diastolic diameter of the renal artery, and ΔD (which generally is less than about 1 mm, e.g., in the range of about 0.1 mm to 1 mm) is the difference between the two diameters:

$$\Delta D=D_{sys}-D_{dia} \quad (3)$$

The renal arterial Distensibility Coefficient is generally in the range of about 20-50 $kPa^{-1}*10^{-3}$.

The luminal diameter change during the cardiac cycle also may be used to determine renal arterial Stiffness, β. Unlike the Distensibility Coefficient, Stiffness is a dimensionless property and is independent of actual blood pressure in normotensive patients:

$$\beta=(\ln[BP_{sys}/BP_{dia}])/(\Delta D/D_{dia}) \quad (4)$$

Renal arterial Stiffness generally is in the range of about 3.5-4.5.

In combination with other geometric properties of the renal artery, the Distensibility Coefficient may be utilized to determine the renal artery's Incremental Modulus of Elasticity, $E_{inc}$:

$$E_{inc}=3(1+(LCSA/IMCSA))/DC \quad (5)$$

where LCSA is the luminal cross-sectional area and IMCSA is the intima-media cross-sectional area:

$$LCSA=\pi(D_{dia}/2)^2 \quad (6)$$

$$IMCSA=\pi(D_{dia}/2+IMT)^2-LCSA \quad (7)$$

For the renal artery, LCSA is in the range of about 7-50 $mm^2$, IMCSA is in the range of about 5-80 $mm^2$, and $E_{inc}$ is in the range of about 0.1-0.4 $kPa*10^3$.

For patients without significant Renal Arterial Stenosis (RAS), peak renal artery systolic blood flow velocity, $v_{max-sys}$, generally is less than about 200 cm/s; while peak renal artery end-diastolic blood flow velocity, $v_{max-dia}$, generally is less than about 150 cm/s, e.g., about 120 cm/s.

In addition to the blood flow velocity profile of a renal artery, volumetric flow rate also is of interest. Assuming Poiseulle flow, the volumetric flow rate through a tube, φ, (often measured at the outlet of the tube) is defined as the average velocity of fluid flow through the tube, $v_{avg}$, times the cross-sectional area of the tube:

$$\phi=v_{avg}*\pi R^2 \quad (8)$$

By integrating the velocity profile (defined in Eq. 10 above) over all r from 0 to R, it may be shown that:

$$\phi=v_{avg}*\pi R^2=(\pi R^4*\Delta Pr)/8\eta\Delta x \quad (9)$$

As discussed previously, for the purposes of the renal artery, η may be defined as $\eta_{blood}$, Δx may be defined as $L_{RA}$, and R may be defined as $D_{RA}/2$. The change in pressure, ΔPr, across the renal artery may be measured at a common point in the cardiac cycle (e.g., via a pressure-sensing guidewire) to determine the volumetric flow rate through the renal artery at the chosen common point in the cardiac cycle (e.g., during systole and/or during enddiastole). Volumetric flow rate additionally or alternatively may be measured directly or may be determined from blood flow velocity measurements. The volumetric blood flow rate through a renal artery generally is in the range of about 500-1000 mL/min.

Thermodynamic properties of the renal artery also are of interest. Such properties include, for example, the specific heat capacity of blood and/or of the vessel wall, thermal conductivity of blood and/or of the vessel wall, thermal convectivity of blood flow past a vessel wall treatment site. Thermal radiation also may be of interest, but it is expected that the magnitude of conductive and/or convective heat transfer is significantly higher than the magnitude of radiative heat transfer.

The heat transfer coefficient may be empirically measured, or may be calculated as a function of the thermal conductivity, the vessel diameter and the Nusselt Number. The Nusselt Number is a function of the Reynolds Number and the Prandtl Number. Calculation of the Reynolds Number takes into account flow velocity and rate, as well as fluid viscosity and density, while calculation of the Prandtl Number takes into account specific heat, as well as fluid viscosity and thermal conductivity. The heat transfer coefficient of blood flowing through the renal artery is generally in the range of about 500-6000 $W/m^2K$.

An additional property of the renal artery that may be of interest is the degree of renal motion relative to the aorta, induced by respiration and/or blood flow pulsatility. A patient's kidney, located at the distal end of the renal artery, may move as much as 4" cranially with respiratory excursion. This may impart significant motion to the renal artery connecting the aorta and the kidney, thereby requiring from the neuromodulatory apparatus a unique balance of stiffness and flexibility to maintain contact between the thermal treatment element and the vessel wall during cycles of respiration. Furthermore, the take-off angle between the renal artery and the aorta may vary significantly between patients, and also may vary dynamically within a patient, e.g., due to kidney motion. The take-off angle generally may be in a range of about 30°-135°.

These and other properties of the renal vasculature may impose constraints upon and/or inform the design of apparatus, systems and methods for achieving renal neuromodulation via intravascular access. Specific design requirements may include accessing the renal artery, facilitating stable contact between neuromodulatory apparatus and a luminal surface or wall of the renal artery, and/or safely modulating the renal nerves with the neuromodulatory apparatus.

II. Cryo-Ablation

Various techniques may be employed to partially or completely incapacitate nerve cells, such as those nerves innervating the kidneys. One approach discussed herein, cryo-ablation, utilizes cryogenic temperatures to incapacitate nerve tissue associated with the kidneys, either completely or partially. Such incapacitation may be long-term (e.g., permanent or for periods of months, years, or decades) or temporary (e.g., for periods of minutes, hours, days, or weeks).

The use of cryogenic temperatures to perform tissue ablation is governed by rules of heat transfer. Heat is transferred via conduction and therefore Fourier's law of heat conduction is applicable in its various forms. Cryogenic tissue ablation is dependent on factors such as varying tissue heat capacities and conductivities, phase changes (heat of fusion for the tissues being ablated), blood flow and its associated heat load, thermal conductivity of material used to fabricate the cryo-applicator, contact surface area between the cryo-applicator and the tissue, and refrigeration power. Refrigeration power is measured in watts and maximizing refrigeration power for a given application temperature will produce the most effective ablation potential.

Generally, refrigeration systems utilize some form of refrigeration fluid (i.e., refrigerant) to both create the refrigeration energy and transfer heat. Methods of creating/applying refrigeration include: expansion of a compressed gas such as $N_2O$ or $CO_2$, thereby cooling by the Joule-Thomson (J-T) effect; evaporation of a condensed liquid such as liquid $N_2$ or liquid $N_2O$; and heat exchange with a high heat capacity cold fluid. Other materials used as refrigerants include argon, carbon dioxide, chlorodifluoromethane, dichlorodifluoromethane, and dichlorotetrafluoromethane.

The evaporation of a condensed liquid is a useful method of producing cryogenic temperatures for tissue ablation applications. Evaporation occurs at a specific temperature, i.e., the fluid's boiling point at a given pressure. The method of evaporating a liquid provides far greater refrigeration rates than the J-T expansion of the gas of the same compound. This improved refrigeration is due to the liquid already having its energy "removed" as part of the liquefaction process. Liquid $N_2O$ is frequently used. It may be maintained in a fully liquid state at room temperature when contained at a reasonably low pressure of about 750 psi to 760 psi (about 51 to 52 Atm). It is capable, when pressure is reduced to approximately atmospheric pressure (about 1 Atm or 14.696 psi) of changing state from liquid to gas and, in the process, cooling to about −88° C. It has a high refrigeration rate per unit mass, is relatively common and inexpensive and is non-toxic, non-flammable and non-corrosive. Since $N_2O$ may be maintained in a liquid state at room temperature it is well suited for use in a catheter.

A cryo-applicator can be considered as a portion of the device or catheter that applies cryogenic temperatures to tissue (i.e. that transfers energy from tissue in the form of heat). A cryo-applicator can comprise the cold surface that contacts tissue and also the material or materials that define the cold surface and/or the materials through which heat conducts from tissue to a cryogenic source (e.g., evaporating $N_2O$). A cryo-applicator can also comprise a mechanism that creates an endothermic state within, or in thermal communication with, the cold surface that contacts tissue. For example, a mechanism that creates an endothermic state may comprise a restriction orifice and an expansion chamber. A cryo-applicator region can be considered to comprise one or more cryo-applicators, one or more mechanisms that create an endothermic state, and may further comprise components in the region of the one or more cryo-applicators.

The mechanisms of tissue damage during cryosurgery include direct cell injury (e.g., necrosis), vascular injury (e.g., starving the cell from nutrients by damaging supplying blood vessels), and sublethal hypothermia with subsequent apoptosis. Exposure to cryotherapy may cause both acute cell death (immediately after exposure to the low temperature) and delayed cell death (during tissue thawing and subsequent hyperperfusion). An objective of the present approaches is to apply a structure at cryogenic temperatures to the inner surface of a renal artery wall such that contacted tissue is effectively cooled to a depth where sympathetic renal nerves reside. While cooling portions of a sympathetic renal nerve will slow and potentially block neural conduction, damaging at least a portion of a sympathetic renal nerve is expected to result in a prolonged or permanent reduction of renal sympathetic activity.

Cryo-ablation has certain characteristics that may be beneficial when used to make tissue ablations in a renal artery for renal neuromodulation. For example, rapidly cooling tissue is typically less painful to the patient than heating tissue to ablation temperatures. Less analgesic medication would presumably be required to maintain patient comfort during a procedure with cryo-ablation compared to a high temperature procedure. Additionally, reduced pain helps prevent patient movement, thereby increasing operator success and reducing procedural complications. In addition, a possible cause of vessel stenosis during a heating procedure is when collagen fibers are denatured causing the tissue to tighten and reduce the diameter of the artery. Cooling does not cause significant collagen tightening.

Further, the applicator of cryogenic temperatures (i.e., the cryo-applicator) adheres to moist tissue, thereby assuring stable, consistent, and continued contact during treatment. As will be appreciated, stable contact between an ablation device and tissue helps ensure reliable lesion creation. For example, as a patient breathes the kidneys rise and fall causing the renal artery to move. In addition blood flow is pulsatile causing the artery diameter to pulse. Furthermore, the patient could move or the catheter itself can move. Cryo-adhesion is also an advantage when ablating in very short renal arteries as this would facilitate stable contact. Energy delivery devices that do not adhere to the tissue can easily move out of place or jump into the aorta when applied to a portion of the renal artery that is very close to the ostium. Cryo-adhesion of a cryo-applicator can ensure stable contact is not compromised and an ablation is reliably created.

A. Cryo-System Components

With the foregoing in mind and turning to FIG. 5, the basic elements of one embodiment of an endovascular cryo-system 10 may include a cryo-console 100 and a cryo-catheter 102.

1. The Cryo-Console

When present, a cryo-console 100 contains a supply 104 of refrigerant 106 and a mechanism to control delivery of the refrigerant 106 to the cryo-catheter 102, such as the depicted supply tube or lumen 108 and control valve 110. The refrigerant supply 104 may be a single use cartridge or a refillable cylinder that maintains the refrigerant 106 at a desired pressure. For example, in one embodiment, liquid $N_2O$ is supplied at a pressure of 750 psi or greater so it is maintained as a liquid at room temperature.

Optionally, the cryo-console 100 may include one or more of a user interface, circuitry for monitoring sensors 112, if present in the cryo-catheter 102, one or more processors 114 or dedicated circuitry for implementing a computerized control algorithm, and control valves 110, 116 for controlling the flow of the refrigerant 106 to the cryo-catheter 102 and/or the flow of the evaporated refrigerant 118 from the cryo-catheter 102 through a return tube or lumen 120. In certain embodiments a cryo-applicator occludes a renal blood vessel while refrigerant is flowing through the cryo-catheter. Occlusion of the renal blood vessel for an excessive period of time can cause ischemia of a kidney. A cryo-console can mitigate the risk of ischemia by controlling the duration of refrigerant flow. For example, a cryo-console can automatically redirect or stop the flow of refrigerant at a predetermined time (e.g., less than or equal to 2 minutes) after flow is started by using an electronic or mechanical timer to control a valve. Alternatively, a timer can be incorporated into the catheter, for example, in the handle. If present, measurements from sensors 112 on the cryo-catheter 102 may be inputs to a control algorithm implemented on the cryo-console 100, such that operation of the cryo-console 100 may be regulated or adjusted based on this sensor feedback. In some embodiments, it may be desirable for the control algorithm to be fully automated, but in other embodiments the delivered therapy may utilize user input.

In certain embodiments, the cryo-console 100 may also precool the refrigerant 106 to provide greater refrigeration power in the refrigerant 106 by the time it reaches a cryo-applicator region 122 on the cryo-catheter 102, here depicted as an expandable balloon 124. A cryo-console 100 may optionally have a vacuum pump 126 to reduce backpressure of evaporated refrigerant 118 and increase refrigerant flow rate thus increasing refrigeration power. Optionally, control valve 116 can be used to control the amount of vacuum applied to the evaporated refrigerant 118 and thus control the reduction of backpressure of the evaporated refrigerant 118. In another embodiment, control valve 110 and/or 116 can be used to increase the backpressure of evaporated refrigerant 118. Increasing the backpressure of evaporated refrigerant could increase the boiling point. However, if the backpressure were only increased slightly the boiling point of the refrigerant could still be in a range that is suitable to create a cryogenic lesion. For example, if $N_2O$ were used as a refrigerant a slight increase in backpressure from 1 atm to about 2 atm would raise its boiling point from about $-88°$ C. to about $-75°$ C.; an increase in backpressure to 3 atm would raise its boiling point to about $-65°$ C. A small increase in backpressure in some embodiments can be applied to deploy or expand a cryo-applicator.

One consideration that may inform the design of a refrigeration system is the fact that heat transfer is proportional to the difference in temperature ($\Delta T$) between the refrigerant and the body that is being cooled. Importantly, heat transfer is also proportional to the amount of surface area of the body being cooled (A) that is in contact with the refrigerant. In addition to the above considerations (i.e., $\Delta T$ and A), when the refrigerant is a fluid, the refrigeration potential of the refrigerant fluid is also a function of its mass flow rate. Specifically, the faster a heat-exchanging fluid refrigerant can be replaced (i.e., the higher the mass flow rate), the higher the system's refrigeration potential.

The mass flow rate of a fluid through a tube results from a pressure differential on the fluid. The higher the pressure differential ($\Delta P$) of a refrigerant fluid in a system, the higher the resulting increase in the mass flow rate of the fluid and, accordingly, the refrigeration potential of the system. This increased flow rate, however, creates additional increases in the return pressure (i.e., back pressure) that may cause an increase in the boiling point temperature of the refrigerant, which may weaken the system's refrigeration potential. Thus, for relatively low mass flow rates, increases in the mass flow rate of the refrigerant will cause lower temperatures.

Refrigerant flow in this range is said to be "refrigeration limited." On the other hand, for relatively high mass flow rates, increases in the mass flow rate can actually cause the temperature of the refrigerant to rise. Since increases in mass flow rate will no longer improve refrigeration, flow in this range is said to be "surface area limited." Operation under "refrigeration limited" conditions is uncommon since all it takes to increase refrigeration power under such conditions is to increase mass flow rate. Hence, it is generally more common to see systems that are "surface area limited".

From the above discussion, it can be appreciated that several embodiments of a cryocatheter refrigeration system configured in accordance with the present technology can address the following functional objectives:

1. The system can be configured to deliver the refrigerant to the distal segment of the cryocatheter in a liquid state so that the liquid can boil/evaporate at the tip and absorb latent heat.
2. The system can be configured to evacuate the expanded refrigerant and maintain the pressure where the refrigerant boils at a low pressure to allow the refrigerant to boil at a low temperature.
3. The system can be configured to perform the first two functions at a sufficient refrigerant mass flow rate to generate the necessary refrigeration potential to efficiently cryoablate tissue. It is also desirable for the ablation and rewarming cycle to be completed within several minutes.
4. The catheter can be configured to accommodate the space constraints and topology of the renal artery without substantially stretching the arterial wall, yet consistently achieve contact between the cryoapplicator and renal artery wall. This objective may also include accommodating atraumatic delivery of the cryocatheter into the renal artery.

In light of the above, it is desirable to have a cryocatheter configuration that optimizes both the catheter's outer diameter and the size of the catheter's internal refrigerant flow path and ensures that the cryocatheter does not operate in a refrigerant limited condition, maintains a refrigerant in a liquid state as it transits through a supply tube and simultaneously maintains the pressure in a refrigerant return line at about 1-2 atm.

In some instances, it may also be desirable to have a gauge pressure of less than or equal to 1 atm. Technical considerations allow pressure to fluctuate within the range of several atmospheres. The lower pressure is acceptable for as long as the desired geometry of the balloon is maintained and the excessive vacuum does not collapse the balloon. Pressure of, for example, 2 atm may increase the temperature of cryo applicator by 3-5° C., which can be tolerated since nerves are destroyed within a relatively wide range of negative temperatures.

2. The Cryo-Catheter

The cryo-catheter 102 may comprise an elongate body (e.g., a handle and shaft 130) that helps position the cryo-applicator region 122 at the target site and/or delivers refrigerant 106 from a source, such as from the cryo-console 100 or from a cartridge in a handle of the cryo-catheter 102, to the cryo-applicator region 122. A cryo-catheter 102 may, in certain embodiments, include a guidewire lumen that allows a guidewire to be used in advancing and positioning the cryo-catheter 102. However, other embodiments may not utilize a guidewire or guidewire lumen. In addition, the cryo-catheter 102 typically includes structures (e.g., return tube or lumen 120) to facilitate removal of the expanded refrigerant (e.g., evaporated refrigerant 118) from the cryo-applicator region 122 to a location outside the patient's body.

For example, when the refrigerant 106 is supplied as liquid $N_2O$ it is supplied at a pressure of 750 psi to ensure it is maintained in a liquid state at room temperature. The liquid $N_2O$ is delivered through a supply lumen 108 to the cryo-applicator region 122 where the refrigerant 106 undergoes expansion. For example, the supply lumen 108 may have an inner diameter of less than or equal to 0.010 inches (i.e., about 0.025 cm) which could provide sufficient flow of liquid $N_2O$. In, or proximate to, the cryo-applicator region 122, the refrigerant 106 flows from the supply lumen 108 through a restrictive orifice 132 (e.g., a capillary tube, porous plug, flow restrictor, nozzle) into an expansion chamber 134 of some sort, here depicted as the interior of a cryo-balloon 124, where the refrigerant 106 expands under lowered pressure and changes phase from liquid to gas. The restriction orifice 132 provides resistance to flow and thus maintains a high pressure differential between the supply lumen and the expansion chamber 134. The flow rate of refrigerant may be influenced by the flow resistance provided by the restriction orifice 132. In certain embodiments restrictive orifice 132 may be a capillary tube having a smaller inner diameter than the supply lumen 108. For example the inner diameter of a capillary tube used as a restrictive orifice 132 may be between about 0.002" (i.e. 0.05 mm) and about 0.005" (i.e. 0.13 mm) and have a length between about 1.5" (i.e. 38 mm) to 30" (762° mm). A restriction orifice 132 as such may facilitate a flow rate of $N_2O$ from a pressurized supply tube 108 to an expansion chamber 134 in the range of 3 to 5 standard liters per minute (3-5 standard liters per minute of gas is equivalent to about 5.9 to 9.8 grams per minute of $N_2O$). As will be appreciated, the restrictive orifice need not have an opening having a circular cross-section, but may instead consist of a suitable sized slot or slit.

The phase change of the refrigerant 106 is an endothermic reaction absorbing thermal energy from its surroundings. In a present embodiment, the cryo-applicator region 122 contacts a targeted tissue in a renal artery at a sufficiently low temperature as to cause denervation up to a desired depth within the contacted tissue. Various embodiments of the cryo-applicator region 122 designed for use in a renal artery for sympathetic renal nerve neuromodulation are described herein. The evaporated refrigerant 118 is exhausted from the cryo-applicator region 122 through a return lumen 120 in the elongate body (e.g., the catheter shaft 130) of the cryo-catheter 102. The return lumen 120 is ideally proximate to or surrounding the supply lumen 108 and has a larger inner volume and/or cross-section area (in the event multiple return lumens are present) in order to minimize the pressure drop along the length of the return lumen 120, i.e. to maintain a low pressure in the cryo-applicator region 122. A small change in pressure can have a large impact on changing the boiling temperature of the refrigerant 106, such as $N_2O$. The lower the pressure in the expansion chamber 122, the lower the boiling temperature will be and thus, the temperature of the cryo-applicator and the penetration depth will be greater. There may be a maximum pressure in an expansion chamber suitable for achieving temperatures low enough for cryo-ablation of renal nerves, for example a maximum pressure may be less than or equal to about 4 atm absolute. For example, pressure in the expansion chamber 134 may be maintained in the range of 1.4 to 2 atm absolute. Pressure in the expansion chamber 134 may be in part dictated by the pressure difference between the expansion chamber and exhaust of an exhaust lumen to atmosphere. For example, a pressure difference of 0.4 to 1 atm through the exhaust lumen may maintain a pressure of 1.4 to 2 atm in the expansion chamber. Such a pressure difference may be provided with a flow rate of about 5 standard liters per minute and an exhaust lumen with a length of about 70 cm and an inner diameter of about 0.05".

In one embodiment, portions of the cryo-catheter 102 may be controllably deflectable. In one such embodiment, the cryo-catheter 102 can include a handle, a control wire, a flexibly biased member (e.g., a laser cut tube), and an actuator for controlling deflection. In particular, the flexing of the catheter shaft 130 and/or the applicator region 122 may be accomplished as provided in U.S. patent application Ser. No. 12/545,648, entitled "Apparatus, Systems, and Methods for Achieving Intravascular, Thermally-Induced Renal Neuromodulation," to Wu et al., which is incorporated by reference herein in its entirety. In other embodiments, other mechanisms for applying bias and controlling or inducing flexion may also be employed.

In other embodiments, the cryo-catheter 102 may include a controller or computer system having programmed instructions for controlling delivery of refrigerant 106, evacuation of evaporated refrigerant 118, and/or other aspects of the treatment. For example, the controller can be a mechanical valve or an electronic controller communicating with the cryo-console 100 or with a source 104 of refrigerant 106 stored within the cryo-catheter 102 itself, such as within a handle of the cryo-catheter 102, as discussed in greater detail below.

Further, in certain embodiments the cryo-catheter 102 can comprise sensors 112 to measure or monitor variables such as pressure, temperature, tissue impedance, flow rate, infusate or coolant temperature, blood flow rate, blood temperature, tissue temperature, tissue electrical and thermal characteristics, and/or body temperature. Measurements of such variables obtained by sensors 112 of the cryo-catheter 102 may be provided as inputs to a control algorithm, such as may be implemented on a processor 114 or other suitable computer system associated with the cryo-console 100 or with another component of the cryo-system 10, such as the cryo-catheter 102. The control algorithm can include, among other things, programmed instructions for automating all or a portion of the cryomodulation process. The control algorithm, controller, and associated components may include one or more features as provided in U.S. patent application Ser. No. 12/147,154, entitled "Methods and Systems for Thermally-Induced Renal Modulation," to Demarais et al, which is incorporated by reference herein in its entirety.

The algorithm, the programmed instructions for controlling delivery of the refrigerant, evacuation of the evaporated refrigerant, and/or other aspects of the treatment can be implemented as a conventional computer program for execution by a processor operably coupled to the cryo-system 10. For example, the system 10 may include one or more computing system hardware and/or software modules. In other embodiments, computer hardware and software can be utilized to facilitate any crymodulation process or system. The algorithm, instructions for controlling delivery of the refrigerant, and/or other aspects of the treatment can also be controlled manually by an operator or a physician administering treatment.

Figure 5A:
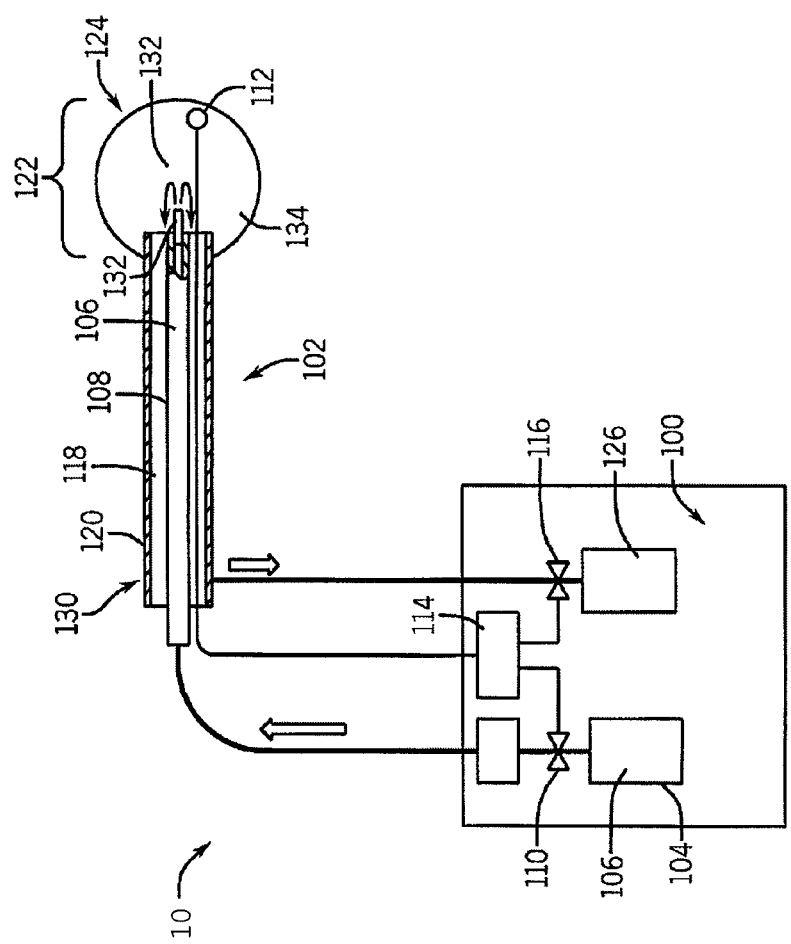
FIG. 5A is a partially schematic diagram illustrating one example of a cryoablation system including a cryoablation console (i.e., a cryo-console) and an intravascular cryoablation catheter (i.e., a cryo-catheter) configured in accordance with an aspect of the present disclosure.
Figure 5B:
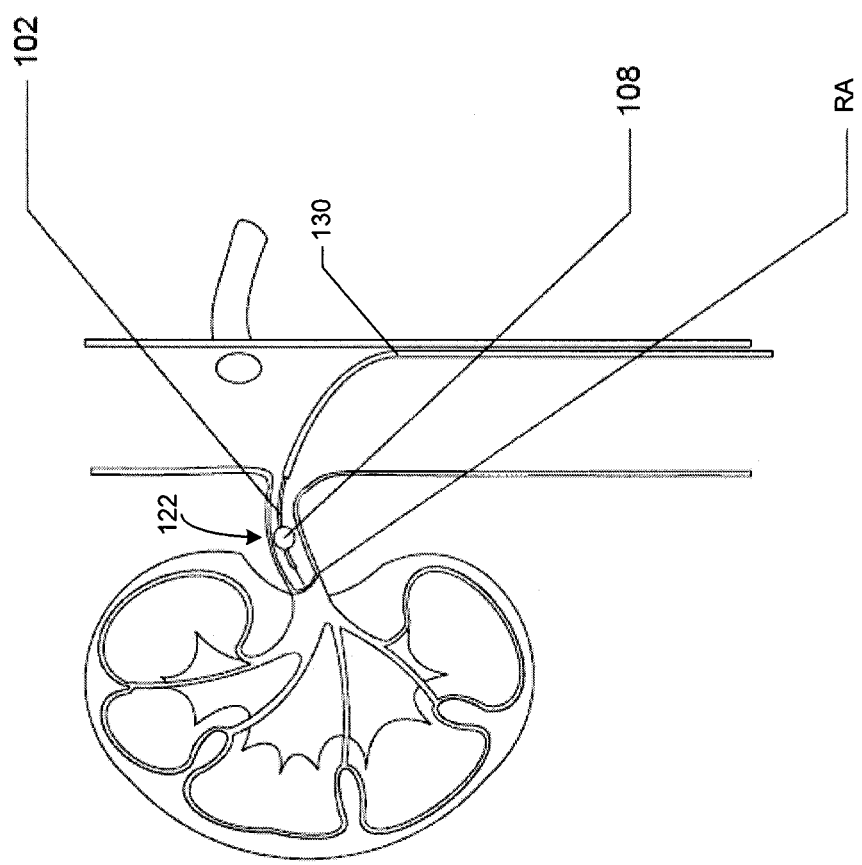
FIG. 5B illustrates placement of a cryo-catheter on an inner wall of a renal artery of a patient.

As will be appreciated, in various embodiments, the cryo-catheter 102 is designed to facilitate various aspects of renal artery intervention. FIG. 5B, for example, illustrates placement of the cryo-catheter 102 on an inner wall of a renal artery RA of a patient. The cryotherapy applicator (e.g., balloon) 108 is positioned to perform neuromodulation (e.g., circumferential or segmented ablation of renal nerves proximate to the renal artery). Portions of the cryo-catheter 102, such as the shaft 130 and/or the applicator region 122, may be sized or constructed with sufficient flexibility to allow navigation atraumatically to a desired location within the renal artery RA. For example, in one embodiment, the cryo-catheter 102 is able to navigate a bend from the aorta to a renal artery that has a radius of curvature as small as 15 mm. Further, advancing through the renal artery RA could require passage through a very tortuous vessel. Therefore, as noted above, some embodiments involve controlled deflection of the cryo-applicator region 122 and/or the shaft 130 to create cryo-ablations at desired locations along the renal artery wall. Such controllable deflection, in conjunction with the size and shape of the cryo-applicator region 122, may be useful in positioning the cryo-applicator region 122 in an appropriate location in the renal artery so an ablation is made where desired. For example, it may be undesirable to ablate near a smaller branching vessel.

Likewise, the cryo-catheter 102 may be sized and/or constructed so that sufficient refrigeration power is achieved at the cryo-application region 122. For example, pre-clinical experiments have shown that an ablation of about 3 mm deep in the renal artery environment can be achieved using the cryo-catheter 102. Correspondingly, to the extent that vessel diameters vary and that certain embodiments discussed herein include a cryo-applicator region 122 of varying size (such as a balloon 124), it may be desirable to be able to choose or control the size of the applicator to make contact with various diameters of vessel wall without traumatically distending the wall. Similarly, it may be desirable to have a cryo-applicator region 122 that is sized and/or shaped so as to create ablations having the desired size, shape, location, and/or configuration alone or with respect to other ablations.

B. The Delivery Sheath

A delivery sheath is commonly used to gain intravascular access to a renal artery and may provide a passageway through which a cryo-catheter 102 can be delivered to the renal artery. A delivery sheath may also be used to contain a cryo-applicator and/or distal end of a catheter that is deployed when the delivery sheath is retracted. The amount of retraction can dictate the degree of deployment or the length of an exposed cryo-applicator. As used herein, a delivery sheath may encompass simple guide catheters as well as other delivery sheath structures. Such delivery sheaths may be "off-the-shelf" or custom, depending on the embodiment. A delivery sheath may incorporate functional features such as steering and deflection capabilities to facilitate delivery and positioning of the cryo-catheter in the renal artery. A delivery sheath can be integrated as part of a device, supplied separately or supplied as part of a kit.

In one implementation, the femoral artery can be cannulated at the base of the femoral triangle, just inferior to the midpoint of the inguinal ligament. A cryo-catheter 102 can gain access through this access site, for example through a percutaneous introducer into the femoral artery and passed into the iliac artery and aorta, into either the left or right renal artery. This comprises an intravascular path that offers minimally invasive access to a respective renal artery and/or other renal blood vessels.

The wrist, upper arm, and shoulder region provide other locations for introduction of catheters into the arterial system. Catheterization of either the radial, brachial, or axillary artery may be utilized in select cases. Catheters introduced via these access points may be passed through the subclavian artery on the left side (or via the subclavian and brachiocephalic arteries on the right side), through the aortic arch, down the descending aorta and into the renal arteries using a standard angiographic technique.

For practical purposes, the maximum outer dimension (e.g., diameter) of any section of the cryo-catheter 102 in a reduced delivery configuration (as applicable), including the cryo-applicator region 122, is dictated by the inner diameter of the delivery sheath through which the catheter is passed. Assuming, for example, that an 8 French delivery sheath (which has an inner diameter of approximately 0.091 inches (i.e., 2.3 mm) would likely be, from a clinical perspective, the largest guide catheter used to access the renal artery, and allowing for a reasonable clearance tolerance between the cryo-catheter 102 and the delivery sheath, the maximum outer dimension realistically can be expressed as being less than or equal to approximately 0.085 inches (i.e., about 2.2 mm). However, use of a smaller 5 French delivery sheath may require the use of smaller outer diameters along the cryo-catheter 102, for example no greater than 0.053 inches (i.e., about 1.35 mm). In another example, a cryo-catheter 102 that is to be routed within a 6 French delivery sheath would have an outer dimension of no greater than approximately 0.07 inches (i.e., about 1.78 mm). A lubricous coating can be added to an applicator and/or an elongated shaft to facilitate passage through a guide catheter/delivery sheath.

C. Alternative Cryo-System Configurations

While the preceding discussion outlines various components that may be present in a cryo-system 10, it should be understood that not all of the disclosed components need be present in every embodiment and that, indeed, functionality of different components may be combined or integrated into a single structure in other embodiments. For example, the cryo-console 100 functionality discussed above may be provided as a discrete and separate component from the cryo-catheter 102, allowing a single cryo-console 100 to be used with different cryo-catheters 102 and/or allowing a user to configure and monitor the operation of the cryo-console 100 and a connected cryocatheter 102. However, in other embodiments, aspects of the functionality of the cryo-console 100 may be integrated into the cryo-catheter 102 itself, thus eliminating the need for a separate cryo-console component. In such an embodiment, the cryo-catheter 102 may be discarded after a single-use or after a limited number of uses (such as two, three, four, or five uses) or after treatment of a single patient. As will be appreciated, in a single-use implementation, problems associated with cleaning and sterilizing a device prior to reuse may be avoided.

Figure 6:
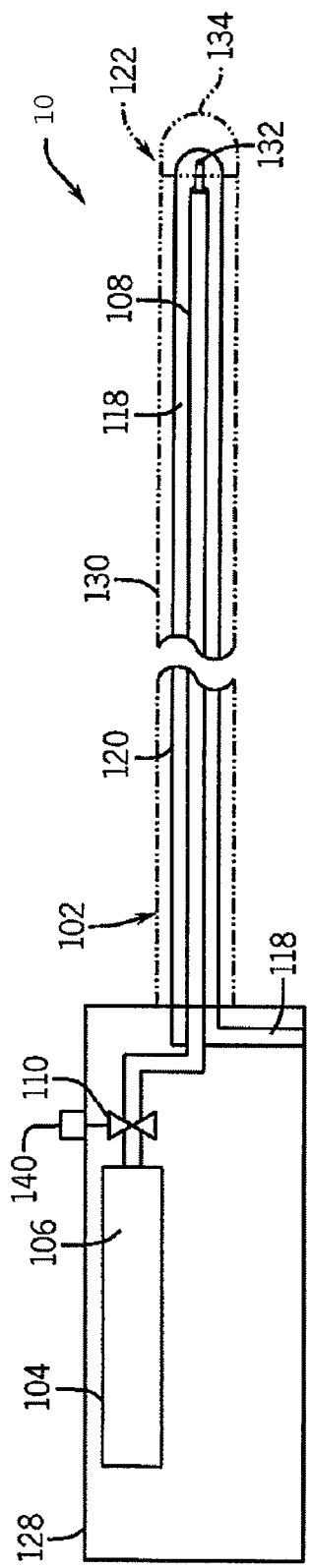
FIG. 6 is a partially schematic diagram illustrating one example of a cryo-catheter suitable for stand-alone use without a discrete and separate cryo-console configured in accordance with an aspect of the present disclosure.

For example, turning now to FIG. 6, in one embodiment the cryo-catheter 102 may include a supply 104 of refrigerant 106, such as in the handle 128 of the cryo-catheter 102. Thus, in such an embodiment, the cryo-catheter 102 need not be connected to a separate cryo-console component but may instead be a discrete and standalone (i.e. self-contained) device capable of independent operation. Indeed, the cryo-catheter 102 in such an embodiment may be devoid of connectors or cables for connecting to a separate cryo-console. In one such implementation, the refrigerant supply 104 may be a replaceable cartridge or canister, such as of $N_2O$. In other implementations, the refrigerant supply 104 may not be refillable and the cryo-catheter 102 may be disposed of once the refrigerant 106 is depleted. For example, pressurized container such as a cartridge or canister containing less than about 20 g of liquid $N_2O$ may be an appropriate size and weight to insert into a catheter handle and contain an appropriate amount of liquid refrigerant to sufficiently cryo-ablate renal nerves.

Due to the heat transfer properties associated with the renal vasculature and surrounding renal sympathetic nerves and the depth of the nerves from the vessel wall surface, it may be possible with a relatively small amount of liquid refrigerant to create refrigeration power in a cryo-applicator associated with cryo-catheter 102 sufficient to incapacitate the targeted nerves. For example, 14.7 g of liquid $N_2O$ may be sufficient to create a flow of about 5 L/min of gas for 90 seconds; 19.6 g of liquid $N_2O$ may be sufficient to create a flow of about 5 L/min of gas for 120 seconds; 5.9 g liquid $N_2O$ may be sufficient to create a flow of about 3 L/min of gas for 60 seconds.

In such an implementation where the refrigerant supply 104 is provided as a cartridge within the handle 128, a puncture pin may be actuated to break a seal on the cartridge. A separate valve, such as control valve 110 may control the flow of the refrigerant 106 to the cryo-applicator region 122, such as by operation of an external control 140 (e.g., a button, knob, or lever) on the handle 128. Control of the flow via the external control 140 may simply allow the flow of refrigerant 106 to be started and stopped or may allow the flow rate of refrigerant 106 to be adjusted. Alternatively, in other implementations, the flow rate of the refrigerant 106 may not be adjusted by the user.

In the depicted embodiment, the evaporated refrigerant 118 is depicted as returning to handle 128 via the return lumen 120, where it is vented out of the handle 128. In other embodiments, the evaporated refrigerant 128 may be vented out of the catheter shaft 130 prior to reaching the handle 128 but outside of the patient's body, such as proximate to the handle 128. Thus, as used throughout the present disclosure, it should be understood that a cryo-system 10 and/or cryo-catheter 102 may have a variety of different configurations and/or features, including a standalone or self-contained, handheld cryo-catheter 102 or a cryo-catheter 102 connected to a discrete and separate cryo-console 100.

III. Cryo-Catheter Configurations for Renal Artery Intervention

With the foregoing discussion of the cryo-system 10 configurations in mind, a variety of different configurations of cryo-catheters and, in particular, cryo-applicator regions are described below with reference to FIGS. 7A-43. It will be appreciated that the following devices and/or specific features of the devices described below may be used with the cryo-system 10 (FIGS. 5A and 6), used as a standalone or self-contained handheld device, or used with other suitable systems. Further, many of the features of the cryo-system 10 described above with reference to FIGS. 5A and 6 are discussed and referenced in the discussion below without specifically referring back to FIGS. 5A and 6 in each instance where one of these features may be mentioned.

For ease of reference, throughout this disclosure identical reference numbers are used to identify different parts. Although the parts may be similar in structure and/or function, the use of the same reference number does not imply that the parts should be construed to be identical. Indeed, in many examples described herein, the identically numbered parts are distinct in structure and/or function.

A. Point Ablate Cryo-Applicator

Figure 7A:
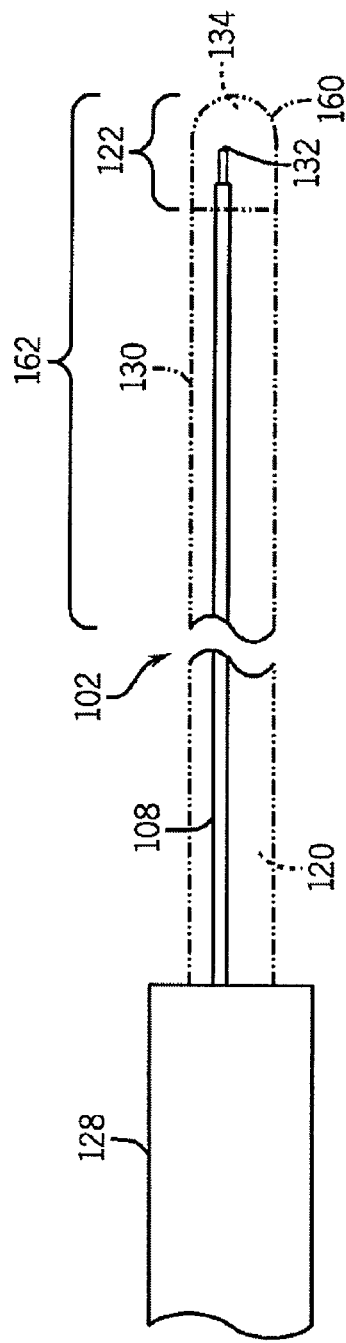
FIGS. 7A-8C are partially schematic views of embodiments of cryo-catheter configurations suitable for point ablation configured in accordance with an aspect of the present disclosure.

FIGS. 7A-8C are partially schematic views of cryo-catheter configurations in accordance with embodiments of the technology. Referring first to FIGS. 7A and 7B, for example, the cryo-applicator region 122 suitable for forming point ablations in the renal artery may be provided as a metal (e.g., stainless steel, platinum, silver) tip 160 defining or containing the expansion chamber 134 where the liquid refrigerant 106 expands to a gas. As will be appreciated, the metal tip 160 does not expand in response to the internal pressure associated with evaporation of the refrigerant 106, but merely becomes colder. In one such embodiment in which $N_2O$ is employed as the refrigerant 106, the metal tip 160 is highly thermally conductive and its surface temperature is close to the temperature of the refrigerant 106, i.e., approximately −8° C. to −90° C. The surface area of the metal tip 160 is a function of its diameter and length. For example, in one implementation the diameter of the tip 160 is less than or equal to 0.091 inches (i.e., about 2.3114 mm) to fit through an 8 French delivery sheath or less than or equal to 0.070 inches (i.e., about 1.778 mm) to fit through a 6 French delivery sheath.

Figure 7B:
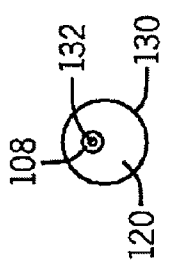

As discussed above with respect to FIG. 5 and as depicted in FIGS. 7A and 7B, the cryo-catheter 102 includes the shaft 130 (which may be of uniform or varying diameter) in which the refrigerant 106 passes through a supply lumen 108 and in which the evaporated refrigerant 118 passes though return lumen 120, which may surround or encompass the supply lumen 108, as depicted. In certain embodiments, a guidewire lumen may also be present. Likewise, sensors (such as sensors for measuring temperature and pressure) may be present in the cryo-catheter 102 and may communicate with one or more executable control algorithms suitable for monitoring and/or controlling the cooling and/or warming of the cryo-applicator region 122. Similarly, radio-opaque markers or other radio-opaque structures may be present that allow portions of the cryo-catheter to be visualized using non-invasive imaging technology during or prior to a procedure.

The refrigerant 106 may exit the delivery lumen through one or more restriction orifices 132 or tube openings which may direct the refrigerant into the expansion chamber 134. In certain implementations, the refrigerant 106 may be generally directed into the expansion chamber 134, such that the metal tip 160 is generally and non-specifically cooled (i.e., cooled generally uniformly across the surface of the tip 160). Alternatively, in other implementations, the refrigerant 106 may be directed in one or more specific directions in the expansion chamber 134, such as toward specific internal walls of the metal tip 160, such that specific portions of the metal tip 160 (such as the end of the tip 160 or specific walls of the tip 160) are preferentially cooled. In such an implementation, the preferentially cooled portions of the metal tip 160 may be those that are contacted against the walls of the renal artery (such as by a suitable deflection mechanism, as discussed herein) to cause lesion formation.

In embodiments where the tip 160 is made from metal and is rigid, the length of the tip 160 may impact its ability to pass through a bend (e.g., through a delivery sheath from the aorta to the renal artery) over a guidewire that makes a sharp bend or through a tortuous renal artery. For example, a suitable length and diameter of the cryo-applicator region 122 in the form of a metal tip 160 that could pass through a 6 French delivery sheath and with a radius of curvature of 15 mm could be less than or equal to about 3 mm long and about 0.060 inches (i.e., about 1.524 mm) in diameter. In other embodiments, however, the cryo-applicator region 122 including the metal tip 160 can have other arrangements or dimensions.

As will be appreciated, a temperature gradient across a thin metal wall is relatively low in the metal tip 160 embodiment due to the superior thermal conductivity of the metal. An ablation formed using the metal tip 160 may be relatively small but still sufficient to reduce renal sympathetic activity. In smaller vessels (e.g., about 4 mm inner diameter) a single ablation made by a 0.060 inch (i.e., about 1.524 mm) diameter, 3 mm long applicator may cover about 25% to 40% of the vessel circumference which could establish a significant probability of targeting a sufficient portion of the nerve supply. However, this probability can be increased, especially in larger vessels, if multiple point ablations are made. The advantage of multiple point ablations is that they can be spaced apart and separated by unaffected tissue which may be safer than targeting a large amount of tissue in a continuous configuration. Furthermore, the physician can have control over where the ablations are located and can avoid locations where there are small branching vessels or other locations that are preferentially avoided.

In one embodiment, the distal end 162 of the shaft 130 of the catheter (e.g., about 30 mm or less) can be controllably deflected in one or multiple directions. For example, controllable deflection may be achieved with a pull wire connected to an actuator in the handle 128 and a flexibly biased member. Alternatively, in other embodiments, the distal end 162 can have a pre-formed shape such as a curved shape, which is deployed when a delivery sheath is retracted, or other means of controllable deflection may be employed. Full actuation of the actuator in the handle 128 can deflect the metal tip 160 to a maximal deflection state in which the metal tip is moved a maximum distance from the longitudinal axis of the elongated shaft. Such a maximal deflection state could be suitable for positioning the metal tip in contact with a renal artery wall without moving the metal tip beyond the maximum distance so as to reduce a risk of applying traumatic force to the artery wall. For example, a maximal deflection state can comprise a maximum distance of no less than about 5 mm and no more than about 15 mm from the longitudinal axis of the elongated shaft.

Figure 8A:
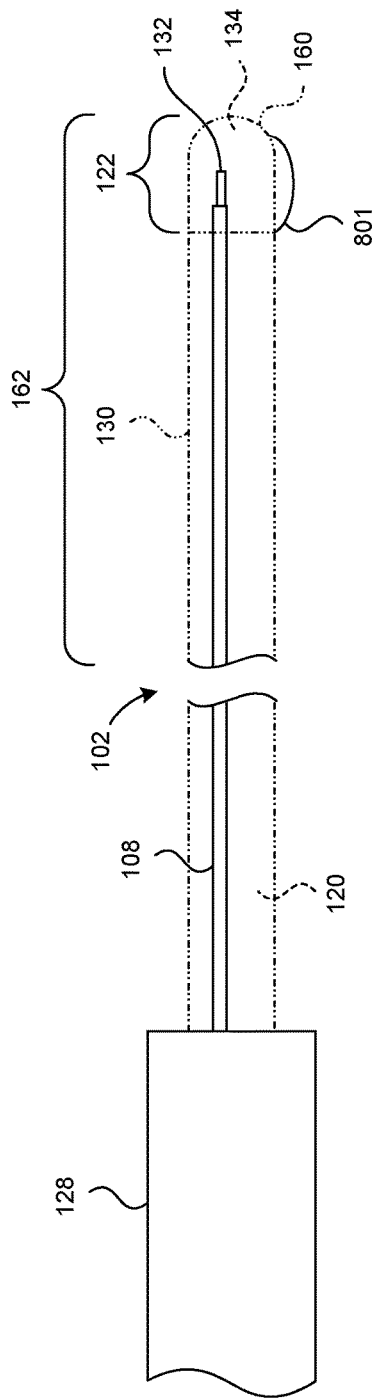
Figure 8C:
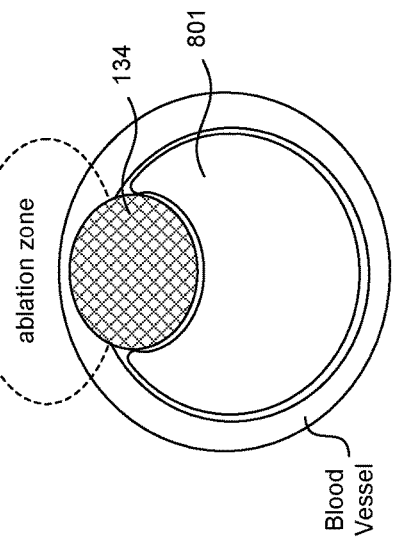
Figure 8B:
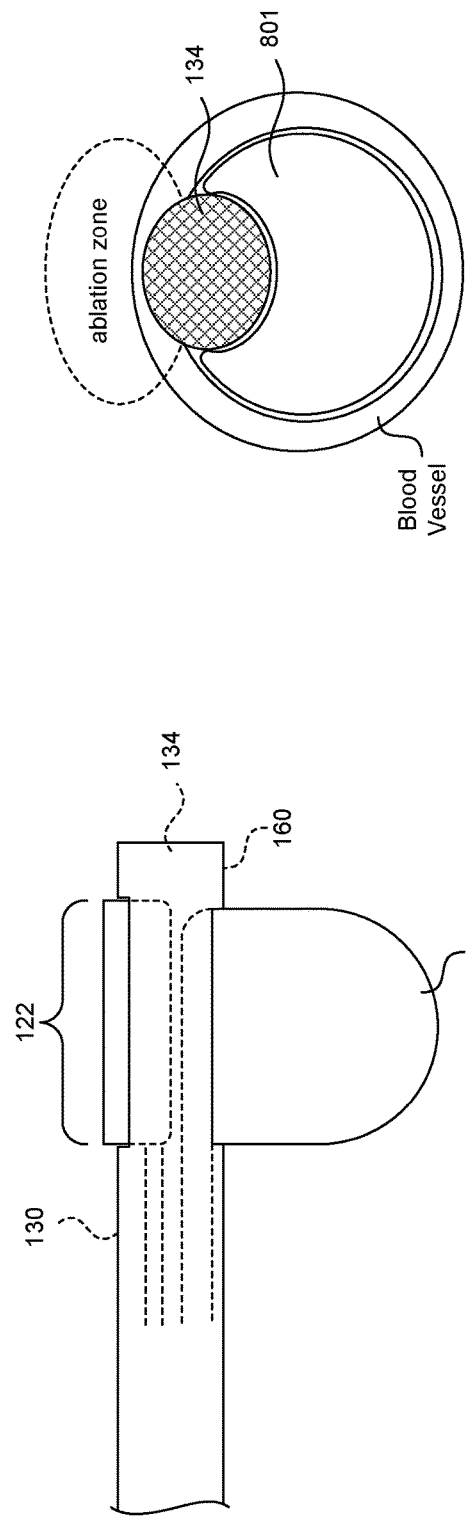

In still another embodiment illustrated in FIGS. 8A-8C, the applicator region 122 is configured with a point ablate cryo-applicator comprising an inflatable balloon 801 configured to occlude a blood vessel 170 (FIGS. 8B and 8C) and urge the cryo-applicator into contact with the vessel wall. The balloon 801 may be inflated with a non-cooling fluid or gas (e.g., saline, contrast, $CO_2$, etc.) so that cryo-ablation only occurs at a partial circumference of the vessel. The balloon 801 may be a compliant balloon so it conforms to a range of vessel diameters. In other embodiments, however, the balloon 801 and/or the applicator region 122 may have another arrangement and/or include different features.

B. Linear or Continuous Ablation Applicator

In an additional embodiment, the applicator region 122 may be configured not to ablate a point or spot region of tissue, but instead to ablate a strip or contiguous region of tissue. In such embodiments, for example, the applicator region 122 may be provided as a flexible, elongate member that can navigate bends to be delivered into the renal artery. The length of the applicator can create an elongated region of ablation along a portion of the inner wall (e.g., about 1 cm) or an ablated region shaped like a curve or helix (e.g., about 1.5 cm to about 3 cm long) along the wall of the renal artery. In certain embodiments, the applicator region 122 may be configured so as to be non-occlusive when deployed so blood can continue to flow through the vessel to the kidney.

In such implementations, the applicator region 122 may initially be deployed at the target site in a first configuration, such as a straight or slightly bent configuration. Once at the target site, however, the applicator region 122 may be converted to a second shape or configuration (e.g., curved or helical) suitable for ablating tissue at the target site (i.e., arterial wall 170) in the desired configuration. For example, such configuration changes may be accomplished by use of a control wire to pull or otherwise deflect the application region to the operational configuration, by removing a restraining guidewire 164 disposed in a guidewire lumen 166 within the shaft 130, by removing a delivery sheath 168, or by applying internal pressure (such as due to evaporation of the refrigerant 106 to generate pressure on the inner walls of the applicator region 122). In one such embodiment, the gas expansion can cause the applicator region 122 to assume a helical configuration which expands outward to make contact against the vessel wall 170 to form lesions 172.

FIGS. 9A-10B are partially schematic views of cryo-catheter configurations in accordance with additional embodiments of the technology. For example, FIGS. 9A and 9B depict an implementation in which the applicator region 122 is initially deployed in a substantially straight configuration (as shown in FIG. 9A). Once at or near the target site, a restraining wire 164 may be partially removed (see FIG. 9B) via lumen 166 such that a natural bias or tension in the applicator region 122 is no longer resisted. In the absence of resistance provided by the restraining wire 164, the applicator region 122 may assume a second configuration, such as the depicted curved or bent configuration, suitable for ablating a continuous strip (e.g., an elongated region, a curved region, or a helical region) in the blood vessel (e.g., renal artery) 170 to form lesions 172. By controlling the amount or extent of restraining wire 164 which is removed, the user may determine the shape of the applicator region 122 or the extent of the applicator region 122 that is altered in shape or otherwise configured for use as an ablative surface in the renal artery 170. In the depicted embodiment, the supply lumen 108 is depicted as generally conforming to the shape of the applicator region 122 when deployed, i.e., the supply lumen 108 bends with the applicator region 122 to conform to the deployed configuration.

Figure 10A:
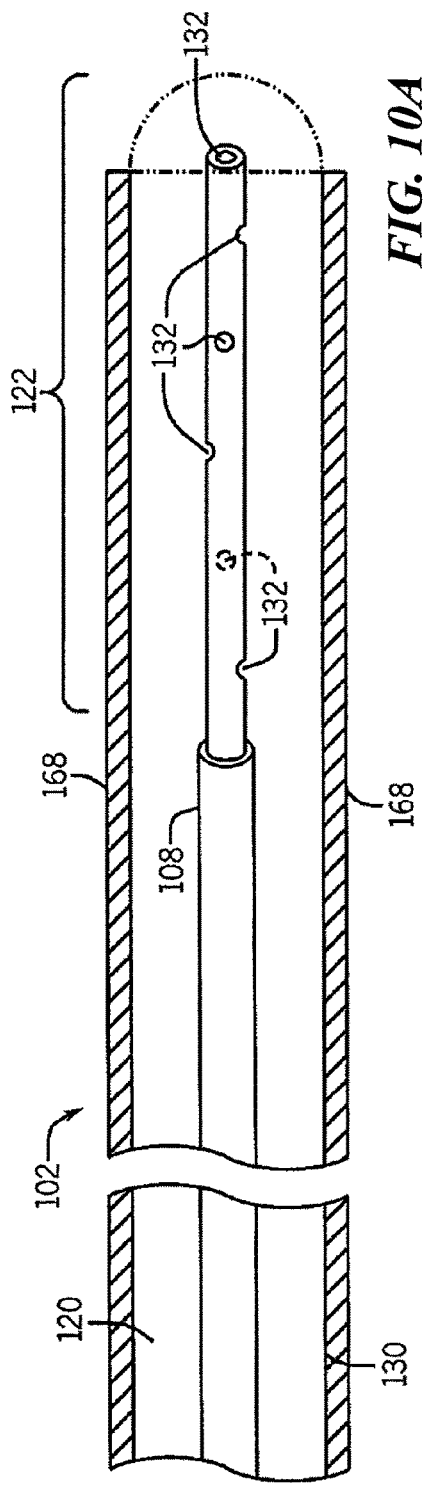
FIG. 10A is a partially schematic view of another embodiment of a cryo-applicator region suitable for continuous ablations configured in accordance with an aspect of the present disclosure.
Figure 10B:
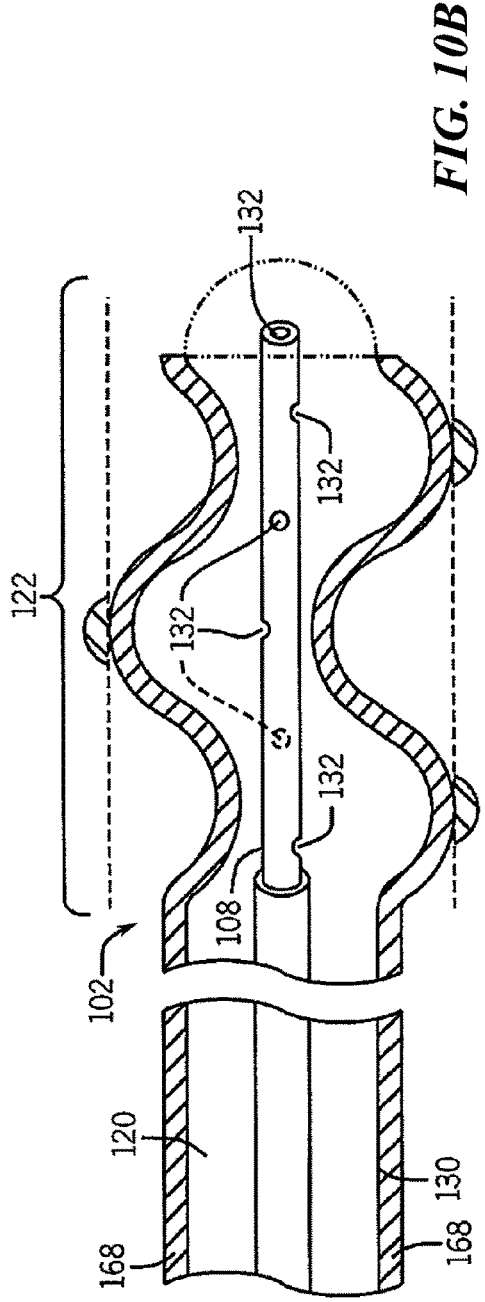
FIG. 10B depicts the cryo-applicator region of FIG. 10A in a deployed state.

Similarly, FIGS. 10A and 10B depict cross-sectional views of another implementation in which the applicator region 122 is initially deployed in a straight configuration (see FIG. 10A). However, in this implementation, the applicator region 122 is restrained in the straight or slightly bent configuration by the presence of a delivery sheath 168 or other external cover. Once at or near the target site, a delivery sheath 168 may be partially removed (see FIG. 10B) such that a natural bias or tension in the applicator region 122 is no longer resisted. In the absence of the resistance provided by the delivery sheath 168, the applicator region 122 may assume a second configuration, such as a helical, looped or curved configuration, suitable for ablating a continuous strip of tissue in the renal artery 170, as discussed above. In the depicted embodiment, the supply lumen 108 is depicted as generally retaining its shape and configuration when the configuration of the applicator region 122 is altered.

By controlling the amount or extent of delivery sheath 168 which is removed, the user may determine the shape of the applicator region 122 or the extent of the applicator region 122 that is altered in shape or otherwise configured for use as an ablative surface. Further, in those embodiments in which a delivery sheath 168 is present, the delivery sheath 168 may be positioned so as to mask certain regions of the applicator region 122 that might otherwise apply cryogenic temperatures to the patient tissue. That is, the delivery sheath 168 may be used to configure or limit the extent of cryogenically active surface of the applicator region 122 by covering cold spots or regions on the applicator region 122 and thus limiting which cold spots to which the tissue is exposed.

In the depicted embodiments, multiple restriction orifices 132 allow the liquid refrigerant 106 to exit the supply lumen 108 at multiple locations along the length of the applicator region 122 to provide cooling along the length of the region 102. A suitable number of orifices 132 may be present to achieve the desired cooling profile and temperature uniformity along the surface of the applicator region 132. In certain embodiments, the orifices 132 in the supply lumen 108 may be spaced apart, such as approximately 5 mm. As will be appreciated, the spacing of the orifices 132 may also determine the uniformity of cooling along the applicator region 122 and/or may define discrete cold spots along the applicator region 122 where ablation actually occurs. For example, if the applicator region 122 is shaped to conform to a vessel wall (e.g., helical or curved) the orifices 132 can be located to direct the spray of refrigerant 106 toward those portions of the applicator region 122 which act as a contact surface.

While certain embodiments (see FIGS. 9A and 9B) may direct the refrigerant 106 in one direction against the inner wall of the applicator region 122 to create a generally continuous cold surface, in other embodiments the refrigerant 106 may be directed in different directions by different orifices 132 in the delivery lumen 108. In this manner the desired cooling profile on the surface of the applicator region 122 may be achieved. For example, depending on the shape assumed by the applicator region 122 at the target site, typically the orifices 132 will direct the refrigerant toward those portions of the applicator region 122 expected to contact the tissue at the target site. As will be appreciated, while the direction and location of refrigerant spraying has been discussed as a mechanism for achieving the desired temperature profile, in other embodiments, the composition or structure of the applicator region 122 may be selected to achieve the desired temperature profile and/or to define discrete cold spots. For example, the thickness of the wall of the applicator region 122 may be varied such that thicker regions are less thermally conductive.

In certain implementations where a linear applicator region is employed, the applicator region 122 may be formed as a polymer tube of a suitable polymer composition, such as a Pebax composition of low durometer, e.g., 40-72D. As will be appreciated, a polymer applicator typically has less thermal conductivity than metal so a temperature gradient across its thickness can be greater compared to that seen with a metal applicator. For example, a polymer applicator could incur a thermal gradient from an expansion chamber 134 to the outer surface of the applicator of about 25° C. more than a metal applicator resulting in a surface contact temperature of about −60° C. to about −65° C. when $N_2O$ is used as the refrigerant 106. Although this is not as cold as a metal applicator it may still be sufficient to cool the vessel wall 170 to a temperature of −20° C. or lower at a depth of 3 mm or deeper. In other embodiments, a thin flexible metal or a more thermally conductive polymer may be employed to form the linear applicator region to improve thermal conductivity and/or to reduce the contact temperature.

As described in these examples, the ablation achieved by way of a linear ablation applicator region, as discussed herein, can be linear, curved or spiral. Ablation coverage will be greater than with a point ablate applicator, as discussed above, and may allow a renal denervation treatment with only one application thus reducing procedure time and providing a more consistent ablation configuration that depends less on operator dependency compared to a point ablate applicator, which may utilize multiple ablations to achieve the same coverage and effect.

C. Tubular Loop Applicator Region

FIGS. 11A-12 are partially schematic views of cryo-catheter configurations in accordance with still further embodiments of the technology. In these embodiments, the applicator region 122 may be provided as a shaped loop 180 of tube, such as in a planar loop configuration. In other embodiments, however, other configurations (e.g., full or partial helices (See FIG. 12), arc segments, and other non-planar loops) may also be employed. In one embodiment, the looped applicator 180, when deployed, may form a small diameter loop (e.g., about 4 mm to about 10 mm in diameter). In one such example, the length of the material forming the loop of tube may be 10 mm to 35 mm. In certain embodiments, the plane of the loop applicator 180 is generally perpendicular to the shaft 130 of the cryo-catheter 108. In other embodiments, however, the loop applicator 180 can be at other suitable angles relative to the axis of the cryo-catheter 180.

In certain embodiments, a tubular loop 180 of material may be formed using a flexible material such that the loop of material may be retained within a delivery sheath 168 until positioned at the target site. Once at the target site, however, the delivery sheath 168 may be removed or retracted such that the loop of material is free to assume its unrestrained configuration (e.g., a loop shape) that touches the vessel (e.g., renal artery) wall 170 to induce lesion 172 formation at least at one point or along a curved extent along the wall 170. For example, in one embodiment, the looped applicator 180 region may be formed as a flexible tube that may be retained or restrained in narrower, non-loop configuration within a delivery sheath 168 but, once free of the delivery sheath 168 the tube may expand outward into a looped configuration. Alternatively, the looped configuration may be generated in response to actuation or manipulation of a control wire. In one embodiment, for example, the looped applicator region 180 can be made from a metal tube (such as using a metal with shape memory, e.g., a nitinol tube) or using a thin polymer tube (such as a polyimide or PEEK tube) with an outer diameter about 0.67 mm to about 1.0 mm or using a combination of metal and polymer, for example a metal coil or laser cut tube covered in a polymer.

One feature of embodiments including a metal tube is that such an arrangement is expected to combine the benefit of a metal material (i.e., superior thermal conductivity) with a flexible applicator region 122 capable of conforming to at least a portion of the interior wall of the renal artery 170. For example, a small diameter metal tube applicator (or possibly a polymer tube in other embodiments) may have an unrestrained shape that allows the deployed loop applicator 180 to make contact with a larger portion of an arterial wall 170 than a point ablate catheter.

As with previously discussed embodiments of the present technology, liquid refrigerant 106 is supplied via a supply lumen 108 running the length of the cryo-catheter 102. The supply lumen may, in certain embodiments, have an inner diameter of about 0.254 mm and an outer diameter of about 0.381 mm. In one embodiment, the refrigerant 106 exits an orifice 132 and expands to a gas within an expansion chamber 134 at the proximal end of the loop applicator 180. In another embodiment, the loop applicator 180 constitutes an expansion chamber, i.e. the refrigerant 106 exits an orifice 132 and expands to a gas within the loop applicator. The evaporated refrigerant 118 flows through the loop applicator 180 (that may have an inner diameter of about 0.381 mm or greater, such as between about 0.508 mm to about 0.5588 mm) absorbing heat along the length of the applicator then flowing into a return lumen 120 where it is exhausted out of the cryo-catheter 102. In one embodiment, a vacuum may be applied to the return lumen 120 (such as via a cryo-console 100 employing a vacuum pump 126) to decrease the pressure in the loop applicator 180 so the flow of gas is not restricted and to decrease the boiling temperature of the refrigerant.

In one embodiment, the entire length of the loop applicator 180 may be cooled to cryogenic temperature such that tissue ablation occurs in a continuous strip around a limited portion of the circumference of the vessel 170 or at least along those portions of the vessel wall that the looped applicator region contacts. In other embodiments, however, the loop applicator 180 may be configured not to form a continuous lesion 172 but to form a series of point or spot lesions. For example, the loop applicator 180 may be shaped so that is not in continuous contact with the arterial wall 170 along the full length of the loop applicator 180. In such an embodiment, lesions 172 would only form at those points where the loop applicator 180 contacts the artery wall 170. Further, in other embodiments more than one loop applicator 180 may be deployed at a time. For example, up to three or four loop applicators 180 as discussed herein, and having different shape configurations, linear placement, and/or radial placement relative to one another, may be deployed from a delivery sheath 168 for application of a cryogenic renal denervation treatment. In still further embodiments, a different number of loop applicators 180 may be used. Discrete, non-continuous lesions can be made by an applicator with insulated sections or with restriction orifices that are spaced apart to allow separate regions on the applicator of cryogenic temperatures.

D. Balloon Applicator

FIGS. 13A-39 illustrate a number of additional cryo-catheter configurations in accordance with additional embodiments of the technology. In these embodiments, the applicator region 122 may be provided as an inflatable or otherwise expandable cryo-balloon 124. For example, such cryo-balloons 124 may be single- or multi-wall, may be made from a material selected from a range of materials with various characteristics of elasticity and/or distensibility (for example polyurethane, nylon elastomers, other thermoplastic elastomers, polyethylene terephthalate, other thermoplastic polymers), and, in certain embodiments, may deploy to have a diameter from about 4 mm to about 10 mm and a length no more than about 15 mm (e.g., about 6 mm). In such embodiments, the refrigerant 106 may be delivered directly to the interior of the cryo-balloon, which acts as an expansion chamber 134, where the refrigerant 106 evaporates, thereby inflating the cryo-balloon 124 to a degree sufficient to contact at least part of the artery wall 170. The evaporated refrigerant 118 may then return down the shaft 130 of the cryo-catheter 102 via one or more return lumens 120. To the extent that a guide wire or delivery sheath may be employed in placing a cryo-catheter 102 employing a cryo-balloon 124 as the applicator 122, the guide mechanism may be selected so as to not include a metal braid or other wire components to reduce the risk of a wire compromising the cryo-balloon 124.

In certain treatment environments, particularly those where operating pressures might be high, it may be desirable to configure the cryo-applicator with a multi-walled (e.g., double-walled) balloon. In such configurations, a second wall provides redundancy in the event of the failure of the first balloon wall. While such configurations may help reduce the risk of device failure, they involve increased complexity in design and manufacture as well as increased cost.

Pressure may be monitored, controlled or limited to reduce the risk of balloon rupture. For example, a pressure sensor 112 can be located in the cryo-balloon 124 to measure the balloon pressure or in the console to measure the supply and/or return pressure. Monitored pressure can be used in a feedback control system to adjust the flow, or flow rate of refrigerant 106, or optionally the vacuum pressure on the return lumen 120, or optionally to adjust the flow rate of evaporated refrigerant 118. Alternatively, one or more mechanical release valves can be incorporated to maintain pressure in the supply below a desired amount. Alternatively, the cryo-balloon 124 may be configured for low-pressure use, i.e., the cryo-balloon 124 is not filled until full or tight but is instead only partially filled and not fully expanded. Alternatively, the cryo-balloon 124 may be configured to stretch when internal pressure is increased in order to contact a complete inner circumference of a vessel or to fully occlude a vessel.

Cryo-catheter embodiments comprising a single-walled cryo-balloon may be uniquely suited for ablation of renal sympathetic nerves from within a renal artery. Based on the refrigerant mass flow rate and lower operating pressure involved in cooling the renal artery wall and surrounding renal nerves, a single-walled balloon allows for the efficient removal of heat without compromising safety. Indeed, as described in greater detail below, in some instances a single-wall balloon can be more compliant than a multi-walled balloon, thereby accommodating different blood vessel diameters and minimizing the risk of over-distending such vessels.

In addition to the clinical efficacy and safety benefits associated with single-walled balloon embodiments, in some cases single-walled balloons may provide certain practical advantages over double-walled balloons. In some embodiments, for example:

1. Balloons are attached to a catheter shaft, typically at both ends, and that attachment point should form a reliable seal. The use of two balloons doubles the number of seals used to affix the balloons to a catheter shaft and increases the complexity of the design and the product's manufacture, while a single-walled balloon may be simpler to manufacture and assemble and may have fewer seals and thus less risk of a seal malfunctioning.
2. Expandable balloons may be delivered to the treatment site in a collapsed configuration and inflated/expanded once in place. A double-walled balloon may experience greater difficulty in expanding due to static friction between the two balloon walls. An even greater difficulty may arise when the balloons need to be collapsed for withdrawal. A single-walled balloon may expand and collapse with less difficulty.
3. For a double-walled balloon the space between the two balloons needs to be evacuated otherwise the space will form a natural insulation barrier. Providing a method to evacuate the space greatly complicates the catheter design, often at the expense of product reliability.
4. A double-walled balloon may create much higher thermal impedance than its single-walled counterpart therefore reducing the efficacy of the device. A single-walled balloon may be able to achieve lower balloon temperatures and maintain a more uniform wall temperature. A more uniform wall temperature is possible since there is not a concern of gaps in the contact between an inner and outer balloon wall. Such gaps could create areas of significantly higher thermal impedance.

It will be appreciated that the above-listed features are merely examples, and that single- or double-walled balloons configured in accordance with various embodiments of the present technology may not include one or more the foregoing features. Further, such single- or double-walled balloons may have one or more additional features not recited above.

In certain embodiments, such as those depicted in FIGS. 13A-16A, the distal end of the cryo-catheter 102 terminates with the balloon 124. Such a design can be used in a very short section of renal artery 170. For example, the inflated cryo-balloon 124 can have a length of 6 mm and be used in a renal artery that is as short as about 6 mm before bifurcating. Such embodiments may have other advantages in that a cryo-balloon 124 with only one opening only needs to be bonded to the shaft 130 at one location and that has less risk of leak compared to designs in which an inflatable tube is joined to a shaft 130 at both ends. For example, the bond can be made with a long bond surface to ensure the cryo-balloon 124 doesn't become separated from the shaft 130 or leak.

Embodiments comprising a balloon with only one opening may optionally comprise a collapsing wire 136 (as shown in FIG. 13B) which may be used to facilitate collapsing an expanded balloon following a treatment so it can be retracted in to a guide catheter. The collapsing wire 136 may be, for example, a wire and/or coil with a radiopaque, rounded tip with a diameter of about 0.014". The collapsing wire may be inserted through the exhaust lumen to the inner volume of the balloon and gently press an inner surface of a distal portion of the balloon to lengthen the balloon and decrease its diameter.

Figure 13C:
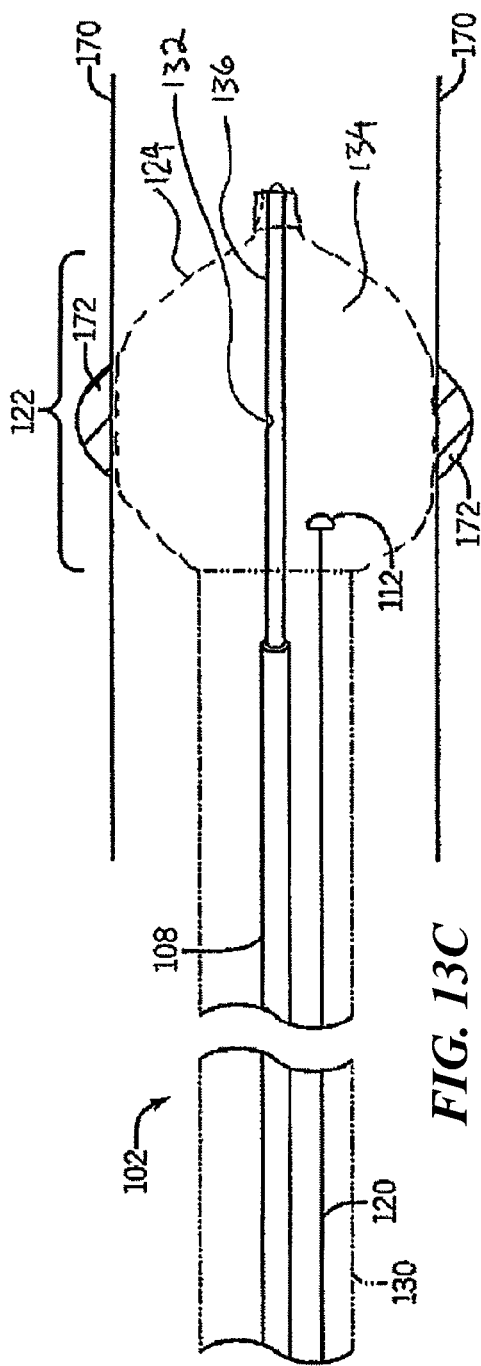

Embodiments comprising a balloon with two openings (such as a tubular balloon) may be sealed at a proximal end to the catheter shaft 130 and at a distal end to a collapsing wire 136. Collapsing wire 136 may be a separate wire or it may comprise a supply tube 180 or capillary tube (as shown in FIG. 13C). Collapsing wire 136 may be connected to an actuator in a handle 128 that move the collapsing wire 136 forward and/or twist it to lengthen and/or twist the balloon and decrease its diameter.

Figure 13D:
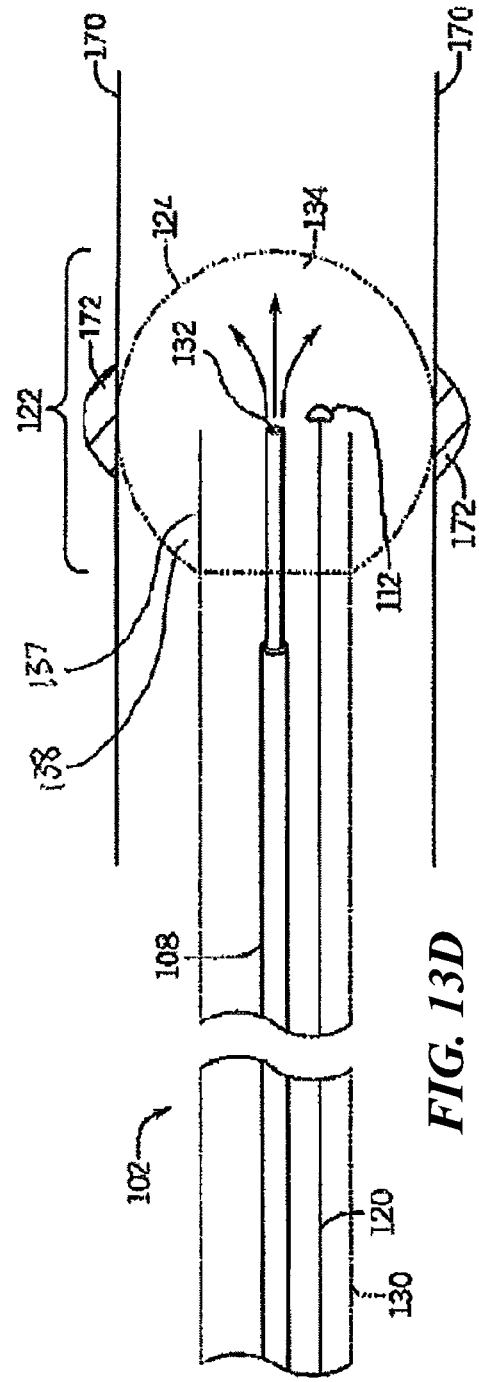

Embodiments comprising a balloon with only one opening may further optionally comprise an exhaust tube extension 137 (as shown in FIG. 13D) that extends the exhaust lumen partially in to the balloon. An exhaust tube extension 137 may reduce the risk of unevaporated liquid refrigerant from flowing into the exhaust lumen. If liquid refrigerant enters the exhaust lumen 120 it may increase the resistance of gas flow through the exhaust lumen increasing pressure in the evacuation chamber which could increase the boiling temperature of the refrigerant. An exhaust extension tube 137 may provide areas 138 for unevaporated liquid refrigerant to collect where it may subsequently evaporate before entering the exhaust lumen 120 via the exhaust tube extension 137. An exhaust lumen extension 137 may be made from the same material as the catheter shaft 130 or may be an additional material such as a polymer tube.

In the embodiments described with reference to FIGS. 13A-18B below, the deployed cryo-balloon 124 is configured to occlude the renal artery. For example, in embodiments in which the cryo-balloon 124 is sized to contact the full diameter of the vessel, a full circumferential ablation can be made. Though a single nozzle 132 is depicted, it will be appreciated that in certain implementations, additional nozzles 132 may be present or employed to achieve a full circumferential ablation. Further, nozzles for spraying the interior balloon surface can be shaped/arranged to create a desired pattern. For example, multiple pinhole nozzles can form patterns similar to ones seen with ink jet printers. Alternatively, in lieu of or in combination with one or more nozzles, narrow slits can be used to shape the spray in a way that facilitates linear ablation pattern. Still further, internal baffling can be used to further facilitate shaping of ablation patterns. Such baffles can be made, for example, of thin sheets of the balloon material and incorporated inside the balloon to direct the flow of the refrigerant inside at working sections of balloon.

Figure 14:
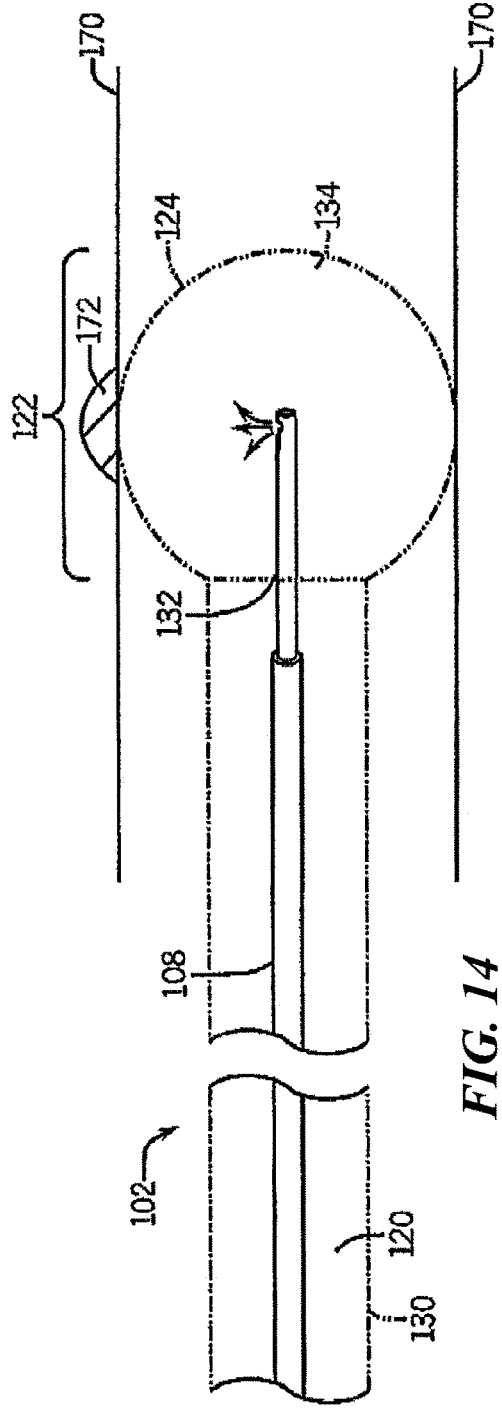
Figure 15:
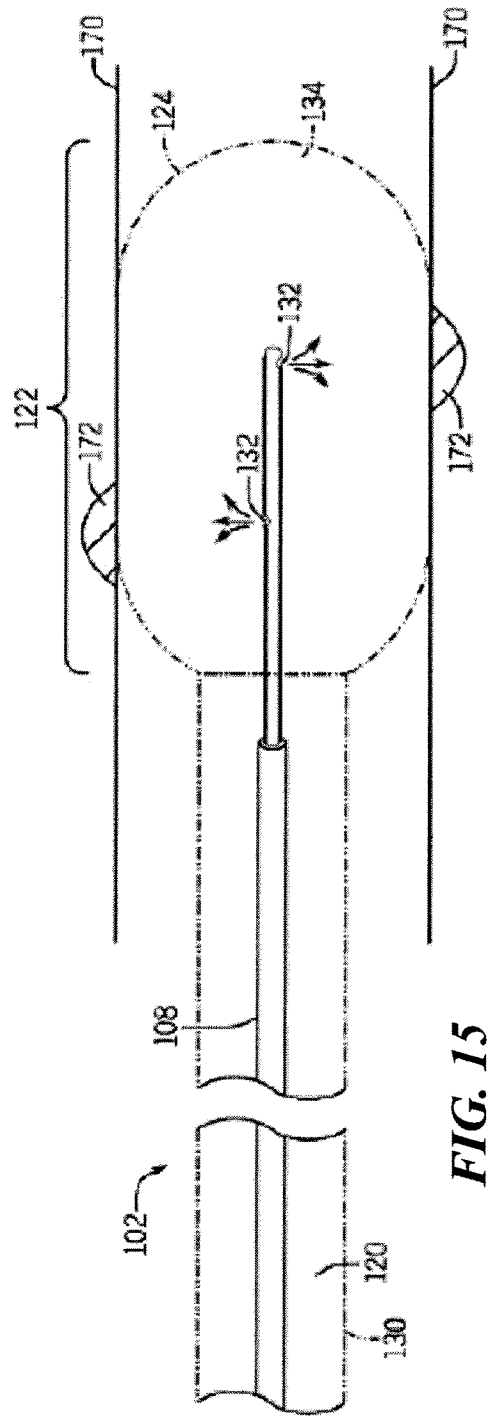

It should also be appreciated that less than a full circumferential ablation may be achieved using a fully occluding cryo-balloon 124. For example, as shown in FIG. 14, the nozzle 132 of the cryo-balloon 124 is directed to only one side of the cryo-balloon 124. A distinct and discreet cold spot may be generated at the location the refrigerant 106 is directed toward without forming cryogenically ablative temperatures across the entire surface or circumference of the cryo-balloon 124. In such embodiments, the cryo-balloon 124 may provide the benefits associated with the blocking of blood flow, as discussed below, while providing only a segmented or partial circumferential ablation, which may be desired in certain clinical contexts. Further, referring next to FIG. 15, in some embodiments additional orifices 132 can be provided that direct refrigerant 106 to linearly and/or radially spaced apart locations to create segmented, non-circumferential ablations, i.e., lesions 172, instead of a full circumferential ablation.

In the above-described cryo-balloon embodiments, the occlusion of blood can help to maximize refrigeration power while creating multiple, distinct ablations. Occlusion of blood can also advantageously remove the variable of blood flow and ablation depth can be more predictable. While vessel occlusion can help in cooling the tissue, it may also result in a challenge with respect to properly sizing the cryo-balloon 124 for the respective renal artery. Thus, various sized cryo-balloons 124 can be made available so an appropriate size can be chosen for a given patient. In some embodiments, for example, a balloon can be made from a polymer that can be stretched under moderately low pressure. For example, a balloon can expand from a nominal diameter (e.g., less than or equal to about 6 mm) with an internal pressure of about 1 atm to an expanded diameter (e.g., greater than the nominal diameter but less than or equal to about 9 mm) with an internal gauge pressure of about 2 or 3 atm. Thus a single-wall balloon can be deployed with a small increase in internal pressure to stretch and occlude a range of vessel diameters, for example between about 6 mm to 9 mm.

FIGS. 16A and 16B are partially schematic views of a cryo-catheter configured in accordance with another embodiment of the technology that occludes blood flow while creating less than a full circumferential ablation. The cryo-catheter 102 in this embodiment comprises a cryo-balloon 124 that contacts a partial circumference of the vessel 170 and an insulation balloon 1602 that contacts the remaining circumference of the vessel 170. The combination of both balloons 124 and 1602 occludes the vessel 170.

The insulation balloon 1602 may be inflated with non-cooling fluids (e.g., contrast, saline or $CO_2$) that are delivered through a separate insulation balloon supply lumen 1604. In other embodiments, however, the insulation balloon 1602 may be inflated using a different arrangement and/or different materials. In one embodiment, the cryo-balloon 124 may be made from a non-compliant material that may inherently have a stronger burst pressure, while the insulation balloon 1602 may be made from a compliant or semi-compliant material that can stretch to the size of the vessel 170. This combination is expected to mitigate some of the drawbacks associated with compliant balloons, while still being adaptable to variable vessel sizes. In other embodiments, the two balloons 124 and 1602 may be formed from different material and/or have a different arrangement relative to each other.

Figure 17A:
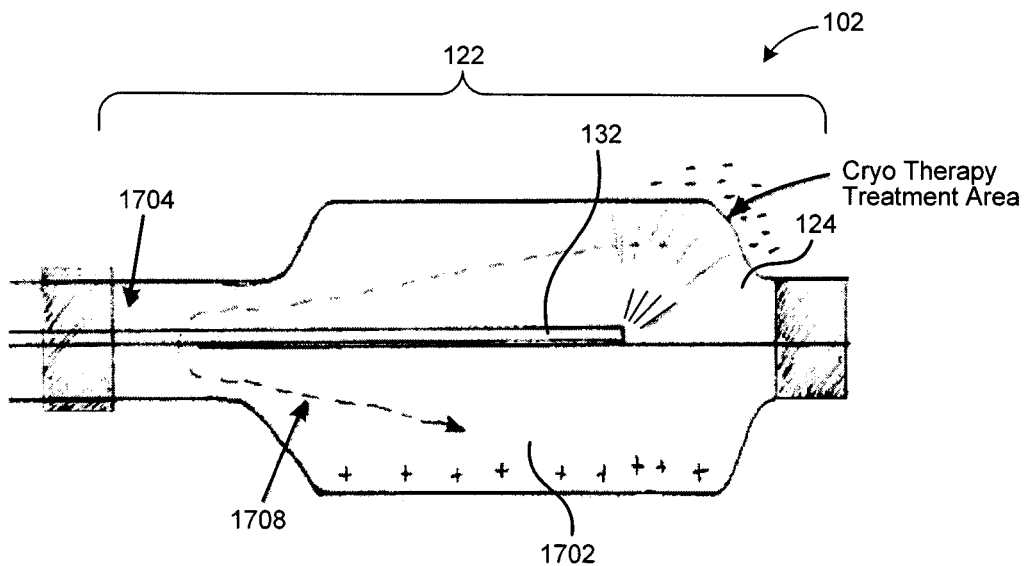
Figure 17B:
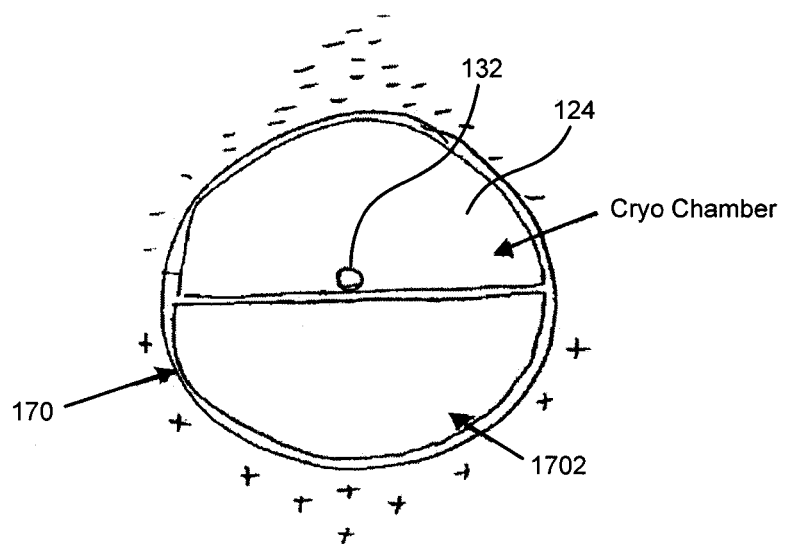

FIGS. 17A and 17B are directed to another embodiment of a cryo-catheter configured to occlude blood flow while creating less than a full circumferential ablation. Similar to the embodiment described above with reference to FIGS. 16A and 16B, the cryo-catheter of FIGS. 17A and 17B also includes both the cryo-balloon 124 and an insulating balloon 1702. In this embodiment, however, the insulating balloon 1702 is inflated with gas that is expanded in the cryo-balloon 124. In one embodiment, for example, liquid refrigerant enters the cryo-balloon 124 through the inflation lumen 132. Phase change (i.e., evaporation) occurs as the liquid refrigerant in the cryo-balloon absorbs heat. The gas exits the cryo-balloon 124 through the single chamber neck 1704 of the balloon 124 (as shown by gas path 1708). Some of the gas will also enter the insulation balloon 1702 and, although it may be cooler than body temperature, it will absorb much less heat than the cryo-balloon 124 because it is not experiencing a phase transition.

Figure 18B:
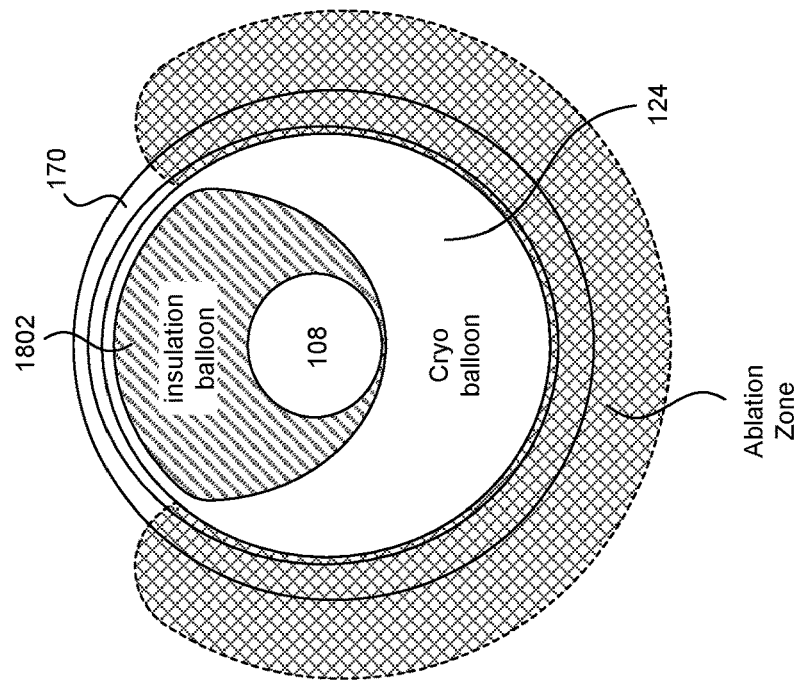
Figure 18A:
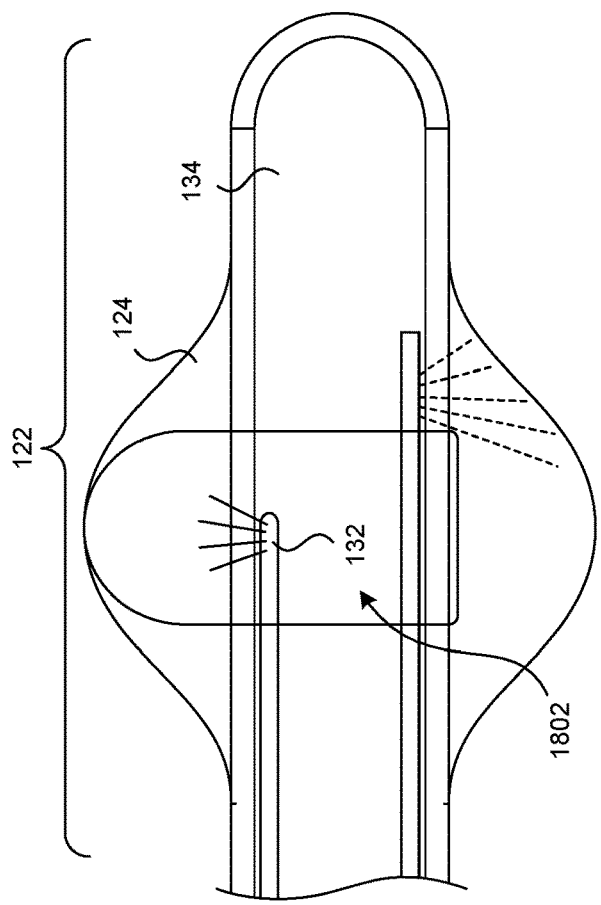

FIGS. 18A and 18B illustrate yet another embodiment of a cryo-balloon and insulation balloon combination. In this embodiment, an insulation balloon 1802 is contained within the cryo-balloon 124. The insulation balloon 1802 can be filled with a non-cryo fluid (e.g., $CO_2$) to a desired volume within the cryo-balloon 124 to prevent circumferential cryoablation. As best seen in FIG. 18B, for example, the ablation zone does not extend radially to the portion of the vessel 170 aligned with the insulation balloon 1802.

In any of the embodiments described herein, radio-opaque markers may be placed on, near, or in a cryo-balloon 124 to be to determine placement of the cryo-balloon. Such radio-opaque markers may include markings made using radio-opaque ink or radio-opaque structures attached to the surface of the cryo-balloon 124 or on the shaft. In order to determine if an occlusive balloon is fully occluding a vessel and making contact with the wall a burst of contrast can be injected from a delivery sheath 168 proximal to cryo-balloon 124. The contrast will flow between the cryo-balloon 124 and the vessel wall 170 if the vessel is not occluded. If the vessel is fully occluded, the contrast will not flow through the artery past the cryo-balloon 124. Radio-opaque markers and/or contrast can be visualized with fluoroscopy or other suitable radiographic techniques. Alternatively, a cryo-catheter with a cryo-balloon can be made to be compatible with magnetic resonance imaging (MRI) technology so a procedure can be done using MRI to visualize placement of the cryo-catheter as well as tissue changes and ice formation.

Figure 19A:
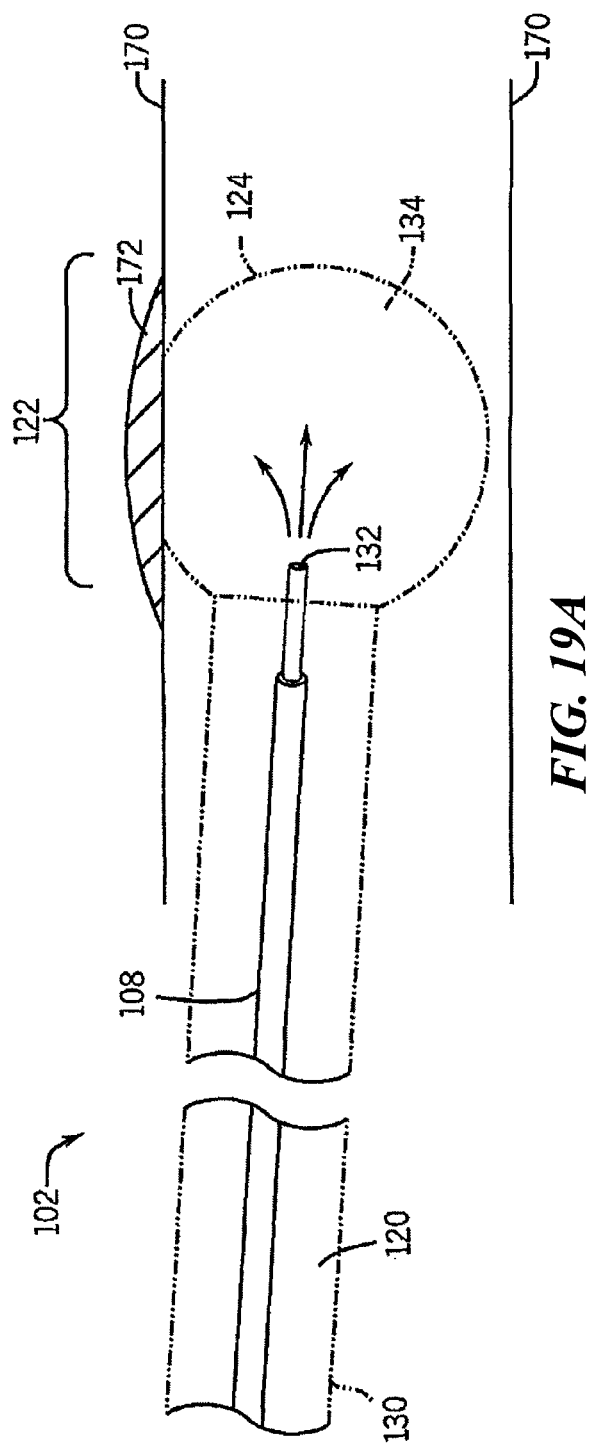
FIG. 19A is a partially schematic view of one embodiment of a cryo-applicator region in the form of a non-occlusive balloon configured in accordance with an aspect of the present disclosure.

FIG. 19A is a partially schematic view of a cryo-catheter configured in accordance with another embodiment of the technology in which the cryo-balloon 124 is smaller than the vessel diameter when inflated (and, thus, not occlusive). The cryo-balloon 124 is configured to be directed or deflected against the wall 170 of the renal artery (e.g., via controllable deflection). In one embodiment, the distal end of the catheter shaft 130 (about 30 mm or less) may be controllably deflected in one or multiple directions. The limited extent of contact between the cryo-balloon 124 and the vessel wall 170 results in a partial circumferential ablation, i.e., lesion 172 is formed at the point of contact, which is less than an inner circumference of the vessel. Subsequent to the formation of a partial circumferential ablation, the cryo-balloon 124 can be linearly and/or radially displaced to contact a different portion of artery wall 170, and an additional ablation formed if desired.

Figure 19B:
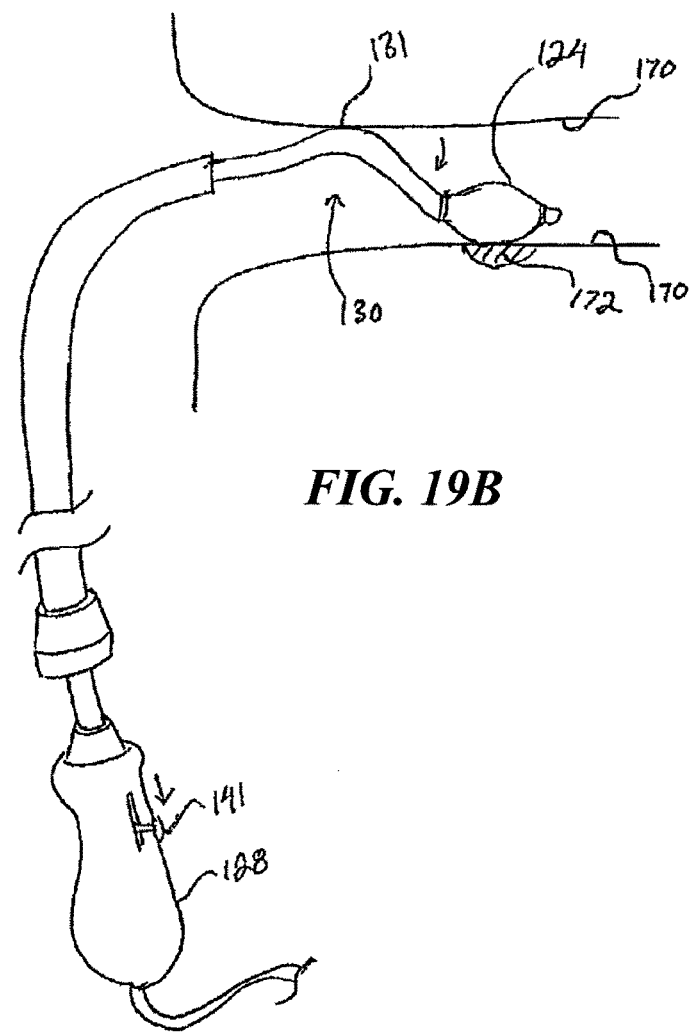
FIGS. 19B and 19C are partially schematic views of a further embodiment of a cryo-applicator region comprising controllable deflection in accordance with an aspect of the present disclosure.

Controllable deflection may be achieved through the actuation of a control wire to deflect the distal end region of the catheter shaft 130. A distal end of the control wire may be connected to a distal a flexibly biased member (e.g., a laser cut spine or a flexibly biased spine) positioned in the distal end region and a proximal end of the control wire may be connected to a deflection actuator 141 disposed in a handle 128 wherein when the deflection actuator is actuated tension is applied to the control wire compressing the flexibly biased member causing it to deflect in a predetermined biased direction. Deflection helps position the cryo-applicator 124 (e.g., cryo-balloon, metal tip, polymer cryo-applicator) in contact with the vessel wall (as shown in FIG. 19B). This is particularly useful when the distal end region 130 of the cryo-catheter 102 is delivered into the renal artery, as shown in FIG. 19B. Due to the curve and placement of a renal guide catheter and orientation of the cryo-catheter 102, the distal end region 130 of the cryo-catheter 102 is oriented up against the superior region of the vessel wall when first delivered into the renal artery. As shown in FIG. 19B, the operator may deflect the distal end region 130 via the actuator 141 to position the cryo-applicator 124 into contact with the vessel wall 170 at a more inferior location, This deflection of the distal end region 130 establishes wall contact and provides a stabilizing force between the cryo-applicator 124 and vessel wall 170. The operator can then initiate treatment at this generally inferior (bottom) location or rotate the treatment device for an alternate treatment location.

The active deflection of distal end region 130 is facilitated by not only operation of actuator 141, but also contact between a curved region 131 of the distal end region 130 and a superior region of the renal artery. As shown in FIG. 19B, this contact region generally occurs at the apex of the bend 131 of the distal end region 130. This contact region is in radial opposition to the contact between the cryo-applicator 124 and vessel wall following deflection of the distal end region 130. The stabilizing force provided by the distal end region 130 to the cryo-applicator 124 is also facilitated by the opposing force at the contact region between the bend 131 and the superior surface of the vessel wall. Even when the operator rotates the cryo-catheter 102 to circumferentially reposition the cryo-applicator 124 this opposition contact will be maintained, but at a different circumferential position. It should be noted, however, that while having such opposition contact facilitates wall contact and the stabilizing force, it is not generally required to achieve contact between the cryo-applicator 124 and the vessel wall.

Figure 19C:
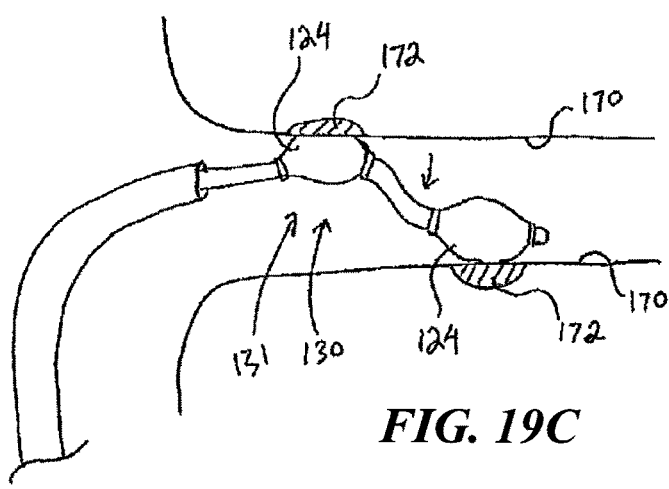
Figure 20:
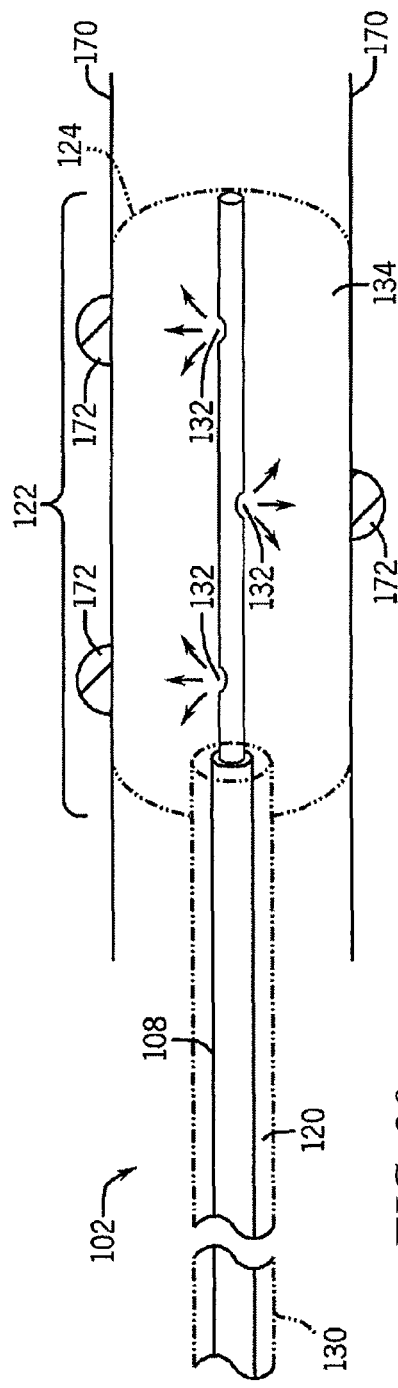
Figure 21:
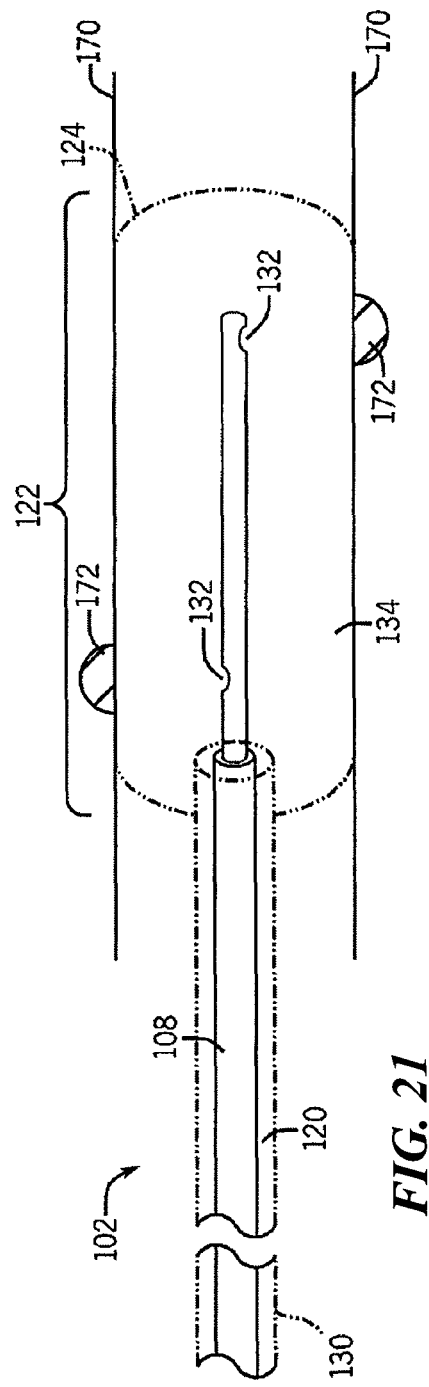

It certain embodiments (as shown in FIG. 19C) it may also be beneficial to equip the cryo-catheter 102 with a second cryo-applicator 124 at or in the vicinity of the bend 131. Placement of the second cryo-applicator 124 on or proximate to the bend 131 may enable the creation of an ablation 172 at or around the portion of the vessel wall that is in contact with the second cryo-applicator 124 at the bend 131). Activation of the cryo-applicators 124 would allow the operator to create two treatment zones that are circumferentially and longitudinally offset during a single placement.

As described above, the size and configuration of the distal end region 130 may play a valuable role in the positioning of the device for treatment and in facilitating contact between the cryo-applicators 124 and the vessel wall. The dimensioning of the distal end region 130 also plays a valuable role in this regard, particularly with respect to the constraints imposed by the renal anatomy. For example, the portion of the distal end region 130 that can be actively deflected may be less than or equal to about 30 mm long and the distal end can be deflected a maximum distance of no more than about 15 mm from the longitudinal axis of the elongated shaft when the actuator 141 is fully actuated.

FIGS. 20-24 are partially schematic views of cryo-catheters configured in accordance with further embodiments of the technology. In these embodiments, the cryo-balloon 124 may be positioned on the side of the shaft 130 of the cryo-catheter 102 and/or may be configured to generate multiple lesions 172 at a time. For example, referring first to FIGS. 20 and 21, a laterally placed cryo-balloon 124 is filled and cooled by multiple nozzles 132 which may direct refrigerant toward different surfaces or in different directions within the cryo-balloon 124. As depicted, the different axial positions cooled on the cryo-balloon 124 may result in discrete cold regions on the cryo-balloon 124 that may be used to form linearly displaced and radially offset partial circumferential ablations. Referring next to FIG. 22, separate delivery lumens 120 may be provided for one or more of the nozzles 132 used to deliver refrigerant 106 to the cryo-balloon 124. As a result, it may be easier to maintain pressure and cold temperatures for more distal nozzles 132 as little or no pressure differential should exist between such separately served nozzles 132. This may in turn can improve the efficacy and uniformity of the lesion formation process.

In the embodiment illustrated in FIG. 23, separate and discreet cryo-balloon 124 structures are provided on the cryo-catheter 102, with each separate cryo-balloon receiving refrigerant 106 via separate nozzles 132. Further, each cryo-balloon 124 and the respective nozzles 132 are fed by a separate delivery lumen 108 of refrigerant 106. Such an approach may allow separate and independent control to be asserted over each respective cryo-balloon 124, including whether a given cryo-balloon will be inflated and/or utilized. However, as will be appreciated, in other embodiments the respective separate cryo-balloons may be supplied using a common or shared delivery lumen 108. Further, though in the depicted embodiment each cryo-balloon 124 is only depicted as forming a respective partial circumferential ablation (i.e., lesion 172), it will be appreciated that in other embodiments some or all of the respective separate cryo-balloons 124 may actually generate a full circumferential ablation.

E. Additional Balloon Applicator Embodiments

FIGS. 24-35 are partially schematic views illustrating additional embodiments of the technology in which the cryo-applicator region includes an inflatable or otherwise expandable cryo-balloon assembly.

1. Non Compliant "Sized" Occlusive Balloon

Figure 24:
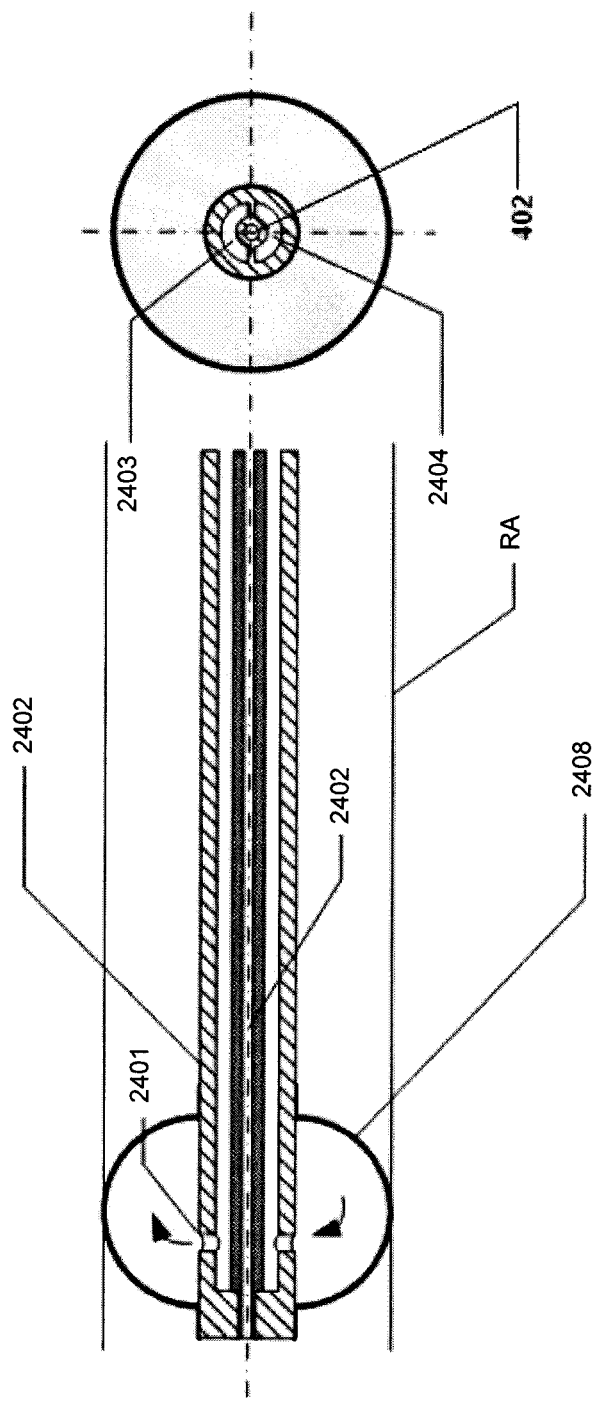

FIG. 24, for example, illustrates an embodiment of a cryo-catheter that uses a substantially non-distrainable and non-compliant balloon 2408 as a cryotherapy applicator. In this embodiment, the refrigerant is delivered via a supply lumen 2403 and the evacuation of vapor occurs via an evacuation lumen 2404. Cryo fluid is injected into the balloon via the nozzle 2401. As described below, the cryo fluid evaporates and expands to fill the balloon 2408, thus expanding the balloon to the inflated size limited by the material properties. The resulting geometry is predetermined by the non-stretchable material of the balloon 2408. Since the balloon surface is cooled by the emerging jet of cryo fluid and the balloon material is cooled by the evaporation of the refrigerant at the contact area, it may be desired to have several injection nozzles distributed around the circumference of the balloon. Alternatively, slits and multiple pinholes can be used to achieve the desired spray geometry. These nozzles, slits, and/or pinholes can be angled to directionally bias the spray and achieve uniform cooling across the cryotherapy applicator.

In one embodiment, a fluid refrigerant is used that transitions from a liquid state to a gaseous state as it expands into the balloon that is also the cryoelement chamber and cools the walls of the balloon 2408 that in turn contacts the walls of the renal artery RA. The walls of the balloon are sufficiently thin to produce minimum impediment to heat transfer.

One feature of the coaxial balloon design illustrated in FIG. 24 is the ability to position the catheter over a guidewire. Such a procedure generally requires less technical expertise and facilitates safer optimal catheter positioning within the vessel. The guidewire lumen 2402 in this embodiment is the central lumen of the catheter, but can be also offset from the center to accommodate other lumens and conduits. In the illustrated embodiment, the central lumen 2402 of the catheter shaft is reserved for the guidewire and can be used for contrast injection. For example, in some embodiments a rapid exchange system similar to angioplasty balloon catheters can be used. Such systems allow easier manipulation and rapid exchange of catheters over the shorter guidewire.

Another feature of certain embodiments of this arrangement is that when the balloon is inflated within the renal artery with the evaporated refrigerant, it transiently discontinues blood flow into the kidney, thus minimizing the extent to which convective and conductive heating from blood flow slows down cryoablation. Shorter procedure times are beneficial both for patient well-being and for increasing throughput.

The non-compliant occlusive balloon may be constructed of biocompatible materials such as Polyethylene terephthalate (PET), nylon, etc. Alternatively, the balloon may also be constructed from a metalized material, such as Mylar-type polymer film with thin metal layer deposited on its surface. The balloon diameter may range from 3 to 8 mm to provide a family of products. The length of the balloon may be fixed across all sizes or tailored for each size to account for heat transfer differences. For example, the length of a balloon suitable to fit in a renal artery and sufficient to apply desired cooling can be less than or equal to about 2 cm. In some embodiments the balloon length can be less than or equal to about 1 cm.

The catheter shaft can be extruded from Polyethylene (PE) or Polyethylene terephthalate (PET or PETE) material sufficiently strong to support the mechanical stress and internal pressure without kinking Refrigerant injection lumen can be reinforced by a thin wall resilient tube made from, for example, polyimide. For example, Raumedic in Leesburg, Va. manufactures a micro tube capable of 1200-psi pressure.

Braiding or coiling and/or coextrusion of several materials can be further used to reinforce the catheter shaft. Multiple-durometer sections of the shaft can be made to facilitate softer, less traumatic steerable or tethered tip that can be moved into position within the renal artery while the rest of the stiffer catheter shaft remains in the aorta.

This non-compliant balloon embodiment allows precise control of the balloon size and shape rather than relying on the controlled evaporation of the refrigerant to expand the balloon to the desired shape and size. The balloon is sized so that when inflated it does not substantially distend the walls of the artery.

The cryogenic balloon catheter of FIG. 24 operates as a closed-loop fluid circulation system. Coolant is fed to the catheter at a high pressure, and cryogenic cooling results from evaporation of the coolant resulting from a pressure drop as the cryogenic fluid is sprayed into the interior of a balloon at the catheter tip.

More than one injection nozzle can be incorporated in the catheter design to redistribute the refrigerant inside the catheter. To reinforce injection components of the design, metal or glass capillaries can be inserted into the catheter walls at the locations where the refrigerant is released into the expansion chamber.

2. Balloon with a Cryoelement

Figure 25:
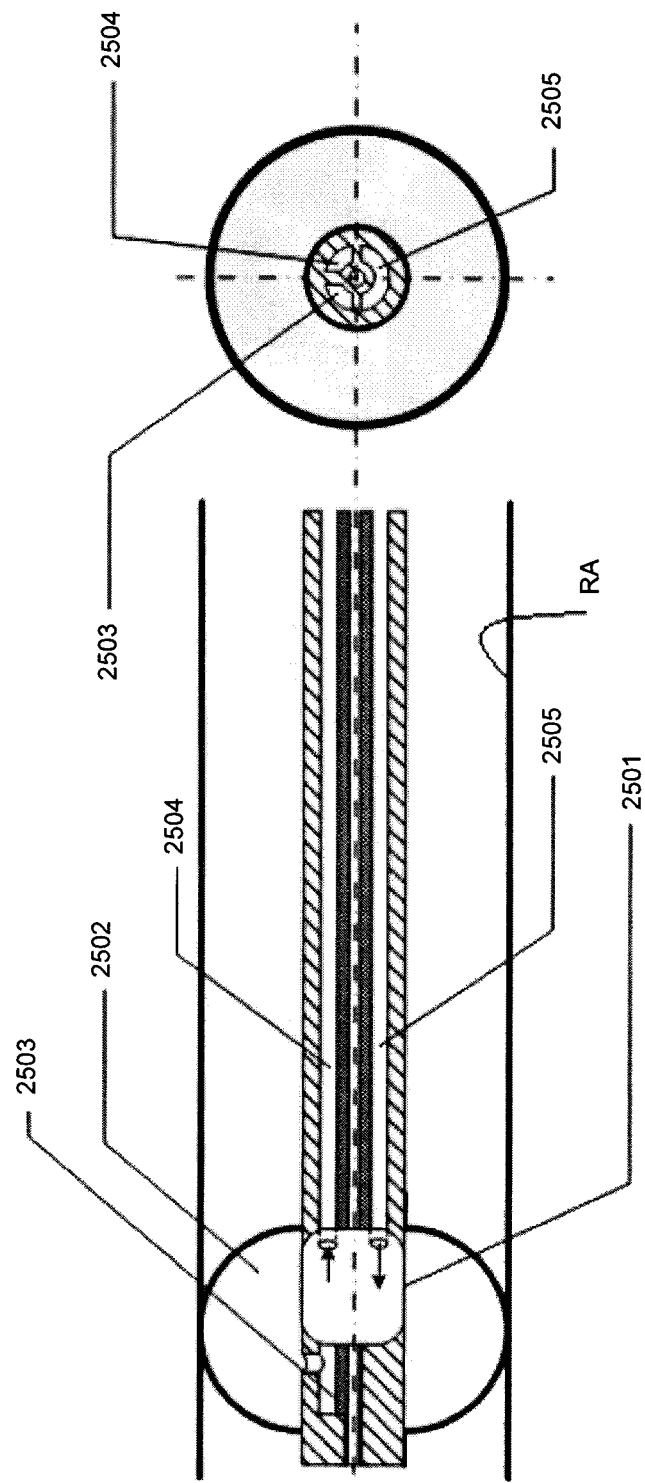

FIG. 25 illustrates another embodiment of a cryo-catheter configured in accordance with an embodiment of the technology. This embodiment employs a conduction balloon 2502 that can be a compliant or a non-compliant balloon designed to conduct cold to the wall of the renal artery RA. This conduction balloon 2501 is a cryotherapy applicator, but does not provide an evaporation chamber for the refrigerant. In this embodiment, a fluid refrigerant transitions from a liquid state to a gaseous state inside a cryoelement 2501 (e.g., a hollow chamber) and cools the walls of the cryoelement that are made of a material that conducts heat well, such as metal. The balloon 2502 in turn contacts the walls of the renal artery RA. The walls of the balloon are sufficiently thin to produce minimum impediment to heat transfer. The balloon can be filled with fluid that conducts heat from the arterial walls to the cryoelement and, accordingly, freezes the tissue surrounding the arterial wall. It is desirable that the fluid in between conduction balloon 2502 and cryoelement 2501 have a low freezing point to achieve a low temperature at the interface between the renal artery wall and conduction balloon 2502.

In the embodiment illustrated in FIG. 25, the catheter shaft has three internal channels: refrigerant injection channel tube 2505, vapor evacuation channel 2504, and balloon inflation channel 2503. In this example, the fluid refrigerant passes through the restriction tube (e.g., nozzle) 2505 and then expands into the chamber 2501 to cool the cryoelement walls. In one embodiment, a fluid refrigerant is used that transitions from liquid state to a gaseous state as it expands into the cryoelement chamber. With the balloon interposed between the cryoelement and the target tissue, cold conducting fluid (e.g. ethyl alcohol) is controllably pumped into the balloon causing the balloon to expand to the exact shape required. The fluid may also include contrast media. The fluid generally dwells in the balloon during the ablation time.

As mentioned above, the fluid used to fill the balloon 2502 should have a low freezing point since it is not desired to have an ice ball to conduct heat. While most liquids conduct heat well, ice is not a good thermal conductor. An example of fluid that has a low freezing temperature is ethyl alcohol. The freezing point of ethyl alcohol is −117.3° C. The amount of ethyl alcohol needed to fill the balloon in this embodiment may be less than 1 milliliter. This amount of ethyl alcohol, if released into the renal artery in the case of the balloon failure, is essentially harmless. Hence, ethyl alcohol presents a useful option in the event of balloon failure. The cooling of the cryoelement, in turn, cools the liquid in the balloon to a temperature of as low as −60 to −90° C. The resulting cold liquid inside the balloon extracts heat from surrounding tissue resulting in the cryoablation of a desired portion of tissue.

One feature of a non-compliant balloon is that such balloons have a known size when inflated and do not exceed the desired maximum size if over-inflated by mistake or as a result of failure. In other examples, however, a compliant balloon also may be advantageous for multiple reasons. For example, the high pressure inside a non-compliant balloon could cause injury to the blood vessel (e.g., overstretching or distension of the renal artery), particularly if the physician chooses the wrong balloon size. In another example, under sizing of the non-compliant balloon can result in ice formation between the balloon and the vessel wall that may reduce the effectiveness of cooling. Accordingly, it may be beneficial to offer multiple sizes of PET-style balloons to facilitate proper sizing. However, if a compliant balloon is employed, however, adequate sizing may be achieved with as few as 1 or 2 sizes. Compliant balloons may be constructed from a compliant inflatable membrane with elastomeric properties. Inflatable balloons may be formed of a urethane polymer or a thermoplastic rubber elastomer, such as Chronoprene™, commercially available from CardioTech International, Inc.

When inflated, the cryoballoon comes into contact with a substantial segment of the internal wall of the renal artery. The inflated cryoballoon has a diameter substantially larger than the diameter of the catheter shaft and approximately equal, slightly below (undersized) or slightly above (oversized) the internal diameter of the renal artery segment targeted for renal cryomodulation. An undersized balloon may benefit from being biased against the vessel wall to achieve the desired effect of cryoablation.

3. Non Occluding Balloon Urged Against the Arterial Wall

Figure 26:
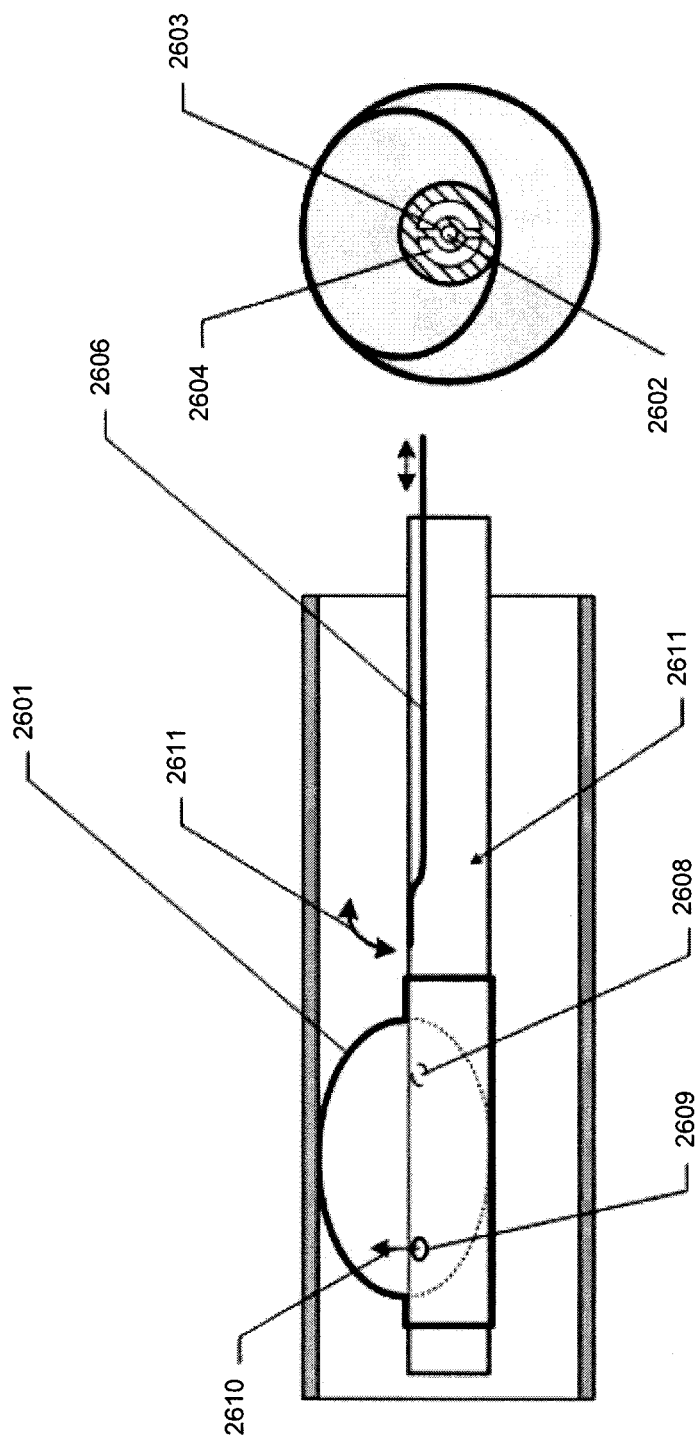

As discussed above, one proposed method of performing renal denervation via cryoablation involves creating one or more lesions that are less than 360° at any one cross section. Devices suitable for creating several non-circumferential segment lesions can be designed based on a non-occlusive or occlusive non-compliant cryoballoon element. FIG. 26, for example, illustrates an embodiment of a cryo-catheter configured in accordance with an embodiment of the technology where a non-occluding (i.e., not fully occluding the lumen of the artery) balloon is pressed against the wall of the renal artery to create less than circumferential segmented ablation of renal nerves proximate to the renal artery.

In one embodiment, the cryoballoon 2601 diameter is sized substantially smaller than the renal artery cross-section (3-8 mm) but larger than the shaft 2611 of the catheter (2 mm). In this embodiment catheter distal segment (approximately 1-3 cm length) can be deflected 611 using a deflection mechanism such as a pull wire 2606 mechanism that transmits torque from the operator held catheter handle (not shown). Deflection of the distal segment urges the cryoballoon 2601 against the arterial wall to facilitate the creation of lesion. At the same time blood flow in the renal artery may not be completely interrupted during the procedure.

To optimize efficiency of the cryotherapy, direct contact between the surface of the cryoballoon and the arterial wall is desirable. If a layer of ice is formed between the surface of the cryoapplicator (e.g. balloon) and the target tissue the tissue may not be successfully destroyed since ice is not a good thermal conductor.

The balloon can be an asymmetric balloon to further optimize volume of cryogenic fluid inside and to reduce the cross sectional diameter/profile. Alternatively, the non-occluding balloon can be a spherical balloon centered on the shaft of the catheter but substantially smaller, when fully inflated, than the cross section of the renal artery.

To further facilitate effective cooling of the area of the balloon surface that is pressed against the arterial wall, the jet of cryo fluid 2610 can be directed to the inner wall of the balloon 2601 that is urged against the arterial wall. The catheter shaft 2611 is shown equipped with at least one tube for the injection of the refrigerant 2604 and one tube for the evacuation of vapor 2603 and the guidewire lumen 2602.

This lopsided "blister" balloon can be manipulated by rotation of the shaft from the outside of the body to reposition and create sequential lesions that can be for example 90° to 180° segment lesions spaced 3 to 5 mm along the arterial trunk. For example a 360° lesion that is 2 mm wide will have surface area of 31.4 to 37.7 mm$^2$ if the diameter of the artery is 5 to 6 mm.

Other mechanical means (i.e., biasing members) can be implemented to urge the balloon against the wall (e.g. expandable members such as a metal wire basket or a collapsible braid structure opposite the balloon). For example, cryoballoon can be also offset by a second, regular non cryogenic inflatable balloon mounted on the same catheter shaft. In another example, multiple configurations of actively urged or self expanding (such as using shape memory alloys such as nitinol) biasing members may be implemented in other embodiments. Common to these designs a cryoapplicator is an expandable member mounted on the distal segment of the catheter. The cryoapplicator balloon when expanded does not fully occlude the renal artery. The catheter is equipped with means to direct and urge the cryoapplicator towards the inner wall of the artery.

Figure 27:
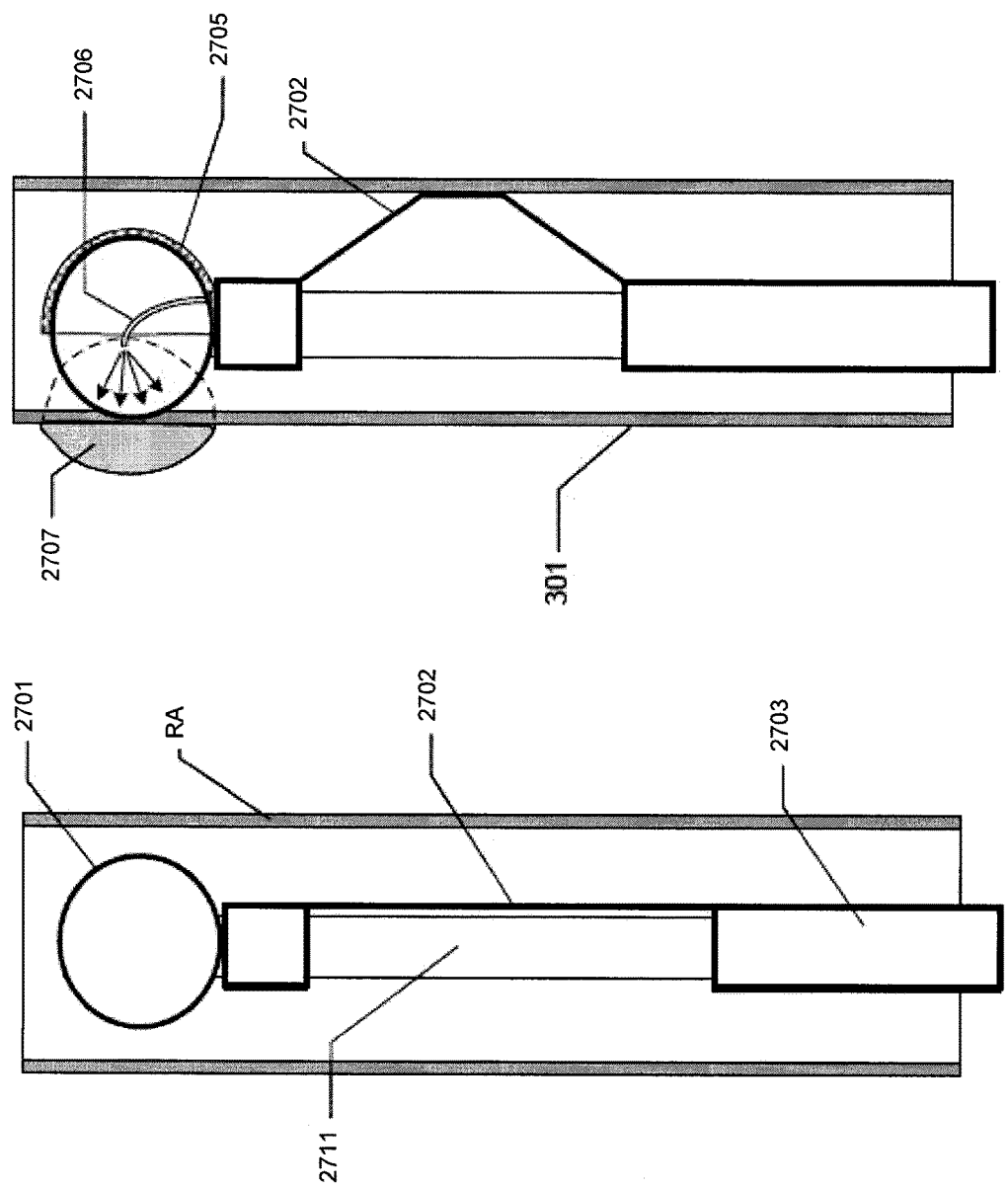

FIG. 27 illustrates another example of a balloon 2701 that is smaller in diameter than the renal artery RA. During cryoablation, the balloon 2701 can be urged against the wall of the renal artery RA by the expandable member 2702. The expandable member is expanded by the forward motion of the sliding sheath 2703 that overlaps the catheter shaft 2711.

In this example, the balloon 2701 can be a complaint or a non-compliant balloon. The balloon 2701 as shown is both the cryotherapy applicator and an evaporation chamber for the refrigerant. Refrigerant is sprayed out of the nozzle 2706 and directed towards the part of the balloon in contact with the arterial wall where it creates a segmented lesion 2707 around the inner circumference of the artery that is less than 360°. After the lesion is made, the catheter can be retracted or advanced (e.g., approximately 2-5 mm), and/or rotated (e.g., 45-180°) in order to reposition the cryoballoon and create a second segmented lesion. Multiple segmented lesions can be created at distinct locations within the renal artery to ablate a substantial portion of the internal circumference along a longitudinal length of the artery without creating a continuous circumferential ablation. Heat insulation layer 2705 can be applied to the blood exposed surface of the cryoballoon 2701 to reduce losses of refrigeration power and ice formation.

As with the device described above with reference to FIG. 25, balloon 2701 can be a heat conduction balloon used as a cryotherapy applicator but not as an evaporation chamber for the refrigerant. In such embodiments, a fluid refrigerant transitions from a liquid state to a gaseous state inside a cryoelement chamber and cools the walls of the cryoelement that are made of a thermally conductive material (e.g., metal). The balloon 2701 in this case can be filled with heat conducting media (e.g. ethyl alcohol).

4. Segmented Lesion Balloon with Circumferential Lobes

Figure 28:
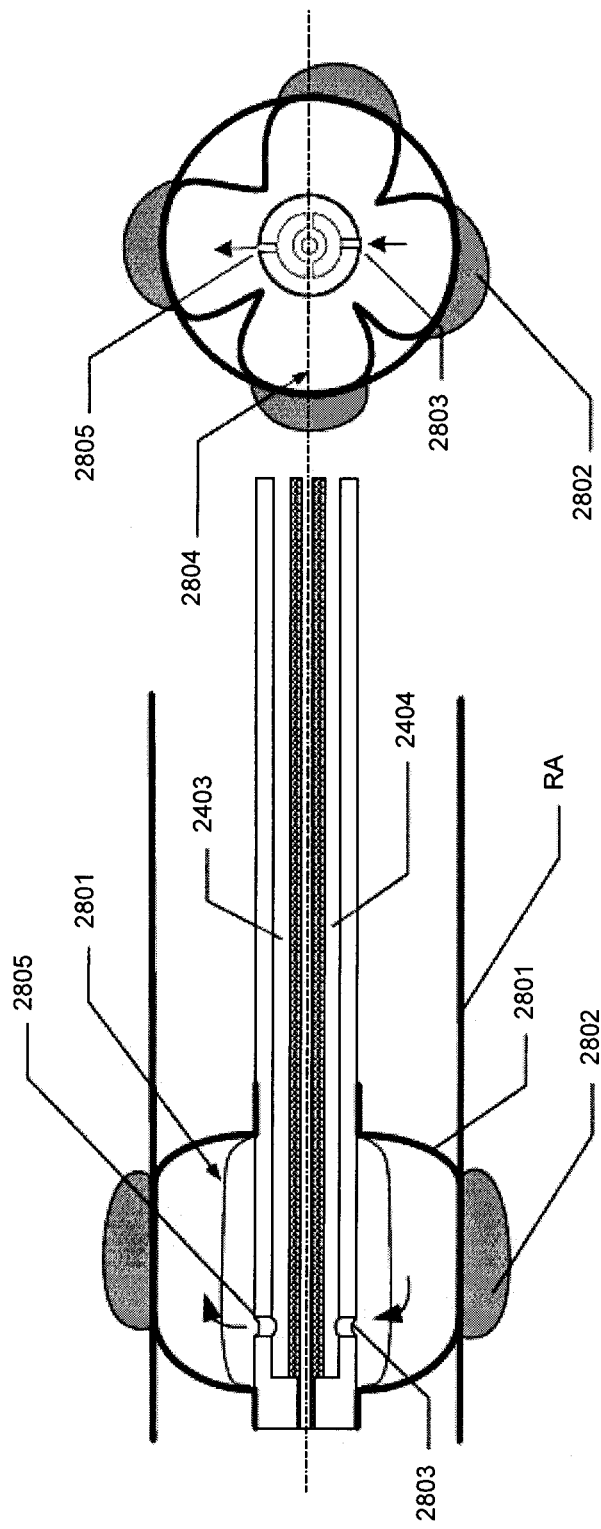

FIG. 28 illustrates a cryo-catheter designed to create non-continuous segmented lesions using a non-compliant shaped balloon 2801 in accordance with an embodiment of the technology. To enable multiple non-continuous circumferential lesions the balloon can be molded into a segmented shape. Segments create partial contact with the vessel wall sparing some of the inner surface of the renal artery RA. In this embodiment, a substantially non-distrainable and non-compliant balloon may be used as a cryotherapy applicator. The refrigerant is delivered to the balloon 2801 via the lumen 2403 and the evacuation of vapor occurs via the lumen 2404. Multiple refrigerant injection nozzles and vapor evacuation ports can be envisioned to facilitate tissue cooling and folding and unfolding of the balloon.

In this embodiment, cryo fluid is injected into the balloon via a nozzle 2805 and fills the balloon 2801 to expand the balloon to the inflated size and shape. The resulting geometry is predetermined by the non-stretchable material of the balloon. Since the balloon surface is cooled by the emerging jet of cryo fluid and the balloon material is cooled by the evaporation of the refrigerant at the contact area it may be desirable to have several injection nozzles distributed around the circumference of the balloon. The fluid spray from the nozzle 2805 is directed to the surface of the balloon lobe that contacts the wall of the artery. Vapor is evacuated via the port 2803. Segmentation may have an additional advantage when folding of the balloon occurs.

In one embodiment, a fluid refrigerant is used that transitions from a liquid state to a gaseous state as it expands into the balloon that is also the cryoelement chamber and cools the walls of the balloon 108 that in turn contacts the walls of the renal artery RA. The walls of the balloon are sufficiently thin to produce minimum impediment to heat transfer. In this embodiment four individual longitudinal lobes 2804 of the shaped balloon create four lesions 2802 that are intended to penetrate the adventitia of the renal artery. The segmented balloon creates segmented lesions 2802 that are less than 360° each, but form an interrupted circumferential pattern. For example, the segments can be coaxial with the catheter shaft or angled as propeller blades to enable better coverage of the vessel circumference. In still other embodiments, the segments can have other arrangements. After the lesions are made, the catheter can be advanced or pulled (e.g., 3-10 mm), rotated (e.g., 35-55°) and another segmented lesions can be made thus following an overlapping pattern. Heat insulation layer can be applied to the blood exposed surface of the cryobaloon to reduce losses of refrigeration power.

The segmented balloon can be formed through blow molding, a process that uses heated mold and compressed air to mold and shape the balloon into its correct form. Examples of the materials that can be used for segmented molded balloons are polyethylene terephthalate (PET) or nylon.

When the balloon is inflated within the renal artery with the refrigerant gas, it transiently reduces but may not completely discontinue blood flow into the kidney, thus minimizing the extent to which blood flow slows down cryoablation but possibly maintaining some perfusion of the kidney. Further, a segmented balloon as shown in FIG. 28 can be modified to enable better coverage of the internal surface of the artery while reducing the possibility of structural damage to the vessel wall and "ring" type stenosis.

5. Segmented Lesion Balloon with Longitudinal Lobes

Figure 29:
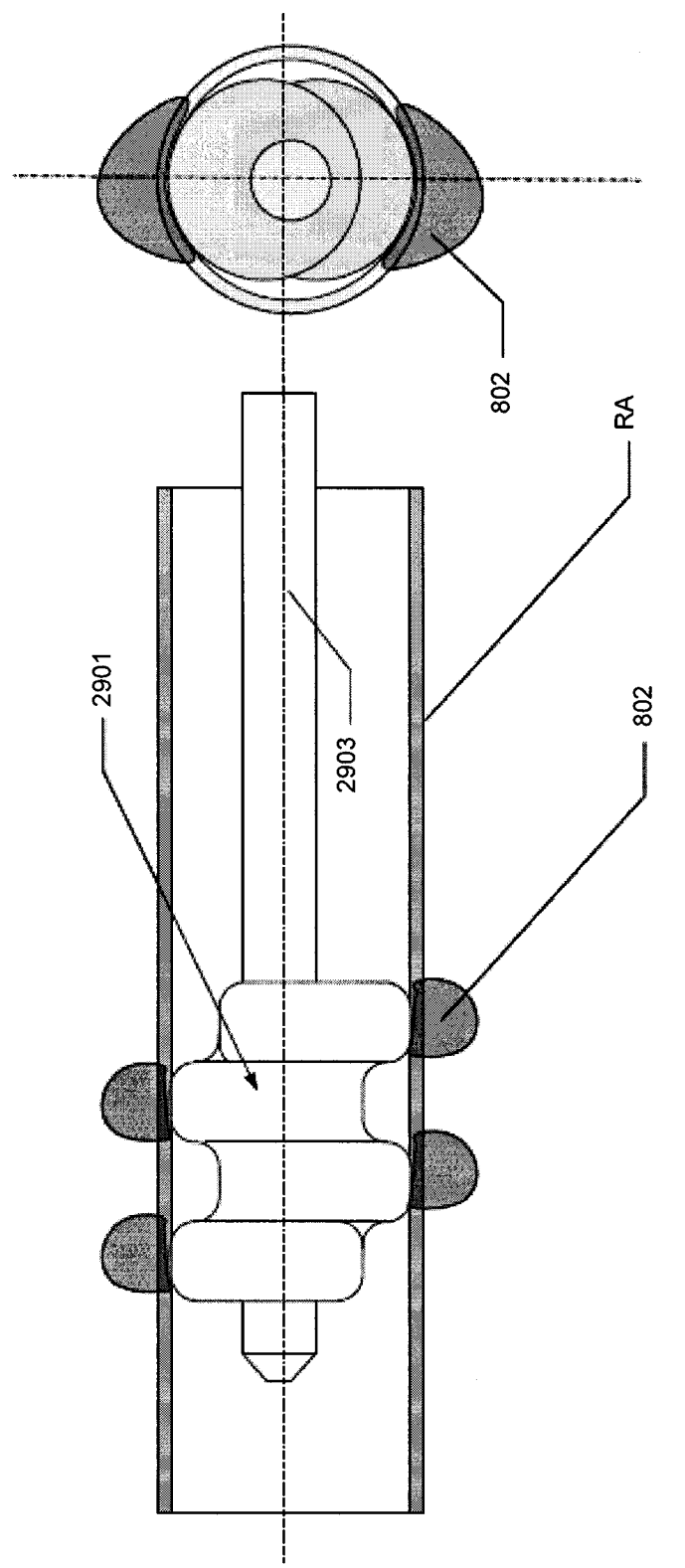

FIG. 29 illustrates a shaped balloon that can be used to create offset or stacked non-continuous circumferential lesions in segments in accordance with another embodiment of the technology. The balloon 2901 is molded with a shape having several offset segments and mounted on the catheter shaft 2903. Lesions 2802 are created in the areas of the vessel where the balloon lobes approximate the vessel wall RA. This balloon resembles a crankshaft in three dimensional space. Other balloon shapes such as an Archimedes screw or a worm gear shape can be envisioned to serve the same purpose as the crankshaft balloon.

In several embodiments, the catheter assemblies described above include at least one tube for the injection of the refrigerant and one tube for the evacuation of vapor integrated with the catheter shaft (not shown). The injection tube can have several nozzles (not shown) for injection of liquid refrigerant into the balloon. These nozzles are designed to direct the spray of the refrigerant towards the inner surface of the balloon in the locations where the balloon is expected to contact the wall of the vessel such as in the areas where lesions 802 are shown.

6. Helical Balloon

Figure 30A:
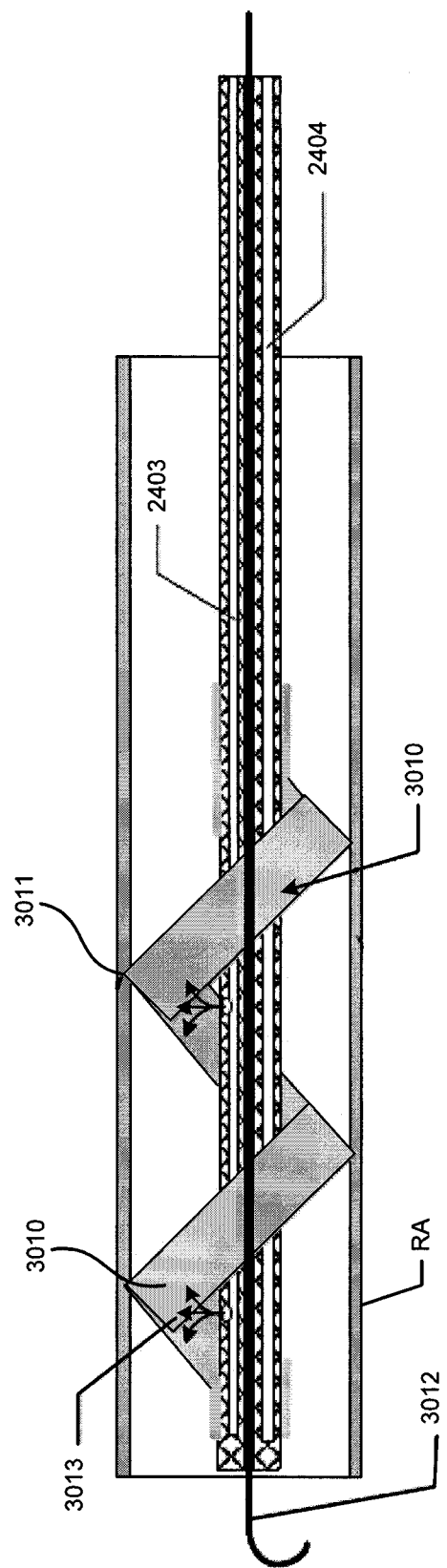

FIG. 30*a* illustrates an alternative geometry of a shaped balloon 3010 mounted on a distal segment of a catheter in accordance with still another embodiment of the technology. This embodiment includes at least one flexible thin wall tube for the injection of the refrigerant 2403 and one tube for the evacuation of vapor 2404 integrated with the catheter shaft. In the center of the catheter, a guidewire 3012 is shown extended into the vessel. In this embodiment, the balloon 3010 is formed in a shape of a corkscrew. This arrangement is expected to allow blood to flow through the vessel RA. A number of nozzles are positioned along the length of the balloon 3010 and designed to distribute spray 3013 of the refrigerant to target tissue. For example, where a surface 3011 of the balloon contacts the vessel wall RA, a spiral lesion is expected to be formed.

Figure 30B:
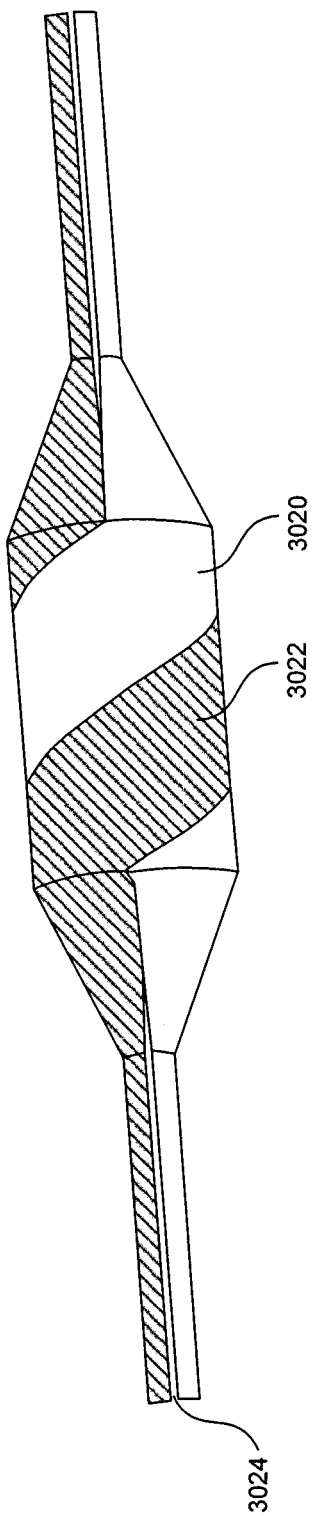

In some embodiments, a helical shaped cryo-balloon may be configured with a space between helical revolutions. FIG. 30B, for example, is a partially schematic view of a cryo-applicator region including two shaped balloons 3020 and 3022 mounted on a distal segment of a catheter in accordance with another embodiment of the technology. The first balloon 3020 can be a helical cryo-balloon generally similar to the shaped balloon 3010 described above with reference to FIG. 30*a*. The second balloon 3022 comprises an insulative helical shaped balloon that is aligned with the first balloon 3020 such that the second balloon 3022 fills the gap between revolutions of the first balloon 3020 so blood flow through a vessel in which the device is placed is occluded. In the embodiment illustrated in FIG. 30B, there is a gap 3024 between the first and second balloons 3020 and 3022 along at least a portion of the distal segment of the catheter. In other embodiments, however, the first and second balloons may have a different arrangement relative to each other.

7. Cryoadhesion and Tethered Cryo Balloons

In some instances, cryoadhesion can be an attractive aspect of vascular cryotherapy because it facilitates consistent contact between the cryoapplicator and tissue in the setting of moving tissue as a result of patient's motion and normal respiration. Conversely, cryoadhesion may create a risk of denuding or severely disrupting the artery if the catheter moves and puts traction on the adhered tissue. This risk presents a design consideration for maintaining vessel integrity and safety by minimizing torque or traction on the catheter shaft to avoid dissection or disruption of the arterial wall that are temporarily bonded to the balloon.

A catheter can be equipped with a tether feature to prevent motion from being translated from the shaft to the balloon. For example, the catheter shaft can be inserted into the renal artery while stiffened by a stylet or a resilient wire that is later withdrawn after positioning of the balloon. The catheter can be equipped with a spiral shaft or intentionally kinked shaft that can absorb motion without translating it to the balloon. Other ways to avoid moving a balloon that is bonded to tissue include a flexible connection between the balloon and catheter shaft and structures that hold the treated portion of the artery still with respect to the balloon or catheter shaft.

Figure 31:
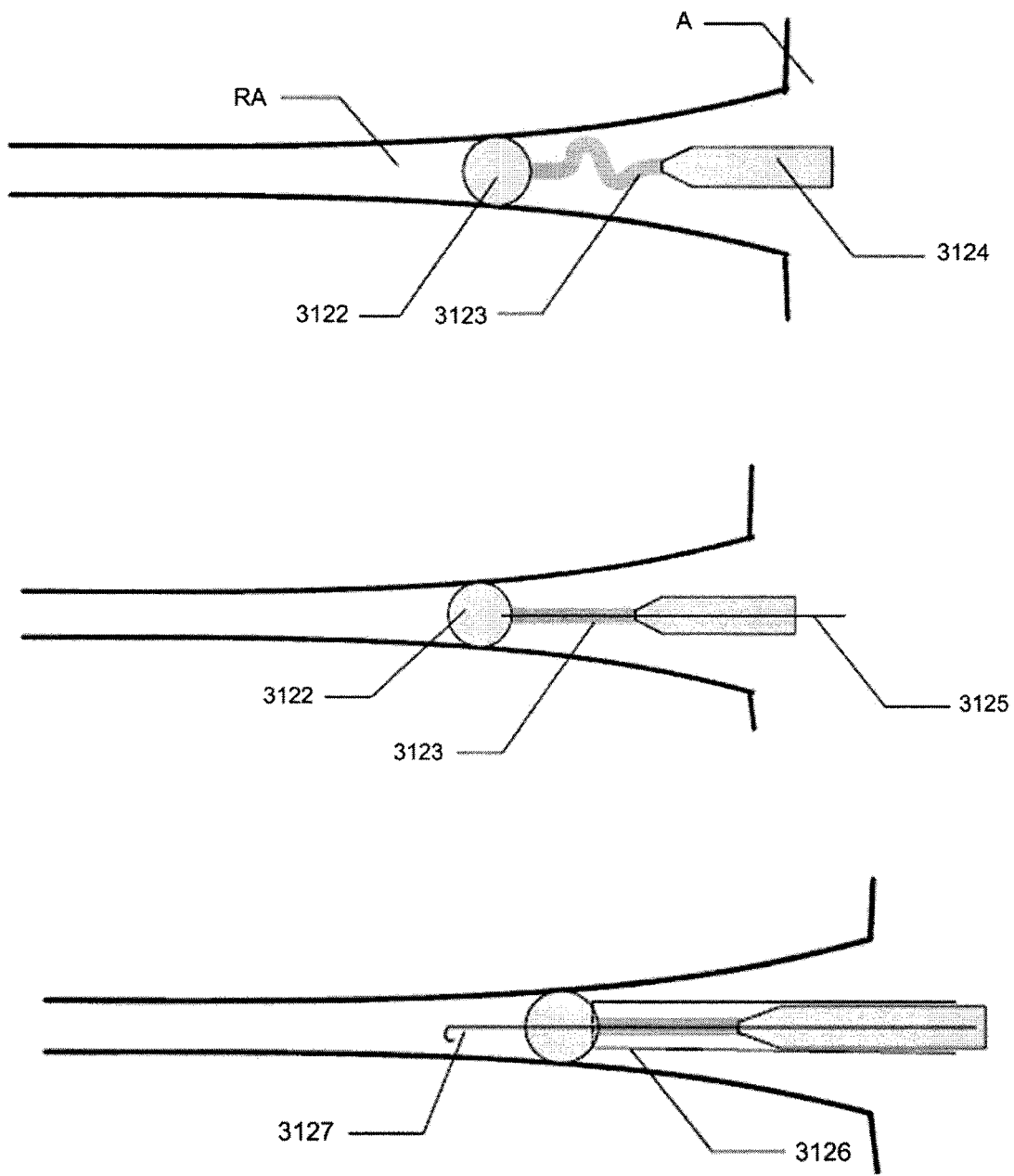

FIG. 31, for example, illustrates an embodiment of a device that incorporates a tethered ablation balloon 3122 that is pushed by a stylet 3125 or advanced over guide wire 3127 or just floated downstream into the renal artery RA from the aorta A until it is wedged there. A tether 3123 is attached to the distal segment of the more rigid catheter 3124. Alternatively, a variable durometer catheter shaft can be used that is softer towards its distal end. Because renal arteries tend to taper towards the kidney, the non-compliant balloon 3122 of a fixed size (e.g., a 5 mm diameter) can be wedged into the artery using the stylet 3125 or a thin push tube 3126.

The balloon can be temporarily inflated with non-cryogenic gas to facilitate wedging and sizing. Small puffs of refrigerant can be infused into the balloon to test the diameter. These puffs will not freeze the balloon but will keep it inflated. Radiopaque material can be added to the balloon to enable visualization. Injection of contrast agent distal and proximal to the balloon can assist in determining if the balloon is wedged into and occluding the artery.

After the desired position is achieved, the stylet 3125 can be withdrawn. Alternatively, other stiffening and guiding mechanisms (e.g., the push tube 3126) can be removed. Once such stiffening or guiding mechanisms are removed, the balloon 3122 will be flexibly tethered to the end of the catheter. The tether 3123 incorporates tubes for refrigerant and gas evacuation similar to more rigid embodiments. Pressurized liquid nitrous oxide can be delivered to the tip of the catheter from the cryoconsole through an ultra-fine, robust injection tube incorporated into the tether for added safety.

After the position of the balloon 3122 is confirmed, warm inflation gas is displaced by the cold cryo fluid vapor and the balloon 3122 is allowed to freeze to the wall. Thus, even if the patient suddenly moves, the tether 3123 is expected to prevent the balloon 3122 from dislodging.

8. Tapered Cryo Balloon

FIGS. 32A and 32B schematically illustrate an embodiment of a tapered cryoablation balloon configured in accordance with a further embodiment of the technology. More specifically, FIG. 32A shows a tapered balloon cryoapplicator 3240 (e.g., approximately 2-3 cm long) partially residing in the renal artery RA and in the aorta A. The portion 3222 of the balloon cryoapplicator 3240 that resides in the aorta A can be thermally insulated to reduce loss of cooling efficiency due to high blood flow in the aorta. The tapered balloon cryoapplicator 3240 can be mounted on a relatively stiff catheter shaft 3221 that can be braced against the opposing wall of the aorta A to facilitate "plugging" of the ostium of the renal artery RA. When the refrigerant is injected into the balloon 3240, a concentric lesion 3224 is expected to form just distal of the ostium of the renal artery RA. FIG. 32B shows a tapered balloon 3226 comprising a regular inflatable balloon configured for positioning, and fixation of the separate cryoapplicator balloon 925 that resides in the renal artery.

9. Shaped Thermal Elements

Another aspect of the present technology is directed to incorporating thermally conductive sections or features that conduct heat better than the unmodified balloon made of materials such as PET, nylon, etc. For example, thermal conductivity of the balloon wall may be enhanced by inclusion of thermally conductive material, such as metal, which may be introduced as a component of a composite elastomeric material, or as a patterned metal layer. Thermally conductive treatment regions of the balloon surface will enhance freezing in the selected pattern. Patterns can be formed by electro deposition, printing, lithography, or other means with gold, copper, silver or other highly thermally conductive material.

Strips and patterns of metal can be deposited on the surface of the balloon to achieve the desired shape of ablation. Biaxially-oriented polyethylene terephthalate (BOPET) is a polyester film made from stretched polyethylene terephthalate (PET) and is used for its high tensile strength. The most well-known BOPET trade name is Mylar™. Such balloons are readily metallized for various applications in desired patterns.

FIG. 33A, for example, schematically illustrates a balloon 3341 (e.g., a non-compliant balloon) carried by a catheter shaft 3340. The balloon 3341 includes one or more thermally conductive features, such as thermally conductive bands 3341 or patches 3343. In one embodiment, for example, the thermally conductive features include metal strips or patches on the balloon surface. In other embodiments, however, the thermally conductive features can include different materials and/or have a different arrangement. Referring to FIG. 33B, for example, the thermally conductive features can include a conductive (e.g., metal) mesh or braid 3350 carried by the balloon 3341. The conductive mesh 3350 can be formed on an external or internal surface of the balloon 3341. In other embodiments, the conductive mesh 3350 can be an integrally formed component within a wall of the balloon 3341. The mesh or braid pattern can have a variety of different configurations based, at least in part, on a desired treatment region.

The thermally conductive features 3341/3343/3350 are positioned for creation of discrete lesions in the renal artery wall. For example, if it is desired to create a 4 mm wide circumferential lesion, a balloon can be designed with a 4 mm wide thermally conductive band to apply a cold surface to exactly that portion of the vessel wall. Alternatively, four or more spaced 90° lesions that are, for example, 4 mm wide can be created while sparing the rest of the tissue in contact with the balloon surface. It will be appreciated that a variety of other different configurations and/or arrangements are possible.

In other embodiments, elements that reflect heat or insulate tissue from cold may be incorporated in the design of a balloon. For example, one effective isolator of heat is a balloon cavity filled with a gas (e.g., $CO_2$) or a space created by several adjacent or nested balloons that is filled with a gas or, alternatively, a polymer material selected for poor heat conduction. By way of example, sprayed foam polymer can be used to make patches or a thicker polymer material.

FIG. 34A, for example, illustrates an alternative way of achieving shaped and directed application of cold. Balloon 3341 can be selectively coated with strips and patterns of thermally insulating material 3445 leaving an uncoated window 3444 where the application of cold is desired. Insulating material 3445 can be applied to the external or internal surface of the balloon. Suitable patterns include a grid, stripes, overlapping rectangles, spirals, dots, arrays of separated segments, or meandering curves. In other embodiments, still further patterns or arrangements may be used. For example, referring to FIG. 34B, the balloon 3341 can include a thermally insulating mesh or braid 3450. The thermally insulating mesh or braid 3450 may be composed of a polymer material or another suitable insulating material. The thermally insulating mesh or braid 3450 can be formed on an external surface of the balloon 3341, an internal surface of the balloon 3341, or integrally formed within a wall of the balloon 3341. Although a generally helical or spiral arrangement is shown in FIG. 34B, it will appreciated that the thermally insulating mesh or braid 3450 can have a variety of different configurations or arrangements.

In still further embodiments, a structure such as an expandable mesh, weave, or basket may be positioned around a cryo-balloon as an alternative to adding an insulative coating to a cryo-balloon. The insulative structure may radially expand as the inner cryo-balloon is inflated, or it may be radially expanded in other ways. For example, a control wire may be connected to an end of the insulative structure and to an actuator in a handle such that pulling the control wire longitudinally compresses the insulative structure and radially expands it. Alternatively, an insulative structure may be pre-shaped to resiliently conform to an inner radius of a delivery sheath and radially expand when the delivery sheath is retracted. The insulative structure may be made from a material of low thermal conductivity such as a polymer. A weave pattern may be variable to allow cryoablation through segments with little or no insulative material.

Coating and material patterns can be used to selectively apply cold separately or in combination with other energy direction means. Other ways to selectively apply cold include (as previously described herein) various methods of directing a spray of refrigerant at the selected section of the internal surface of the balloon. The spray directed at the internal surface of the balloon evaporates at the contact surface and creates a "cold spot" on the inner surface of the balloon where the deeper freezing of tissue is desired. A surface of the balloon progressively more distant from the spayed spot can be used to reduce thermal losses or spare tissue.

In embodiments in which separate media are used for cooling and for balloon expansion, the cooling chamber may have a large diameter and a short length, and the balloon may form a thin shell or cuff. In such cases, the balloon may be quickly cooled while shielded from heating by blood.

10. Cryo Balloons plus Stabilization/Insulating Balloons

Figure 35A:
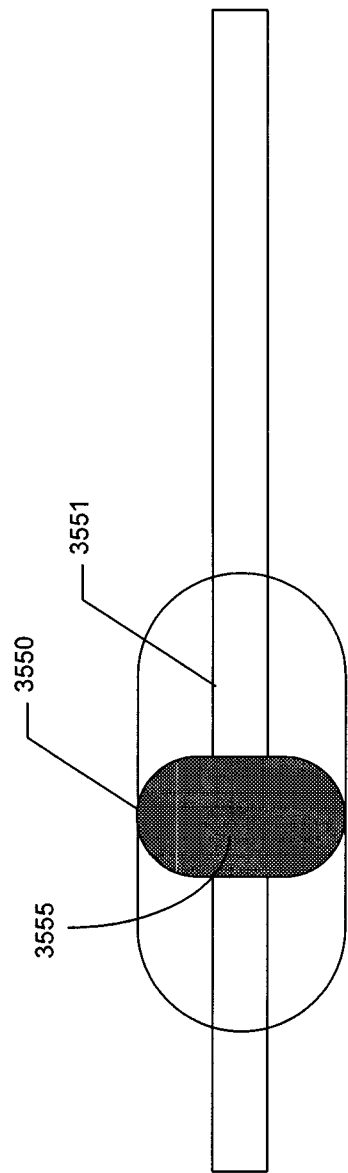
Figure 35B:
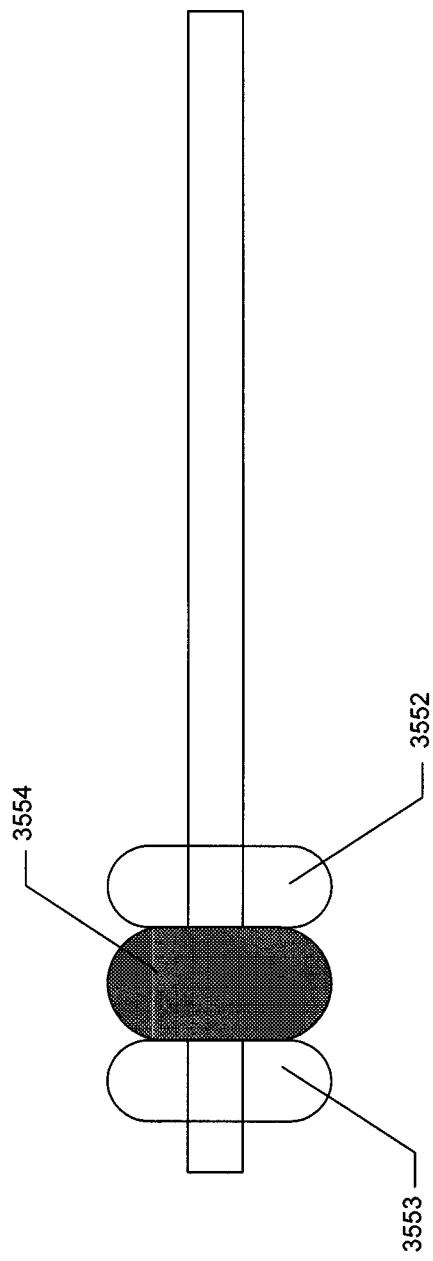

FIGS. 35A and 35B are partially schematic views of cryotherapy balloon catheters incorporating an assembly of two or more balloons. In the embodiment illustrated in FIG. 35A, for example, a cryo applicator balloon 3550 can be surrounded by an expansion balloon 3551 filled with a gas. A cooling chamber 3555 in balloon 3550 is relatively small and may be cooled with high efficiency by a phase-change refrigerant, while balloon 3551 surrounds the chamber and is inflated by a gas (e.g., $CO_2$) that acts as a heat insulator. The zone of the cryoballoon that is exposed and in contact with the vessel wall (not shown) will form a circumferential or segmented shape and lesion, while the isolation balloon will help conserve the refrigerant and speed up the procedure.

In another embodiment illustrated in FIG. 35B, two gas filled balloons 3552 and 3553 can be inflated on both sides of or inside the cryo applicator balloon 3554 to isolate a narrow region between two balloons. This arrangement is expected to reduce the area targeted for ablation and can reduce the time it takes to form an effective lesion. This feature may also facilitate positioning and fixation of the cryoballoon 3554 in the desired location. In addition, this arrangement may also help reduce the risk of trauma due to cryoadhesion by holding the cryo balloon 3554 in place.

F. Expandable Metal Tip Applicator

FIGS. 36-39 are partially schematic views of cryo-catheter configurations in accordance with further embodiments of the technology. More specifically, in this set of embodiments, an expandable metal tip 190 is provided on the distal end of the cryo-catheter 102 as the cryo-applicator region 122. The metal tip 190 may be formed using a highly thermal conductive material (e.g., stainless steel, platinum, nitinol, silver, gold) so as to allow metal to tissue contact to provide a low tissue interface temperature, thereby allowing the deepest possible ablation while using a small French catheter. Further, the metal tip 190 may include features that extend beyond the "nominal" tip diameter when entrapped by a delivery sheath 168 and may open to a larger diameter to make contact with target tissue extended beyond the delivery sheath.

Figure 36:
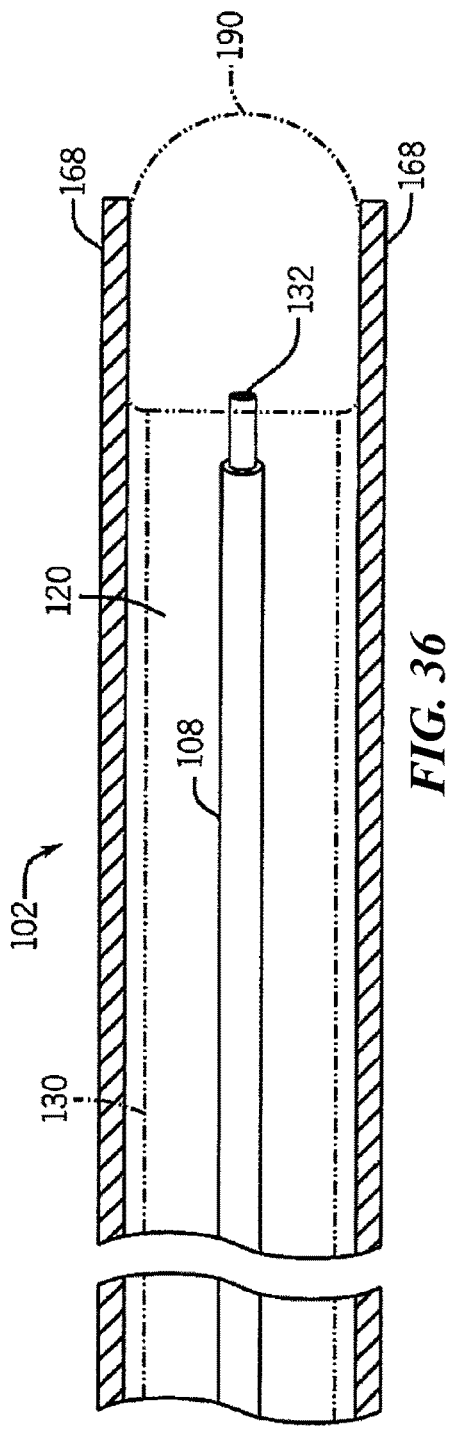
Figure 37:
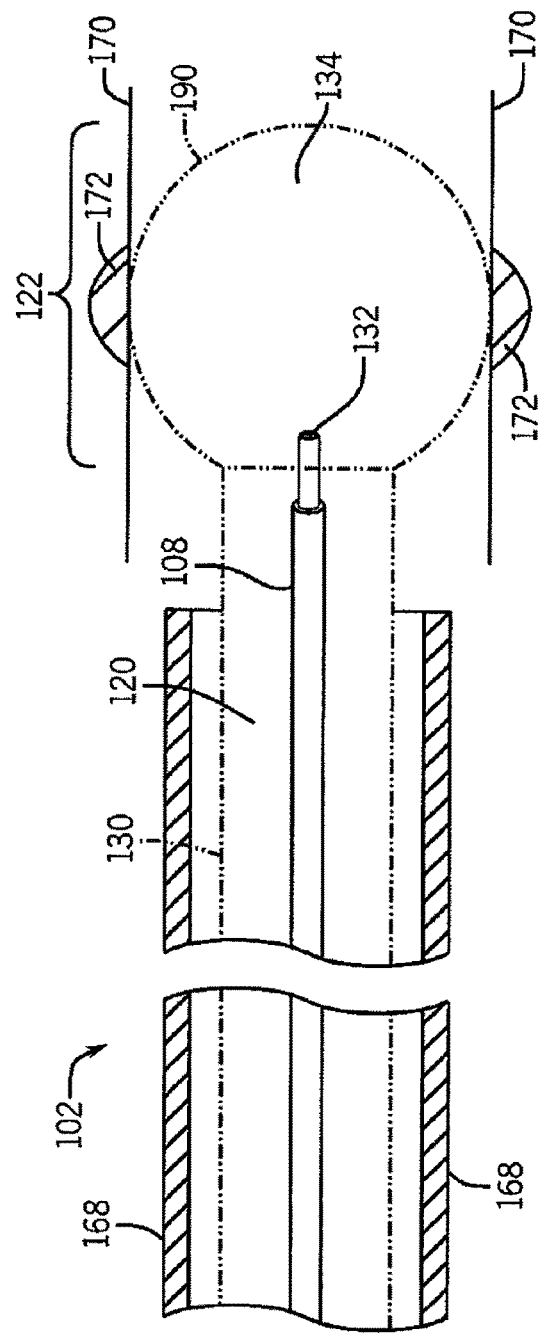

In certain of these embodiments, the metal tip 190 is capable of expanding outward, such as about 1 mm to about 3 mm outward, when not restrained by the delivery sheath 168. For example, as shown in FIGS. 36 and 37, the metal tip 190 may be a first, smaller diameter when within the delivery sheath 168 but, once extended beyond the delivery sheath 168, the metal tip 190 expands outward to a second, larger diameter sufficient to contact the walls 170 of the renal artery along the full circumference of the vessel wall or only a portion of the circumference.

Further, referring to FIGS. 38 and 39, in further embodiments one or more metallic projections 192 may be provided on the cryo-catheter 102 such that, when the applicator region 122 is contained within the delivery sheath 168, the metal projections 192 are constrained or held flush against the catheter tip. However, when the applicator region 122 is extended beyond the delivery sheath 168, the metal projections 192 are biased outward to contact the walls 170 of the renal artery to allow the formation of lesions 172. The metal projections (e.g., wings or leaflets) may extend from multiple positions on the catheter tip. In certain embodiments, the metal projections 192 may be part of a pre-formed piece that takes on a pre-formed shape when not restrained by the delivery sheath 168.

G. Variable Diameter Catheter

Cryo-ablation can sometimes present challenges not commonly seen in other ablation techniques. For example, cryo-ablation introduces challenges related to maintaining the desired temperature and pressure not only of the refrigerant 106 that is being supplied to the target site, but also of the returning evaporated refrigerant 118. In general, the larger the catheter French size the easier it becomes to achieve high refrigeration and low back pressure but the catheter also may become stiffer and thus flexibility necessary to navigate the bend from the aorta to a renal artery and positioning of the applicator is impacted. Similarly, small French catheters can be positioned more easily but may not be capable of delivering adequate refrigeration. A vacuum pump can help to maintain a fixed return pressure so refrigeration power is improved. However, this would be at the cost of increased complexity of the cryo-system 10 with an added vacuum pump 126, pressure monitors and regulators and the outer wall of the return lumen 120 would have to be rigid enough to withstand the vacuum without collapsing, adding stiffness to the cryo-catheter 102.

Figure 40:
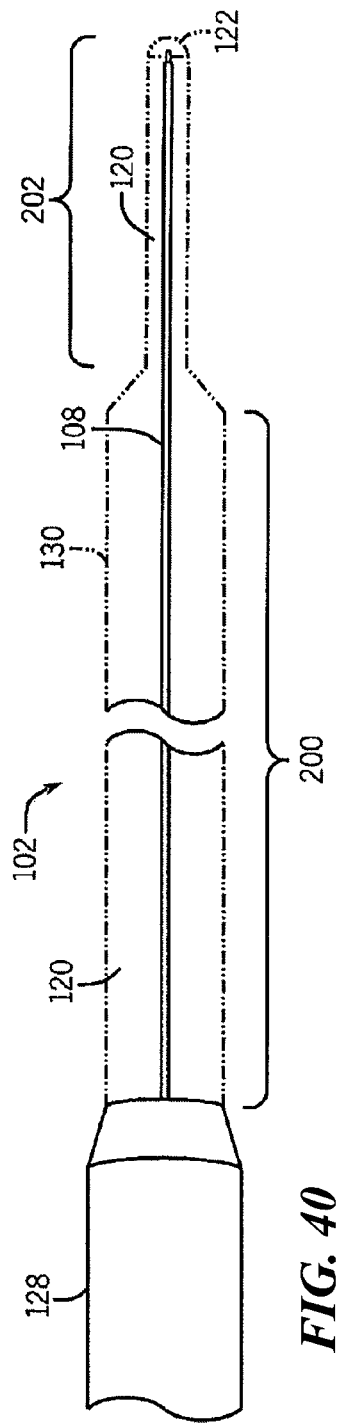
FIG. 40 is a partially schematic view of one embodiment of a cryo-catheter having a multi-diameter shaft configured in accordance with an aspect of the present disclosure.

FIG. 40 is a partially schematic view of a cryo-catheter configuration in accordance with another embodiment of the technology. In this embodiment, the device includes a cryo-catheter body having at least two sections with different diameters. The difference in the diameters of the two different sections is reflected in the volume of the return lumen 120 defined by the walls of the cryo-catheter 102. In one embodiment, for example, the cryo-catheter 102 consists of a delivery section 200 (that may be 90% or more of the length of the catheter shaft 130 in one implementation) and a deflectable section 202 (that may be 10% or less of the length of the catheter shaft 130 in one implementation). In one implementation, the delivery section 200 (and the return lumen 120 defined therein) has a greater diameter (e.g., 6 to 8 French) than the deflectable section 202 and is of sufficient length to extend from outside the body via a femoral access along the aorta approximately to the renal artery ostium, or just before the bend in a renal guide catheter. In the depicted implementation, the deflectable section 202 (and the return lumen 120 defined therein) has a smaller diameter (e.g., 3 to 5 French) relative to the delivery section 200 and is therefore more flexible than the delivery section 200 and can navigate the bend from the aorta to the renal artery more easily.

Among other benefits, the greater diameter of the delivery section 200 relative to the deflectable section 202 reduces the backpressure within the return lumen 120 of the cryo-catheter 102 for a given flow of refrigerant 106 compared to a catheter with a fixed smaller diameter the entire length. Reduced backpressure with a given refrigerant flow rate can decrease the boiling temperature of the refrigerant thereby increasing the penetration depth of a cryogenic lesion. Furthermore, a refrigerant could flow at a greater rate with less of an impact on backpressure and thereby refrigeration power at the applicator region 122 can be increased. In particular, resistance of flow through a tube is a function to the fourth power to the diameter. An increased diameter of the delivery section for at least a portion of the length of the cryo-catheter 102 can thereby reduce resistance to flow of the evaporated refrigerant 188 returning from the applicator region 122.

Furthermore, the returning evaporated refrigerant 118 at the distal deflectable section 202 of the cryo-catheter 102 is at a lower temperature than the gas that is leaving the cryo-catheter 102 at the proximal end of the delivery section 200 (i.e., at or near the handle 128) because as it travels the length of the cryo-catheter 102 through the return lumen 120 there is some heat transfer with both the blood in the body surrounding the cryo-catheter 102 and even the liquid refrigerant 106 at about room temperature in the supply lumen 108. Colder gas has a higher density than the warmer gas. Therefore, in a return lumen of equal diameter, as the gas warms the density decreases and therefore the pressure in the return lumen 120 increases, including the pressure in the cryo-applicator region 122, which would increase the boiling temperature of the refrigerant 106. Thus, it is expected that the cryo-applicator region 122 would not reach as low a temperature and the penetrating depth of the cryogenic temperature would decrease. As disclosed herein, an increased diameter of the delivery section (and the encompassed return lumen 120) reduces the back pressure caused by warming gas. By increasing the diameter of the exhaust lumen 120 in the delivery section 200, the volume through which the warming gas expands is increased and the effect on the pressure in the cryo-applicator 122 is reduced. Further, the improvement in refrigeration power enabled by the increased diameter of the delivery section 200 may have advantages such as eliminating the need of vacuum evacuation or pre-cooling the refrigerant 106, or it may allow various designs with other losses of refrigeration power to be feasible.

For simplicity, a cryo-catheter 102 having only two sections (i.e., a delivery section 200 and a deflectable section 202) has been depicted and described. As will be appreciated, however, more than two differently dimensioned sections may be employed (e.g., three, four, five, and so forth) where the sections have respectively increasing diameter the closer they are to the handle 128 of the cryo-catheter 102. Further, in certain implementations one or more of the sections (or the entire length of the cryo-catheter 102) may be continuously tapered such that the diameter continuously decreases as one approaches the tip of the cryo-catheter 102.

Further, it should be understood that other sections than the deflectable section 202 (e.g., the delivery section 200) may retain some degree of flexibility and may be deflectable. For example all or part of the cryo-catheter 102 may deflect in response to user control. Controllable deflection of the deflectable section 202 or of other sections can be accomplished, for example, with a control cable and flexibly biased member. Deflection can also be accomplished by providing a pre-formed bend at the distal end region of the elongated shaft.

H. In-Line Pre-Cooling Catheter

Figure 41:
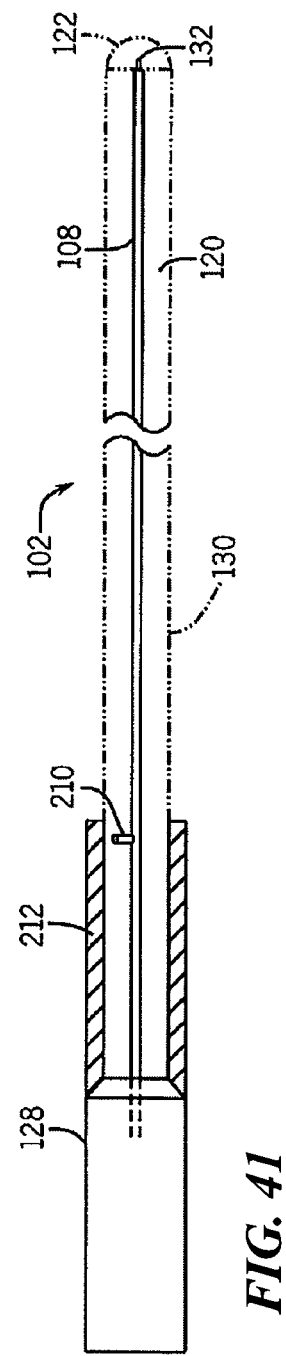
FIG. 41 is a partially schematic view of an embodiment of a cryo-catheter having in-line pre-cooling configured in accordance with an aspect of the present disclosure.

FIG. 41 is a partially schematic view of a cryo-catheter configuration in accordance with another embodiment of the technology. In this embodiment, a method for pre-cooling the refrigerant 106 in the cryo-catheter 102 (as opposed to in the cryo-console 100 or other external, powered device) is provided. As will be appreciated, one technique to increase refrigeration power is to pre-cool the refrigerant 106 prior to using the refrigerant 106 in a procedure, i.e., just before the refrigerant reaches an expansion chamber. Such pre-cooling can possibly allow a smaller diameter cryo-catheter 102 to be used which may allow use of a thinner, more flexible catheter and may have other clinical advantages as well. However, conventional methods of pre-cooling, such as the use heat exchangers in a console, can add complexity and cost to a cryo-system. Pre-cooling may mitigate reduction of refrigerant power caused by other design configurations, such as catheter dimensions or the use of solenoid valves that may warm the refrigerant. Pre-cooling may also mitigate reduction of refrigerant power caused by a patient's body temperature warming the refrigerant.

As disclosed herein, a presently contemplated approach is to utilize in-line pre-cooling in the cryo-catheter itself. For example, in one implementation, at least one pre-cooling orifice 210 is provided in the cryo-catheter 102 proximal to the orifice(s) 132 present in the applicator region 122. In one such implementation, the opening of the pre-cooling orifice 210 is smaller (e.g., about 0.254 mm to about 0.0508 mm) than the opening associated with the orifice 132 in the applicator region 122. The pre-cooling orifice 210 allows a small amount of refrigerant 106 to exit the supply tube 108, thereby cooling the refrigerant 106 flowing in the supply tube 108 proximal to the pre-cooling orifice so that the remaining refrigerant 106 has greater refrigeration power when it reaches the applicator region 122.

The section of the cryo-catheter 102 that is proximal to the pre-cooling orifice 210 may be cooled substantially by the refrigerant 106 exiting the supply tube 108 through the pre-cooling orifice 210. Therefore, in one implementation, the pre-cooling orifice 210 is located in a portion of the cryo-catheter 102 that remains outside the body of the patient, such as in the handle 128 or a portion of the catheter shaft 130 proximate to the handle 128 or otherwise between the handle 128 and the body of the patient. In this way the cooling associated with the pre-cooling orifice 210 does not injure non-target tissue and the patient's blood flow does not reduce pre-cooling power. Further in certain embodiments, a layer of insulation 212 may be added to a portion of the cryo-catheter 102 to mitigate the cooling of the cryo-catheter 102 caused by the pre-cooling orifice 210. Addition of the layer of insulation 212 may also result in an increase in diameter of that portion of the cryo-catheter 102 while still maintaining smaller diameter femoral stick.

By way of example, pre-cooling using a pre-cooling orifice 210 may create an area of about −80° C. around the supply lumen 108, thereby providing approximately 3 W of refrigeration power and reducing the temperature of the refrigerant 106 in the supply lumen 108 from about 23° C. (i.e., room temperature) to about 5° C. By the time the liquid refrigerant 106 reaches the cryo-applicator region 122, the temperature of the refrigerant 106 would be lower than if it were not pre-cooled and therefore it would have a higher heat capacity and greater refrigeration power.

Figure 42:
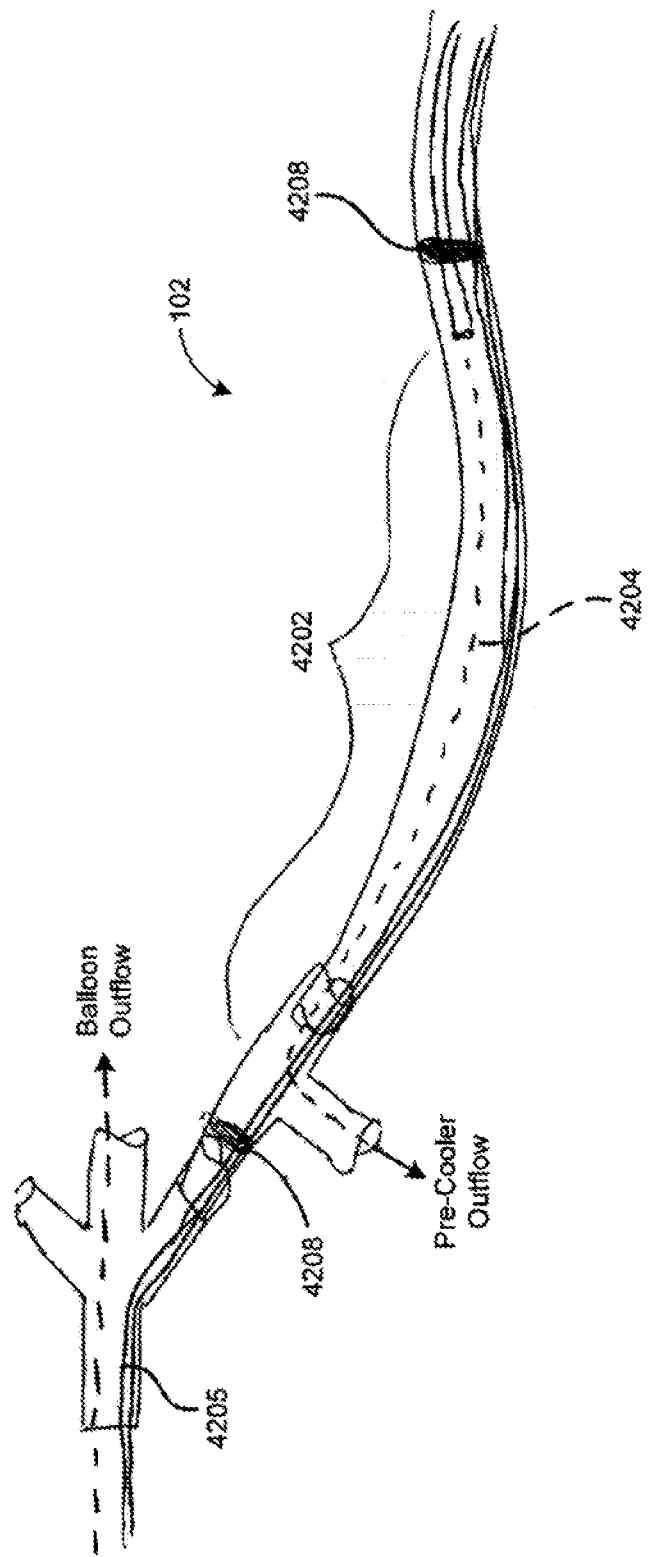
FIG. 42 is a partially schematic view of another embodiment of a cryo-catheter having in-line pre-cooling configured in accordance with an aspect of the present disclosure.

FIG. 42 is a partially schematic view of an in-line pre-cooling cryo-catheter 102 configured in accordance with another embodiment of the technology. At the proximal end of the cryo-catheter 102, there is a pre-cooling section 4202. A supply tube 4205 connects to a supply of refrigerant and runs through the pre-cooling section 4202 and then through the catheter shaft to the cryo-applicator. A separate pre-cooling supply tube 4204 also connects to a supply of refrigerant and releases refrigerant into a proximal end of the pre-cooling section 4202. The pre-cooling supply tube 4204 may contain a restriction orifice or capillary tube at its distal end to maintain a pressure difference and control flow. Upon exiting the pre-cooling supply tube 4204 through a restriction orifice, refrigerant expands under lower pressure (e.g., about 1 Atm), absorbing a large amount of heat. The gas flows through the length of the pre-cooling section 4202 and is released at a distal end of the pre-cooling section 4202 to atmosphere or a collection chamber. Flow of gas is contained in the pre-cooing section 4202 by occluding proximal and distal ends of the pre-cooling section with occlusion elements or blocks 4208 (e.g., UV glue). Heat is removed by conduction from liquid refrigerant flowing through the supply tube 4204 that runs through the pre-cooling section. The pre-cooling section 4202 may be less than about 12" long (e.g., about 8"). Optionally, the pre-cooling section 4202 may be contained in a handle, coiled, and/or insulated. Optionally, flow through the pre-cooled section may be controlled by a valve at the inflow or outflow. In still other embodiments, the in-line pre-cooling cryo-catheter 102 of FIG. 42 may have other features and/or a different arrangement.

I. Catheter with a Cooling Delivery Sheath/Guide Catheter

As will be appreciated, as a refrigerant 106 travels down the supply lumen 108 when the cryo-catheter 102 is deployed, the refrigerant 106 may increase in temperature due to the warmth from the body of the patient. For example, the refrigerant 106 may be supplied at about room temperature (about 23° C.), and as it passes through the body, which is about 37° C., it may increase in temperature as it approaches the cryo-applicator 122. An increase in temperature of the supply refrigerant 106 reduces its refrigeration power. Furthermore, the evaporated refrigerant 118 may be relatively cold at the cryo-applicator 122, such between −80° C. and −90° C., depending on the pressure. However, as the evaporated refrigerant 118 passes through the return lumen 120, the evaporated refrigerant 118 warms as heat is transferred from the body. The warmed gas 118 may cause an increase in back pressure, which also may increase the boiling point and thereby increase the temperature achieved at the cryo-applicator 122.

Figure 43:
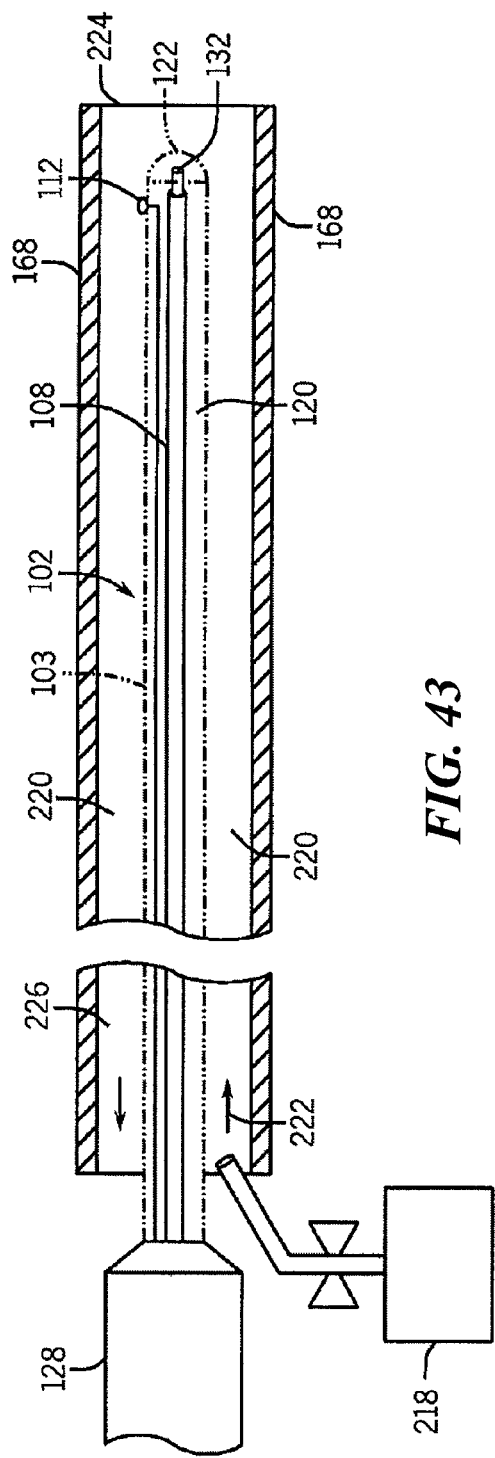
FIG. 43 is a partially schematic view of an embodiment of a cryo-catheter cooled within a delivery sheath in accordance with an aspect of the present disclosure.

FIG. 43 is a partially schematic view of a cryo-catheter configuration in accordance with another embodiment of the technology. One technique that may be employed to prevent heating of the refrigerant 106 and the evaporated refrigerant 118 in the cryo-catheter 102 is to provide cooling of the cryo-catheter 102 itself while deployed in the body of the patient. For example, one implementation cools the shaft 130 of the cryo-catheter 102 by circulating or injecting a coolant 222 in a lumen 220 defined by the exterior surface of the cryo-catheter 102 and the inner surface of a delivery sheath 168 or guide catheter. The coolant 222 reduces the warming effect of the blood on the cryo-catheter 102.

In one embodiment, a cooling fluid 222 (e.g., saline) is injected into the space between the delivery sheath and the cryo-catheter 102 such that the cooling fluid 222 passes over the cryo-catheter 102. Such as from a cooling fluid supply 218 in fluid communication with the lumen defined between the cryo-catheter 102 and the delivery sheath 168. The cooling fluid 222 can be about room temperature (i.e., about 23° C.) or cooled below room temperature. In one embodiment, a biologically harmless cooling fluid 222 may be employed and may be released into the vasculature of the patient at the distal end of the delivery sheath or guide catheter.

In another embodiment, a delivery sheath 168 or guide catheter can have a flow limiter or seal 224 at the distal end that restricts flow of the cooling fluid 222 out of the delivery sheath 168. Additionally, a second lumen 226 can be provided in the wall of the delivery sheath 168 to allow cooled fluid 222 to circulate proximal to distal end of the cryo-catheter 102 and back again. Alternatively, the flow limiter 224, if present, can be a pressure regulated valve that seals around the cryo-catheter 102 to prevent the flow of blood back into the delivery sheath 168 due to blood pressure. In such an embodiment, with infusion of the cooling fluid 122, the flow limiter 224 would allow outward flow above a given pressure such that cooling fluid 222 can flow from the delivery sheath 168 in to the patient.

Additionally, one or more sensors 112 (e.g., a thermocouple) may be provided on the cryo-catheter 102, such as on shaft 130 and/or on the delivery sheath shaft to monitor the temperature inside the delivery sheath 168 and/or on the surface of the cryo-catheter 102. The measured temperature signal may be used as feedback in a software control algorithm to control the flow rate of infused cooling fluid 122, such as from cooling fluid supply 218, to maintain a target temperature within the delivery sheath. In one embodiment, the algorithm can also be used to turn on flow and reach target temperature before initiating delivery of the refrigerant 106 to the applicator region, turn off flow following termination of refrigerant delivery (i.e., at the end of the procedure), or provide feedback to a physician to manually alter flow rate to stay within desired temperature parameters.

IV. Mathematical Modeling of Example Treatment Parameters

A. Introduction

In general, it is desirable to freeze tissue as quickly as possible and to maintain the desired temperature at the catheter balloon/tissue interface. In practice, the procedure should take several minutes or less to be practical and acceptable to clinicians and patients. The thermal modeling examples discussed below provide additional insight into the desired cooling characteristics of a system for cryo-modulation of renal nerves.

A numerical study was performed to determine the transient tissue temperature distributions adjacent to a section of 6 mm diameter blood vessel, such as a renal artery, that is abruptly cooled from 37° C. to −80° C. Three separate simulations were conducted—in the first simulation the cooled section of vessel was semi infinitely long; in the second simulation the cooled length of vessel was 2 cm long; in the third simulation, the cooled length of vessel was 5 mm long and cooling was applied along only ¼ of the circumference of the cooled section. The initial tissue temperature was 37° C. for all analyses and all simulations were carried out for 120 second treatment durations. It will be appreciated that the following discussion is directed to specific examples associated with this study, and that further examples or studies may have different results.

B. Analysis Method

The governing differential equation for energy transfer in many biological systems can be shown to be the following modified Penne's bioheat equation:

$$\rho c_p \frac{\partial T}{\partial t} = \nabla [k \nabla T] + Q_m - \rho_b c_{pb} \alpha \omega (T - T_{amb}) \qquad (10)$$

in which $\rho$ is density (kg/m$^3$), $c_p$ is heat capacity (J/kg-K), T is the local temperature (° C.), k is thermal conductivity (W/K-m), $Q_m$ is the metabolic heat source term (W/m$^3$) which, for the reason described below, was assumed insignificant for the present study, $\rho_b$ is blood density (kg/m$^3$), $c_{pb}$ is the heat capacity of blood (J/kg-K), $\alpha$ is a tissue state coefficient that lies between 0 and 1 depending on the level of tissue damage, $\omega$ is the blood perfusion coefficient (1/sec), and $T_{amb}$ is the ambient body temperature as carried by the blood through the body (° C.). The expression $\rho_b c_{pb} \alpha \omega (T - T_{amb})$ is referred to as the blood perfusion term.

It has been observed that with high cooling rates and for tissue regions close to the low temperature source, blood perfusion and metabolic heating terms do not have a significant influence on calculated temperatures for the regions and times of interest. This happens because at short times and close to the low temperature source, heat transfer by conduction overwhelms the calculated heat transfer by blood perfusion or metabolic heating. The finite element analyses were made using COMSOL (commercially available from Comsol, Inc., Burlington, Mass.).

C. Calculated Temperature Distributions

For all simulations, the temperature of the cold surface was smoothly ramped from 37° C. to −80° C. over a one second duration.

Simulation 1: Semi Infinitely Long Cold Source

Figure 44A:
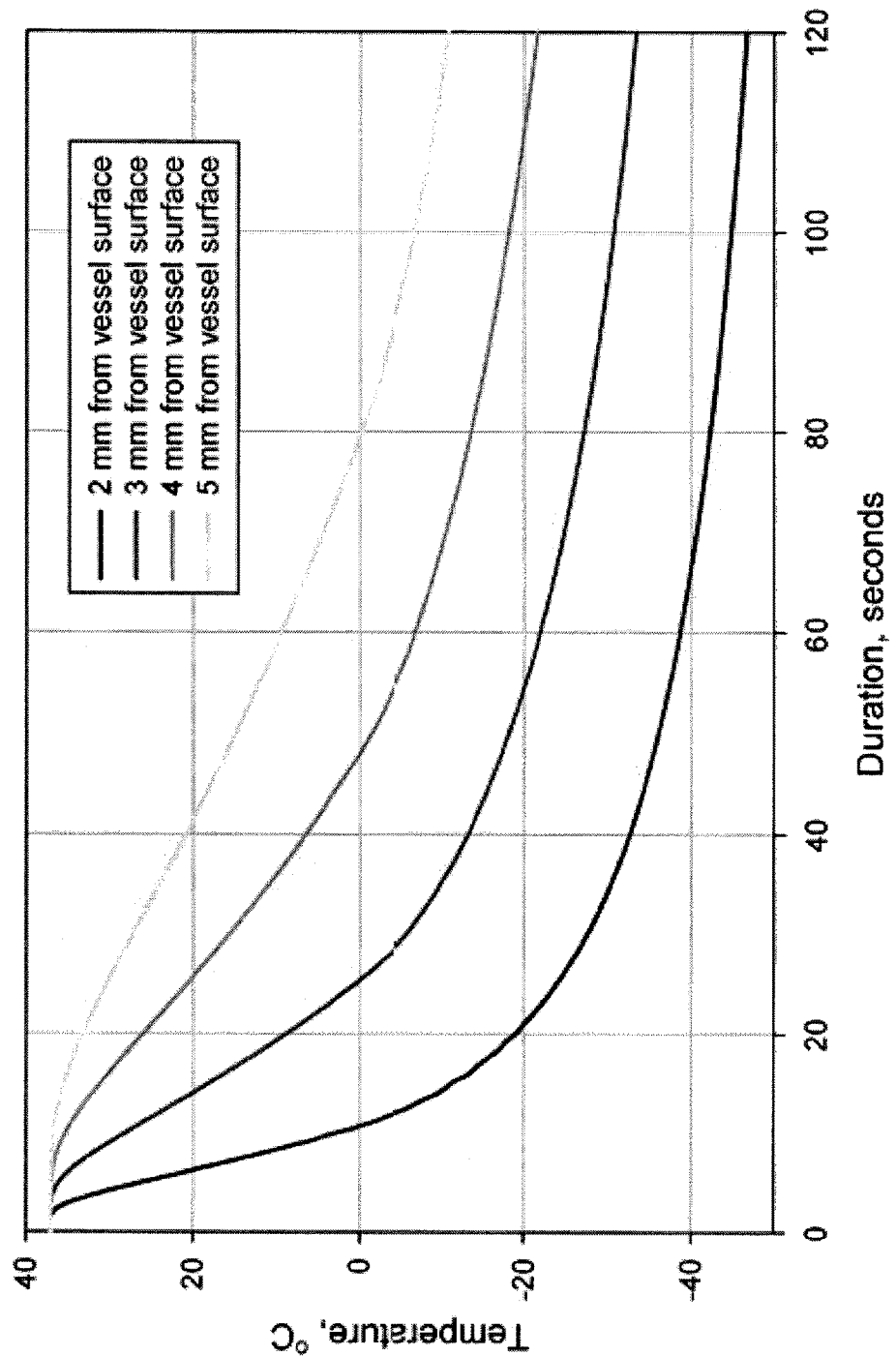
FIGS. 44A-44D graphically illustrate the calculated temperature versus time profiles at distances of 2, 3, 4, and 5 mm from the vessel surface in accordance with various examples of the present technology.

FIG. 44A shows the calculated temperature versus time profiles at distances of 2, 3, 4, and 5 mm from the vessel surface. Since the cooled section of vessel was semi infinitely long, the computed temperatures are solely a function of radius and time.

Simulation 2: 2 cm Long Cold Source

Figure 44B:
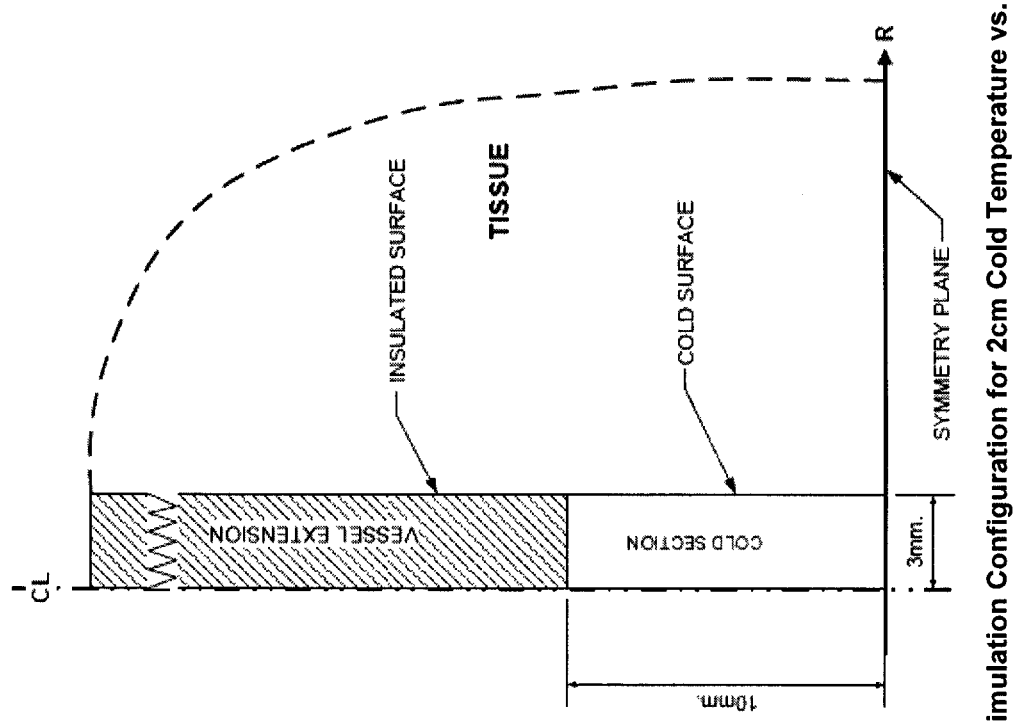

FIG. 44B shows the configuration for Simulation 2. The 2 cm long cold section can be numerically simulated with a 1 cm long cold section because of symmetry. The surface of the un-cooled vessel extension is assumed to be insulated. The computed temperatures for this configuration are a function of both radius from the vessel centerline and the position along the vessel centerline, as well as temperature.

Figure 44C:
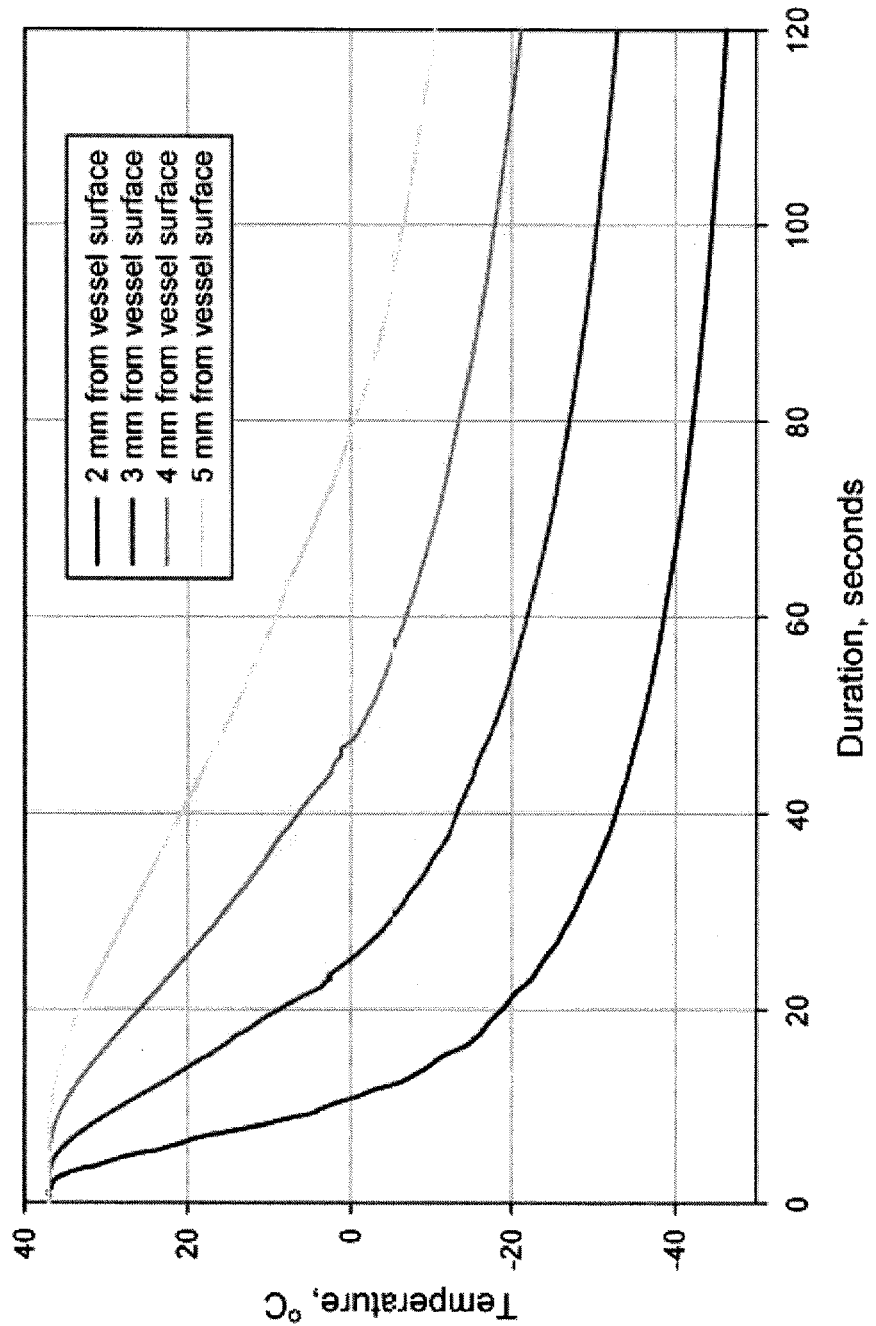
Figure 44D:
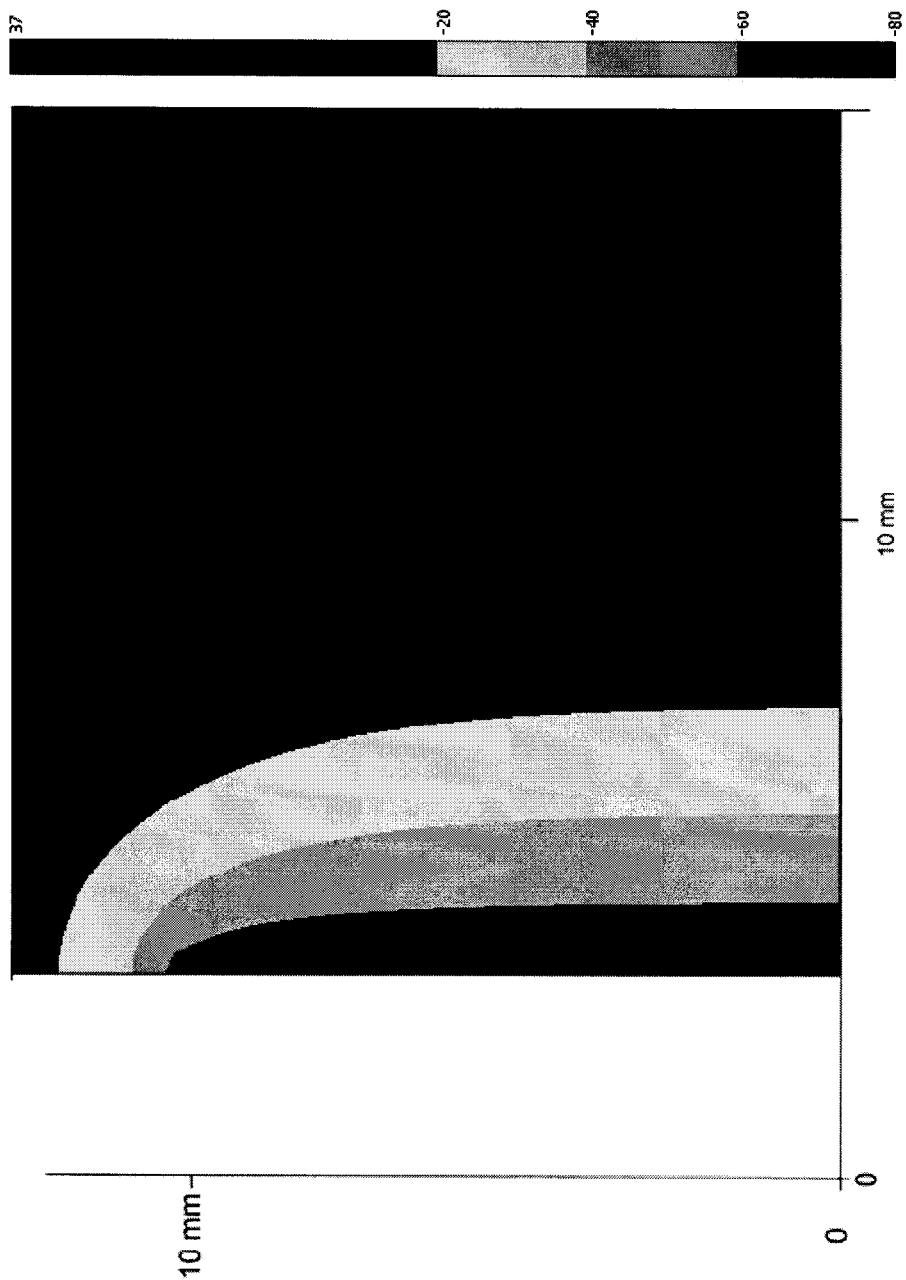

FIG. 44C shows the calculated temperature versus time profiles along the symmetry plane at distances of 2, 3, 4, and 5 mm from the vessel surface. The plot of FIG. 44C is nearly identical to that of FIG. 44A and the numerical data show that the computed temperatures are less than 1° C. different for the two cases. Without being bound by theory, it is believed that this indicates that the "end effects" of a 2 cm long cold section do not affect the midpoint tissue temperatures. This is further demonstrated from an examination of the temperature contours at 120 seconds shown in FIG. 44D.

Simulation 3: 5 mm Long Cold Source with Cooling is Applied Along ¼ of the Circumference of the Cooled Section.

Figure 45:
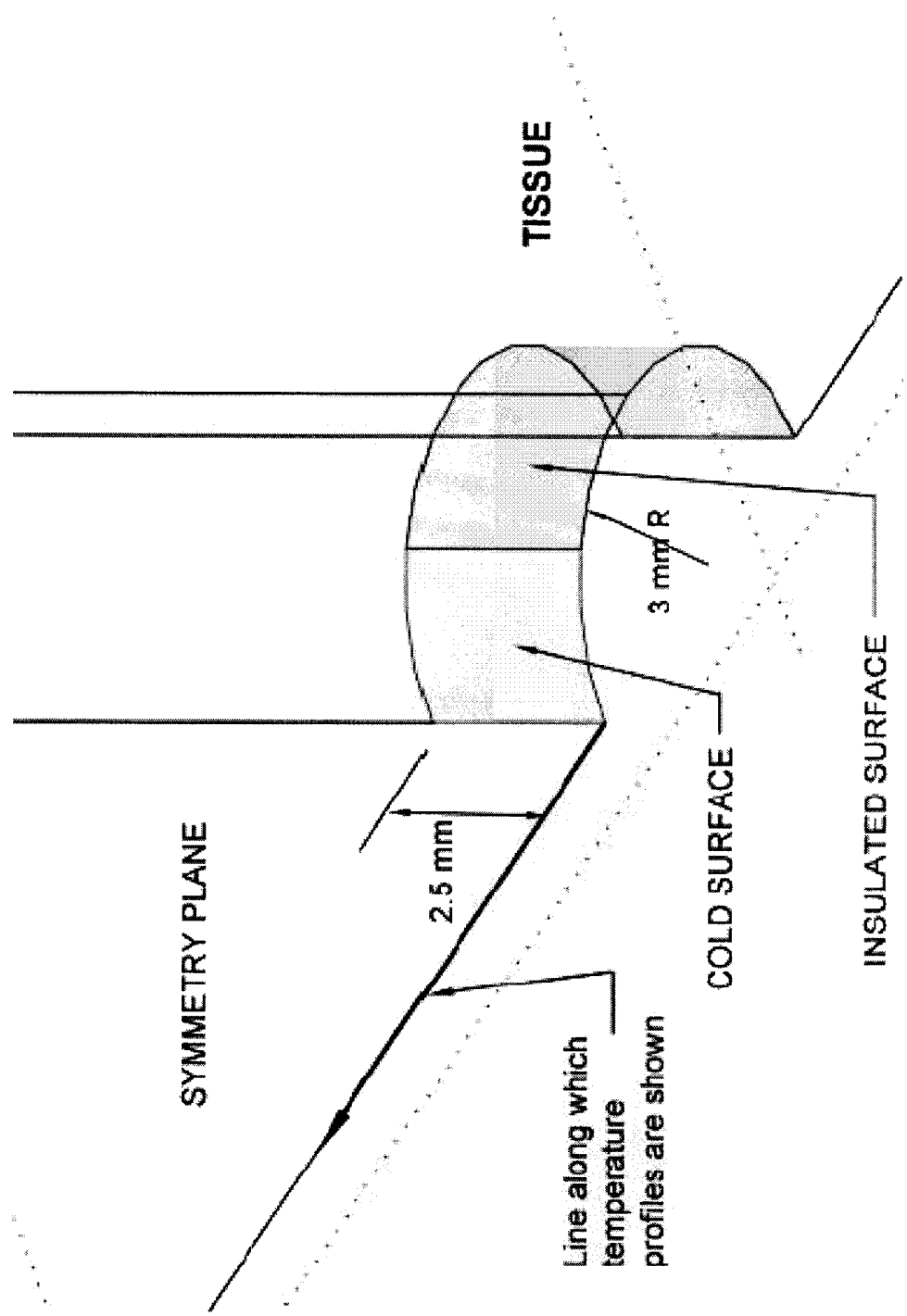
FIG. 45 illustrates the configuration for this simulation as viewed through the symmetry plane along the vessel axis.
Figure 46:
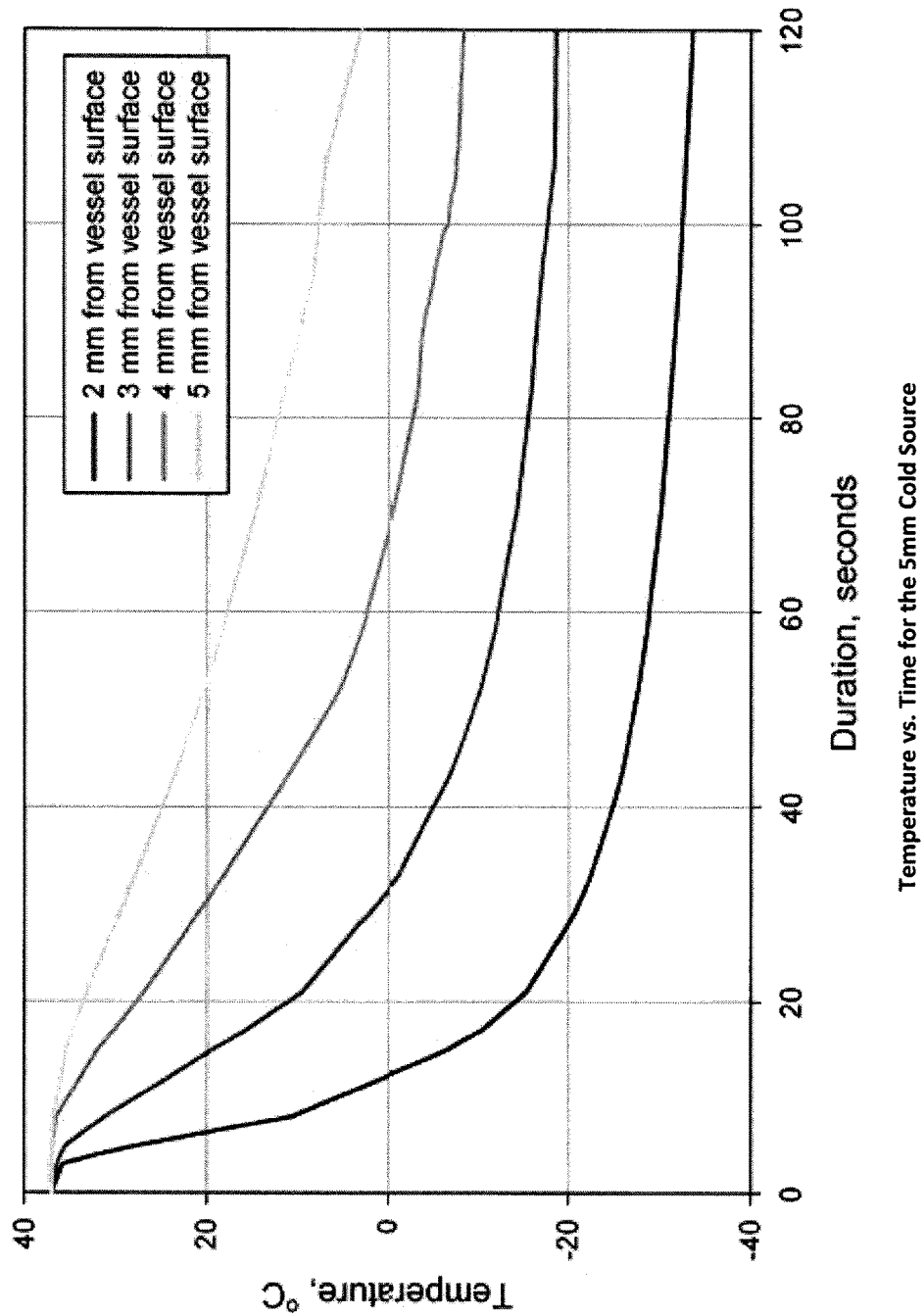
FIG. 46 graphically illustrates the profiles of temperature versus time along the two symmetry planes at distances of 2, 3, 4, and 5 mm from the vessel surface.

In this case there are two symmetry planes. One is along the axis of the vessel, and the other, as with the previous simulation, is perpendicular to the vessel axis, midpoint along the length of the cooled section. FIG. 45, for example, shows the configuration for this simulation as viewed through the symmetry plane along the vessel axis. This Figure also shows the line along which the temperatures of FIG. 46 are shown. This line is the intersection of the two symmetry planes.

FIG. 46 shows the profiles of temperature versus time along the two symmetry planes at distances of 2, 3, 4, and 5 mm from the vessel surface. As anticipated, the smaller area of the cold surface reduces the volume of chilled tissue in comparison to the other cases.

V. Examples of Treatment Parameters

Figure 47:
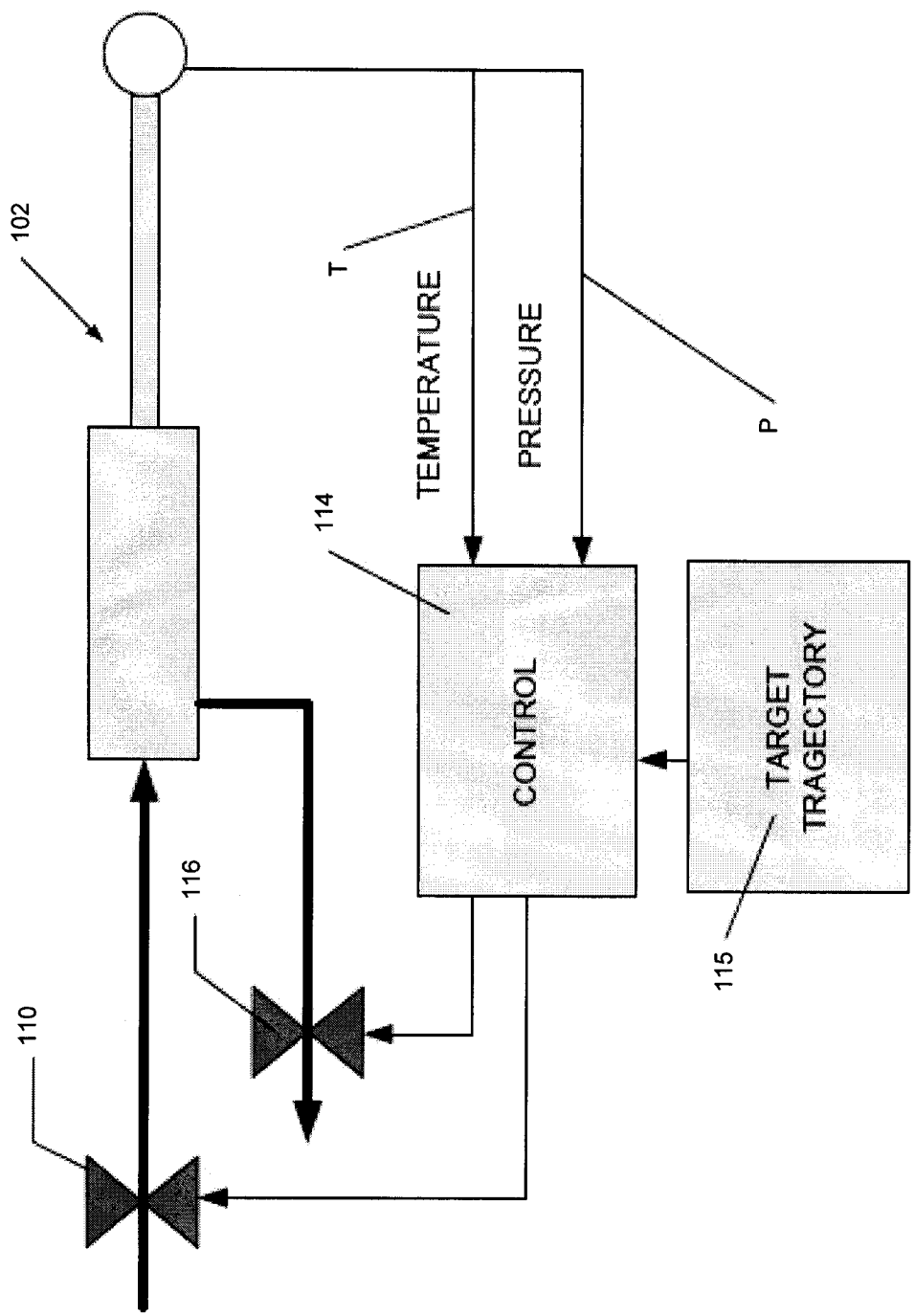
FIG. 47 is a schematic diagram of one more processors or dedicated circuitry and embedded software to control a cryomodulation procedure in accordance with an aspect of the present disclosure.

FIG. 47 provides a conceptual illustration of one more processors 114 or dedicated circuitry (See FIG. 5A) and embedded software to control the cryomodulation procedure. The procedure objectives mentioned above make it desirable to have an automatic control loop or several feedback loops as a part of the embedded logic in the cryoconsole. These control loops can involve known feedback control algorithms such as PID controller. They can be nested on several levels or combine several inputs to control one output. In some examples, the goal of control is to maintain the desired target trajectory (block 115) of tissue cooling.

In many instances, a large majority of target nerves will be within 3 mm of an inner surface of a renal artery. Under these circumstances it may be desirable to cool tissue to below −20° C. at a depth of 3 mm in order to injure a large majority of the target nerves. For example, according to the trajectory of tissue cooling of the 2 cm long cold source of simulation 2 (see FIG. 44C) tissue to a depth of 3 mm can be cooled to below −20° C. in under 60 seconds (e.g., about 56 seconds). Therefore, a device with a 2 cm long applicator can apply a contact temperature of −80° C. for about 60 seconds and tissue to a depth of 3 mm could be expected to cool to below −20° C. It may be further desirable to maintain tissue up to a depth of 3 mm at below −20° C. for at least 20 seconds in order to afflict greater injury to a large majority of the target nerves. A device with a 2 cm long applicator can apply a contact temperature of −80° C. for about 80 seconds and tissue to a depth of 3 mm could be expected to remain below −20° C. for at least 20 seconds.

In the event the applicator achieves a contact temperature of about −60° C., it will take generally longer to achieve a temperature of −20° C. in the target tissue at a depth of about 3 mm compared to an applicator at −80° C. Hence, it may take less than or equal to 120 seconds with a −60° C. applicator to achieve −20° C. in the target tissue. If it desirable to have at least 20 seconds of cooling at −20° C. at 3 mm depth, then it may be useful to maintain cooling at the renal artery wall for about 140 seconds to about 150 seconds.

In other instances, it may be adequate to ablate a smaller majority of target nerves in order to achieve the desired therapeutic benefit. In such cases the smaller majority of target nerves are within 2 mm of an inner surface of a renal artery. Hence, it may be desirable to cool tissue to a depth of 2 mm to below −20° C. in order to injure the smaller majority of target nerves. For example, according to the trajectory of tissue cooling of the 2 cm long cold source of simulation 2 (see FIG. 44C) tissue to a depth of 2 mm can be cooled to below −20° C. in under 25 seconds (e.g., about 22 seconds). Therefore, a device with a 2 cm long applicator can apply a contact temperature of −80° C. for about 25 seconds and tissue to a depth of 2 mm could be expected to cool to below −20° C. It may be further desirable to maintain tissue up to a depth of 2 mm at below −20° C. for predetermined duration (e.g., at least 20 seconds) in order to afflict greater injury to the target nerves. A device with a 2 cm long applicator can apply a contact temperature of −80° C. for about 25 seconds plus the predetermined duration (e.g., a total time of 45 seconds) and tissue to a depth of 2 mm could be expected to remain below −20° C. for at least the predetermined duration.

Likewise, according to the trajectory of tissue cooling of the 5 mm long cold source of simulation 3 (see FIG. 46) tissue to a depth of 2 mm can be cooled to below −20° C. in under about 30 seconds (e.g., about 29 seconds). Therefore, this device can apply a contact temperature of −80° C. for about 30 seconds and tissue to a depth of 2 mm could be expected to cool to below −20° C.

In one specific example, treatments were conducted at 30, 60, and 90 second durations. All of there treatments were conducted using both a single cycle protocol and a double cycle protocol (i.e., meaning a treatment followed by approximately 30-60 seconds of thawing with blood flow, then a second treatment in the exact same location in the artery). In these specific examples, it was discovered that single and double cycle 30-second treatments created suitable lesions as well as a positive reduction in norepinephrine. In some instances, however, such 30-second treatments may not reliably create effective lesions. Turning to the 60-second treatments, it was discovered that single cycle 60-second treatments provided results similar to the double cycle 30-second treatments. Further, double cycle 60-second treatments provided consistently effective lesions and a significant reduction in norepinephrine. Finally, single cycle 90-second treatments provided results comparable to the double cycle 60-second treatments, while the double cycle 90-second treatments created effective, relatively large lesions and also resulted in a significant reduction in norepinephrine. In these specific examples, the internal balloon temperatures were between approximately −70° C. and −80° C. It is believed that the external balloon temperature (i.e., vessel wall temperature) was approximately 15-20° C. warmer than the internal balloon temperature. It will be appreciated that the foregoing discussion is based on data from a particular set of example treatments and is not intended to be limiting. Further, any of the foregoing treatment parameters, protocols, results, etc. may be different in other examples.

Control considerations such as the use of real time measurements of balloon pressure P and optionally temperature T are useful in developing and designing the embedded logic algorithms for a cryosystem. Temperature in the balloon can be modeled using known pressure in the balloon and mass flow of the refrigerant. These measurements are acquired by the embedded logic, digitized and compared to target values. Flow of the refrigerant and the outflow of vapor are then manipulated using control actuators such as for example solenoid valves 110 and 116 to achieve the desired goals of temperature, temperature decrease and increase rate and balloon pressure.

Different types of sensors are contemplated for use within the system in order to monitor temperature T, pressure P, and how much coolant is flowing into the cryoapplicator. A flow sensor can be used that measures the rate or speed of fluid or gas at a certain location. The flow sensor can be a mass flow sensor, a hotwire anemometer, a magnetic field sensor, or an ultrasonic flow sensor. Alternately or in addition, one or more sensors may be pressure sensors. Pressure sensor can be an absolute, a gauge or a differential pressure sensor that can determine the amount of pressure in the balloon, the amount of vacuum or mass flow by measuring pressure drop across a known resistor. Certain degree of redundancy may be desired to prevent faults and failures. For example, if the mass flow of the refrigerant is not equal to the mass flow of the vapor the refrigerant leak may be present and detected. Excessive pressure in the supply line or sudden drop of pressure in the vacuum line can indicate an occlusion or a leak in the fluid path.

A temperature sensor, such as a thermocouple or thermistor, can be implemented in the cryocatheter to provide valuable data and feedback to the cryosystem. For example, a temperature sensor can be mounted in, on or proximate to the cryoapplicator to measure the interface/contact temperature between the cryoapplicator and tissue. Additionally or alternatively, a temperature sensor can be placed within the expansion chamber of the cryoapplicator to properly monitor the boiling temperature of the cryo fluid and enable control and regulation of system pressure.

The real time closed loop feedback system in the cryoconsole can be designed to maintain pressure inside the balloon at approximately arterial blood pressure level or slightly above it. This can be achieved by manipulating a flow regulator in the vacuum evacuation segment of the fluid path. The resulting balloon will loosely adhere to the arterial walls but not distend them.

A. Facilitating Warming

Balloon can be rapidly re-warmed by the application of heated gas. Heated gas can be at room temperature or higher and can displace the cryogen from the balloon using the same fluid path with the system of switch valves. A gentle tug on the tether should allow the operator to pull the balloon out of the renal artery and restore the blood flow.

The system can also include a subsystem for directing energy into the balloon to quickly thaw the frozen fluid and restore blood flow through the renal artery. For example a microwave or a radiofrequency (RF) heating device can be mounted on the cryocatheter to thaw the ice and facilitate removal of the balloon from the patient. Alternatively, warming can be achieved by passing a gas that creates an exothermic Joule-Thompson effect such as helium, hydrogen, or neon through the same fluid circuit.

At the end of the ablation phase, the control system may provide a method to insure a safe deflation in order to prevent damaging the vessel tissue during balloon deflation. The temperature sensor can be utilized to prevent premature deflation of the balloon until the system is warmed enough (the temperature in the balloon is higher than a predetermined temperature. When the temperature increases to greater than the predetermined temperature, the solenoid valve can open a pathway for a vacuum to collapse the balloon.

B. Cryodiagnostic—Freezing Nerve Reversibly

In addition to inducing permanent ablation, cryotherapy is capable of temporary electrical inactivation of nerves in a manner that enables a physician to test the likely results of ablation through a reversible process. Such a process is further referred to as cryodiagnostic, and generally involves cooling tissue to near freezing (e.g., to 0° C.) but well above a temperature at which the tissue would be ablated (e.g., −20° C.).

Systems and catheters described in this disclosure can be used for cryodiagnostic processes with minimal modifications. To perform a cryodiagnostic process a physician places the cryoapplicator in the renal artery, as would be done for ablation and applies cold in the low temperature range for the duration sufficient to disable nerves temporarily.

The physician then may monitor physiologic parameters known to reflect sympathetic renal nerve activity such as levels of renin and/or renal epinephrine. In addition, heart rate, oxygen saturation, muscular sympathetic nerve activity (MSNA) and/or blood pressure can be monitored. The physician may perform a challenge test such as electro stimulation of renal nerves or infusion of a chemical agent into renal artery known to promote a physiologic response mediated by renal nerves. Comparing a patient's response to the challenge test before and during cryodiagnostic can enable the physician to predict the patient's response to renal nerve ablation. If the response is positive, cryoablation may be performed using the same or different cryoapplicator.

CONCLUSION

Unless the context clearly requires otherwise, throughout the description and the examples, the words "comprise," "comprising," and the like are to be construed in an inclusive sense as opposed to an exclusive or exhaustive sense; that is to say, in the sense of "including, but not limited to." Words using the singular or plural number also include the plural or singular number, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the words "herein," "above," and "below" and words of similar import, when used in this application, shall refer to this application as a whole and not to any particular portions of this application.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while process steps or functions are presented in a given order, alternative embodiments may perform functions in a different order, or functions may be performed substantially concurrently. The teachings of the disclosure provided herein can be applied to other systems, not only the systems described herein. Furthermore, the various embodiments described herein can be combined to provide further embodiments.

All of the references cited herein are incorporated by reference. Aspects of the disclosure can be modified, if necessary, to employ the systems, functions and concepts of the above references and applications (as well as the references cited below) to provide yet further embodiments of the disclosure. For example, the apparatuses, methods and systems described herein may be used for therapeutic renal neuromodulation to reduce central sympathetic drive and sympathetic neural activity in a manner that treats at least one of the following diseases: hypertension, congestive heart failure, chronic kidney disease, renal failure, insulin resistance, diabetes, metabolic disorder, obesity, and sleep apnea. Various embodiments of methods, apparatuses, and systems for performing such therapeutic renal neuromodulation are described in greater detail in U.S. patent application Ser. Nos. 13/034,595, 13/034,602, and 13/034,610, filed Feb. 24, 2011. All of these applications are incorporated herein by reference in their entireties.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure. Accordingly, the disclosure and associated technology can encompass other embodiments not expressly shown or described herein.

We claim:

1. A cryo-catheter, comprising:
 an elongate shaft having a proximal end portion and an opposite distal end portion;
 a cryo-applicator at the distal end portion of the shaft, wherein the cryo-applicator is transformable between a low-profile delivery state and an expanded deployed state, and wherein the cryo-applicator includes—
  a cryo-balloon configured to contact a first partial circumference of an elongate body lumen when the cryo-applicator is in the deployed state within the body lumen, and
  an insulating balloon configured to contact a second partial circumference of the body lumen when the cryo-applicator is in the deployed state within the body lumen, wherein the first and second partial circumferences are different parts of a full circumference of the body lumen at a given position along a length of the body lumen; and
 a supply lumen extending along the length of the shaft, wherein the supply lumen is configured to supply refrigerant to the cryo-balloon, and wherein the insulating balloon is configured to receive expanding refrigerant from the cryo-balloon.

2. The cryo-catheter of claim 1 wherein the insulating balloon is more compliant than the cryo-balloon.

3. The cryo-catheter of claim 2 wherein the insulating balloon is compliant and the cryo-balloon is non-compliant.

4. The cryo-catheter of claim 2 wherein the insulating balloon and the cryo-balloon together are configured to fully occlude body lumens having different transverse cross-sectional diameters.

5. The cryo-catheter of claim 1, further comprising an exhaust lumen extending along the length of the shaft, wherein the exhaust lumen is configured to exhaust gaseous refrigerant from the cryo-applicator.

6. The cryo-catheter of claim 5 wherein the supply lumen, the cryo-balloon, the insulating balloon, and the exhaust lumen are fluidically connected to one another in series.

7. The cryo-catheter of claim 1 wherein the cryo-applicator includes a restriction orifice at a distal end portion of the supply lumen.

8. The cryo-catheter of claim 7 wherein the restriction orifice is within the cryo-balloon.

9. The cryo-catheter of claim 8 wherein the restriction orifice is configured to direct expanding refrigerant preferentially toward the first partial circumference of the body lumen when the cryo-applicator is in the deployed state within the body lumen.

10. The cryo-catheter of claim 7 wherein the restriction orifice includes a capillary tube having a smaller inner diameter than an inner diameter of the supply lumen.

11. The cryo-catheter of claim 1 wherein the cryo-applicator includes a proximal neck through which the insulating balloon is configured to receive refrigerant from the cryo-balloon.

12. The cryo-catheter of claim 1 wherein the cryo-applicator comprises a pressure sensor within the cryo-balloon.

13. A system for cryogenic renal neuromodulation, the system comprising:
 a cryo-catheter including—
  an elongate shaft having a proximal end portion and an opposite distal end portion,
  a cryo-applicator at the distal end portion of the shaft, wherein the cryo-applicator is transformable between a low-profile delivery state and an expanded deployed state, and wherein the cryo-applicator includes—
   a cryo-balloon configured to contact a first partial circumference of an elongate body lumen when the cryo-applicator is in the deployed state within the body lumen, and
   an insulating balloon configured to contact a second partial circumference of the body lumen when the cryo-applicator is in the deployed state within the body lumen, wherein the first and second partial circumferences are different parts of a full circumference of the body lumen at a given position along a length of the body lumen, and
  a supply lumen extending along the length of the shaft, wherein the supply lumen is configured to supply refrigerant to the cryo-balloon, and wherein the insulating balloon is configured to receive expanding refrigerant from the cryo-balloon; and
 a cryo-console operably associated with the cryo-applicator, wherein the cryo-console includes a source of refrigerant fluidically connected to the cryo-applicator through the supply lumen.

14. The system of claim 13 wherein:
 the cryo-catheter includes an exhaust lumen extending along the length of the shaft; and
 the exhaust lumen is configured to exhaust gaseous refrigerant from the cryo-applicator.

15. The system of claim 13 wherein the cryo-console includes a controller configured to regulate a flowrate of refrigerant moving from the source of liquid refrigerant toward the cryo-applicator based on feedback from the cryo-catheter.

16. The system of claim 13 wherein the source of refrigerant is a reusable cartridge.

* * * * *